United States Patent [19]
Gregor

[11] Patent Number: 5,486,512
[45] Date of Patent: Jan. 23, 1996

[54] QUINAZOLINE DERIVATIVES AS ACETYLCHOLINESTERASE INHIBITORS

[75] Inventor: Vlad E. Gregor, Ann Arbor, Mich.

[73] Assignee: Warner-Lambert Company, Morris Plains, N.J.

[21] Appl. No.: 214,911

[22] Filed: Mar. 17, 1994

Related U.S. Application Data

[63] Continuation of Ser. No. 911,662, Jul. 16, 1992, abandoned, which is a continuation-in-part of Ser. No. 736,888, Jul. 29, 1991, abandoned, Continuation of Ser. No. 911,662, Jul. 16, 1992, abandoned, which is a continuation-in-part of Ser. No. 736,888, Jul. 29, 1991, abandoned.

[51] Int. Cl.⁶ .......................... C07D 487/04; A61K 31/55
[52] U.S. Cl. .......................... 514/214; 540/543; 540/579; 544/245; 544/246; 544/252
[58] Field of Search .................................. 540/543, 579; 514/214

[56] References Cited

U.S. PATENT DOCUMENTS

| | | | |
|---|---|---|---|
| 2,992,221 | 7/1961 | Petersen | 540/579 |
| 3,271,396 | 9/1966 | Bernstein et al. | 260/251 |
| 3,745,216 | 7/1973 | Jen et al. | 424/251 |
| 3,932,407 | 1/1976 | Beverung, Jr. et al. | 260/256.4 |
| 4,220,771 | 9/1980 | Hermecz et al. | 544/252 |
| 4,395,554 | 7/1983 | Hermecz et al. | 544/252 |
| 4,428,952 | 1/1984 | Dorin et al. | 424/251 |
| 4,670,434 | 6/1987 | Venuti | 514/234 |
| 4,690,925 | 9/1987 | Fried et al. | 514/267 |
| 4,837,239 | 6/1989 | Benjamin et al. | 514/267 |

FOREIGN PATENT DOCUMENTS

| | | |
|---|---|---|
| 0205280A2 | 12/1986 | European Pat. Off. . |
| 0230234A1 | 7/1987 | European Pat. Off. . |
| 122688 | 4/1963 | New Zealand . |
| 124454 | 6/1964 | New Zealand . |
| 191828 | 3/1983 | New Zealand . |
| 201915 | 11/1985 | New Zealand . |
| 219242 | 4/1990 | New Zealand . |
| 1418822 | 12/1975 | United Kingdom . |
| 1456794 | 11/1976 | United Kingdom . |
| 2001638 | 2/1979 | United Kingdom . |

OTHER PUBLICATIONS

Abstract SU–605–614 (1978) As UZB Chem Growing A. Karimov, et al., "I. Synthesis of Methoxy–And Hydroxy–Substituted . . . ", translated from Khimiya Prirodnykh Soedinenii, No. 4, pp. 498–504, 1982.

A. Karimov, et al., "II. Synthesis of 5–Methoxy–. . . " Translated from Khimiya Prirodnykh Soedinenii, No. 3, pp. 396–397, 1983.

G. Devi, et al., "Potential CNS & CVS Agents: Syntheses Based on Vasicinone", *Indian Journal of Chemistry*, vol. 14B, May 1976, pp. 354–356.

A. D'yakonov, et al., "III. Pentamethylenequinazolones", Translated from Khimiya Prirodnykh Soedinenii, No. 4, pp. 465–469, 1986.

F. Kuffner, et al., "Uber die Konstitution eines Nebenalkaloides aus Adhatoda vasica Nees", *Monatshefte fur Chemie*, Bd. 91/6, pp. 1153–1161, (1960).

Kh. Shakhidoyatov, et al., "Condensation of Acetanilides with N–Methylolpyrrolidone", translated from Khimiya Geterotsiklicheskikh Soedinenii, No. 6, pp. 834–837.

Abstract J5 3044–597 (1978) Daiichi Pharm KK.
Abstract J5 2077–093 (1977) Chugai Pharmaceutical KK.
Abstract J4 9076–899 (1974) Nippon Chemipha Co. Ltd.
Research Disclosure 183003, Crenshaw, R., et al., "Process for the preparation of cardiovascular agents", 55676B.
PCT International Search Report, International Application No. PCT/US 92/05864 filed Jul. 22, 1992.
Langluis et al., J. Het. Chem., 20, pp. 393–398 (1983).
Burger, *Medicinal Chemistry*, 3rd ed (1970), Part I, pp. 72–75.
Malhorta et al., Chem. Abstract 112:7445p (1989).
Hermecz et al., Chem. Abstract 107:198290p (1987).
Brown et al., Chem. Abstract 84:43969z (1975).
Irisbaev et al., Chem. Abstract 84:4894b (1975).
Shalchildoyatov et al., Chem. Abst. 86:106517q (1976).
Ishikawa et al., Chem. Abst. 89:109566c (1976).
*Drug Evaluations*, 6th ed (1986), Amer. Med Assn., pp. 160–162.
*Cecil Textbook of Medicine*, 19th ed (1992), Wyngaarden, M.D. editor, pp. 2075–2079.

*Primary Examiner*—Philip I. Datlow
*Attorney, Agent, or Firm*—Elizabeth M. Anderson

[57] ABSTRACT

A method of treating cognitive deficiencies is described by administering a quinazoline derivative of the general formula

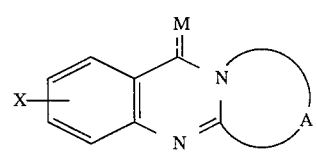

wherein A represents

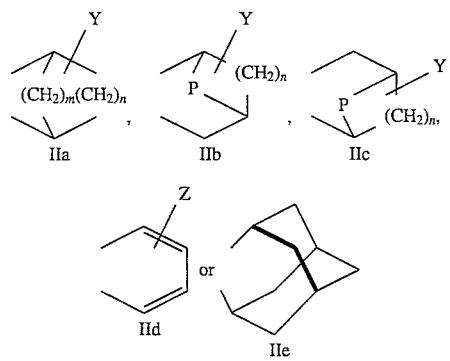

in which n is 1–10, P is a bond or $(CH_2)_m$ in which m is 0–10, and M is =O, =S, =NR, =CRR', (Abstract continued on next page.)

novel compounds of the above are also described as well as methods of manufacture and pharmaceutical compositions.
11 Claims, No Drawings

QUINAZOLINE DERIVATIVES AS ACETYLCHOLINESTERASE INHIBITORS

CROSS REFERENCE TO RELATED APPLICATION

This is a Continuation of U.S. Ser. No. 07/911,662, filed Jul. 16, 1992, now abandoned; which is a Continuation-in-Part of U.S. Ser. No. 07/736,888 filed Jul. 29, 1991, now abandoned.

BACKGROUND OF THE INVENTION

The present invention is directed to a new method of treating cognitive deficiencies such as memory loss, Alzheimer's disease, and other dementias using dihydroquinazoline derivatives as the active ingredients.

Tetrahydroacridine derivatives have been reported to possess acetylcholinesterase inhibiting activity, which properties have been found useful in the treatment of cognitive deficit states. For example, tacrine, 9-amino-1,2,3,4-tetrahydroaminoacridine, has proved effective in the alleviation of symptoms of Alzheimer's disease. Dependent on the dosing sequence for effective results, use of tetrahydroaminoacridines may cause liver toxicity. Tetrahydroaminoacridines are also known to be mutagenic.

It has now been found that certain quinazoline derivatives also possess cholinesterase inhibiting activity and are thus useful for treating cognitive deficiencies such as: Alzheimer's disease, senile dementias, multiple infarct dementias, and other conditions where memory and cognitive function improvement or stabilization is desired. The present quinazoline derivatives may also be useful in eliminating symptoms of tardive dyskinesia, e.g., induced by tricyclic antidepressants, Huntington's chorea, and the side effects caused by centrally acting anticholinergics, e.g., tricyclic antidepressants, scopolamine, quinuclidinyl benzilate and the like. The above compounds would also be useful in the treatment of manic depressive disorder.

It is believed that the present quinazoline derivatives lacking the aromatic amine moiety of the tetrahydroaminoacridines will not possess the toxicity of the tetrahydroaminoacridines.

SUMMARY OF THE INVENTION

Accordingly the present invention comprises a method of treating cognitive deficiencies comprising administering to a host in need thereof a therapeutically effective amount in unit dosage form of a compound of the formula

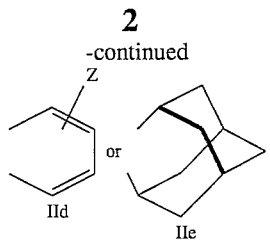

(I)

wherein A is absent or represents

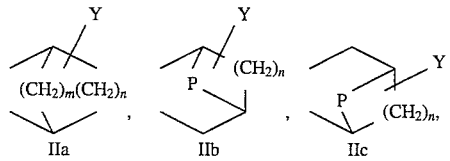

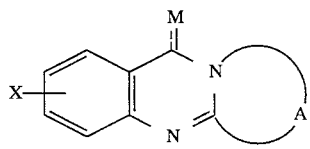

in which n is 1–10, P is a bond or $(CH_2)_m$ in which m is 0–10, wherein a nitrogen, oxygen, or sulfur atom may replace a methylene group in ring A and attached to a carbon atom in ring A is Y, in which Y is hydrogen, hydroxy, carboxy, lower alkoxy, lower alkyl, aryl, heteroaryl, keto, lower alkoxycarbonyl, lower alkanoyl, or oxime thereof;

M is =O, =S, =NR,

or =CRR', in which R and R' are each independently hydrogen, lower alkyl, hydroxy, lower alkenyl, lower alkoxy, lower alkynyl, aryl, aryloxy, aryl lower alkyl, heteroaryl, or heteroaryllower alkyl and, when taken together, may form a three- to six-membered ring optionally containing one to three heteroatoms selected from nitrogen, oxygen, and sulfur; and X is absent or one to four substituents selected from hydrogen, halogen, alkyl($C_{1-22}$), straight or branched, saturated or alkenyl or alkynyl, if alkyl of appropriate size can form a ring, saturated or unsaturated, containing (or not containing) one or more heteroatoms, such as O, S, N, Se, P, and the like, or an aromatic or heteroaromatic ring containing (or not containing) one or more heteroatoms, such as O, S, N, Se, and the like, primary, secondary, or tertiary amino, nitro, lower alkylthio, or aryl (or heteroaryl)thio, mercapto, hydroxy, carboxy, lower alkoxy, or aryl (or heteroaryl)oxy, alkyl($C_{1-22}$), or aryl (or heteroaryl)sulfinyl, alkyl($C_{1-22}$), or aryl (or heteroaryl)sulfonyl, perfluoroalkyl($C_{1-22}$), such as trifluoromethyl, perfluoroalkoxy($C_{1-22}$), such as trifluoromethoxy, perfluoroalkylthio($C_{1-22}$), such as trifluoromethylthio, perfluoroalkylsulfinyl($C_{1-22}$), such as trifluoromethylsulfinyl, perfluoroalkylsulfonyl($C_{1-22}$), such as trifluoromethylsulfonyl, alkyl($C_{1-22}$), or aryl (or heteroaryl)carbamoyl, or diacylamino, including cyclic imido, such as succinimido, alkyl($C_{1-22}$), or aryl (or heteroaryl)sulfinylamido, alkyl($C_{1-22}$), or aryl (or heteroaryl)sulfonylamido, perfluoroalkyl($C_{1-22}$)sulfinylamido, such as trifluoromethylsulfinylamido, perfluoroalkyl($C_{1-22}$)sulfonylamido, such as trifluoromethylsulfonylamido above, trialkylsilyl, such as trimethylsilyl, or triethylsilyl, acyl, such as acetyl, benzoyl, phenylacetyl, hydrocinnamoyl, and the like, perfluoroacyl, such as trifluoroacetyl, heptafluorobutyryl, and the like, acyl-lower alkyl, such as acetylmethyl, benzoylmethyl, phenylacetylmethyl, hydrocinnamoylmethyl, and the like, perfluoroacyl-lower alkyl, such as trifluoroacetylmethyl, heptafluorobutyrylmethyl, and the like, alkyl($C_{1-22}$), or aryl (or heteroaryl)carbamoyloxy, dialkyl($C_{1-22}$), or diaryl (or diheteroaryl)carbamoyloxy, alkyl($C_{1-22}$), or aryl (or heteroaryl)carbamoylthio, alkyl($C_{1-22}$), or aryl (or heteroaryl)carbamoylalkyl, or diacylaminoalkyl, including cyclic imidoalkyl, such as acetamidomethyl, octanamidomethyl, or succinimidomethyl, aryl, or aryl lower alkyl including substituted aryl with groups such as halogen and groups described above, heteroaryl or heteroaryllower alkyl, such as furan, thiophene, pyrrole, pyridine and the like, including substituted derivatives with groups such as halogen and groups described above;

Z is hydrogen, halogen, alkyl ($C_{1-12}$), straight or branched, saturated or alkenyl or alkynyl if alkyl of appropriate size can form a ring, saturated or unsaturated, containing or not containing one or more heteroatoms, selected from O, S, and N, can also form an aromatic or heteroaromatic ring containing or not containing one or more heteroatoms, selected from O, S, and N, primary, secondary, or tertiary amino-lower alkylthio-, aryl-, heteroarylthio, mercapto, hydroxy, carboxy, carbalkoxy in which alkyl is $C_1$–$C_{22}$, lower alkoxy, aryl, or heteroaryloxy, perfluoroalkyl in which alkyl is $C_1$–$C_{22}$, perfluoroalkoxy in which alkyl portion is $C_1$–$C_{22}$), alkyl ($C_{1-22}$), aryl or heteroarylcarbamoyl, diacylamino, cyclic imido, or acyl, or a pharmaceutically acceptable acid addition salt thereof, with the proviso that when A is

IIa in which n is 1, m is 0, Y is hydrogen, and M is RR' where R and R' are both hydrogen, X is not absent nor a single methoxy or hydroxy group.

The present invention also includes novel compounds of the formula

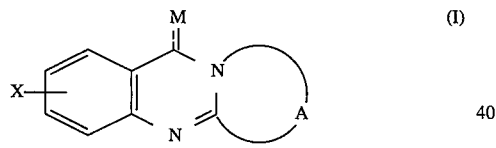
(I)

wherein A represents

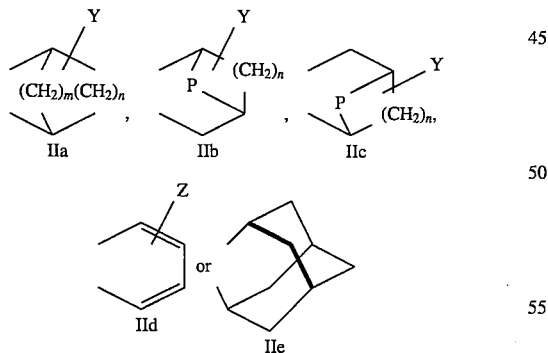

in which n is 1–10, P is a bond or $(CH_2)_m$ in which m is 0–10, wherein a nitrogen, oxygen, or sulfur atom may replace a methylene group in ring A, which is not adjacent to the quinazoline moiety, and attached to a carbon atom in ring A is Y, in which Y is hydrogen, hydroxy, halogen, carboxy, lower alkoxy, lower alkyl, aryl, heteroaryl, keto, lower alkoxy carbonyl or lower alkanoyl;

M is =S, =NR,

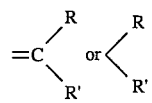

in which R and R' are independently hydrogen, hydroxy, lower alkyl, lower alkoxy, lower alkenyl, lower alkynyl, aryl, aryloxy, aryllower alkyl, heteroaryl or heteroaryllower alkyl and, when taken together, may form a three- to six-membered ring optionally containing one to three heteroatoms selected from nitrogen, oxygen, and sulfur; and X is absent or one to four substituents selected from halogen, alkyl ($C_{1-22}$), straight or branched, saturated or alkenyl or alkynyl, if alkyl of appropriate size can form a ring, saturated or unsaturated, containing (or not containing) one or more heteroatoms, such as O, S, N, Se, P, and the like, or an aromatic or heteroaromatic ring containing (or not containing) one or more heteroatoms, such as O, S, N, Se, and the like, primary, secondary, or tertiary amino nitro-lower alkylthio, or aryl (or heteroaryl)thio, mercapto, hydroxy, carboxy, lower alkoxy, or aryl (or heteroaryl)oxy, alkyl($C_{1-22}$) or aryl (or heteroaryl)sulfinyl, alkyl($C_{1-22}$), or aryl (or heteroaryl)sulfonyl, perfluoroalkyl($C_{1-22}$), such as trifluoromethyl, perfluoroalkoxy($C_{1-22}$), such as trifluoromethoxy, perfluoroalkylthio($C_{1-22}$), such as trifluoromethylthio, perfluoroalkylsulfinyl($C_{1-22}$), such as trifluoromethylsulfinyl, perfluoroalkylsulfonyl($C_{1-22}$), such as trifluoromethylsulfonyl, alkyl($C_{1-22}$), or aryl (or heteroaryl)carbamoyl, or diacylamino, including cyclic imido, such as succinimido, alkyl($C_{1-22}$), or aryl (or heteroaryl)sulfinylamido, alkyl($C_{1-22}$), or aryl (or heteroaryl)sulfonylamido, perfluoroalkyl($C_{1-22}$)sulfinylamido, such as trifluoromethylsulfinylamido, perfluoroalkyl($C_{1-22}$)sulfonylamido, such as trifluoromethylsulfonylamido above, trialkylsilyl, such as trimethylsilyl, or triethylsilyl, acyl, such as acetyl, benzoyl, phenylacetyl, hydrocinnamoyl, and the like, perfluoroacyl, such as trifluoroacetyl, heptafluorobutyryl, and the like, acyl-lower alkyl, such as acetylmethyl, benzoylmethyl, phenylacetylmethyl, hydrocinnamoylmethyl, and the like, perfluoroacyl-lower alkyl, such as trifluoroacetylmethyl, heptafluorobutyrylmethyl, and the like, alkyl($C_{1-22}$), or aryl (or heteroaryl)carbamoyloxy, dialkyl($C_{1-22}$), or diaryl (or diheteroaryl)carbamoyloxy, alkyl($C_{1-22}$), or aryl (or heteroaryl)carbamoylthio, alkyl($C_{1-22}$), or aryl (or heteroaryl)carbamoylalkyl, or diacylaminoalkyl, including cyclic imidoalkyl, such as acetamidomethyl, octanamidomethyl, or succinimidomethyl, aryl or aryl lower alkyl, including substituted aryl with groups such as halogen and groups described, heteroaryl or heteroaryllower alkyl, such as furan, thiophene, pyrrole, pyridine and the like, including substituted derivatives with groups such as halogen and groups described above;

Z is hydrogen, halogen, alkyl($C_{1-12}$), straight or branched, saturated or alkenyl or alkynyl if alkyl of appropriate size can form a ring, saturated or unsaturated, containing or not containing one or more heteroatoms, selected from O, S, and N, can also form an aromatic or heteroaromatic ring containing or not containing one or more heteroatoms, selected from O, S, and N, primary, secondary, or tertiary aminolower alkylthio-, aryl-, heteroarylthio, mercapto, hydroxy, carboxy, carbalkoxy in which alkyl is $C_1$–$C_{22}$, lower alkoxy, aryl, or heteroaryloxy, perfluoroalkyl in which alkyl is $C_1$–$C_{22}$, perfluoroalkoxy in which alkyl portion is $C_1$–$C_{22}$), alkyl($C_{1-22}$), aryl or heteroarylcarbamoyl, diacylamino, cyclic imido, or acyl, or a pharmaceutically acceptable acid addition salt thereof; with the proviso that when A is

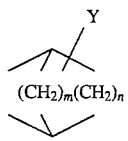
IIa in which n is 1–3, m is 0, Y is hydrogen, and M is RR' where R and R' are both hydrogen, X cannot be absent or a single hydroxy or methoxy group; and when A if of the Formula IId, X is 1,3-dihalogeno or 2,4-dihalogeno.

The present invention further includes pharmaceutical compositions for treating cognitive deficiencies where the above compounds as active ingredients in therapeutically effective amounts are admixed with one or more pharmaceutically acceptable carriers, excipients, and/or diluents.

DESCRIPTION OF PREFERRED EMBODIMENTS

The quinazoline derivatives of the present invention are represented by the above Formula I. The compounds are actually tricyclic, tetracyclic, pentacyclic, or hexacyclic depending on the definition of A.

The quinazoline moiety of the compounds of the invention are described as having the formula

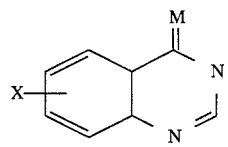
III

Substituent X includes one to four substituents as defined above on the aromatic ring shown in Formula I.

Preferred X substituents are independently up to four substituents selected from halogen, lower alkyl, perfluorinated lower alkyl, hydroxy, carboxy, mercapto, lower alkoxy, lower thioalkoxy, perfluorinated lower alkoxy, perfluorinated lower thioalkoxy, nitro, amino, lower alkanoylamino, aryl, aryllower alkyl, heteroaryl, heteroaryllower alkyl, trialkylsilyl, such as trimethylsilyl, or triethylsilyl, acyl, such as acetyl, benzoyl, phenylacetyl, hydrocinnamoyl and the like, perfluoroacyl, such as trifluoroacetyl, heptafluorobutyryl and the like, acyl-lower alkyl, such as acetylmethyl, benzoylmethyl, phenylacetylmethyl, hydrocinnamoylmethyl and the like, perfluoroacyl-lower alkyl, such as trifluoroacetylmethyl, heptafluorobutyrylmethyl and the like, alkyl ($C_{1-12}$), or aryl (or heteroaryl)carbamoyloxy, dialkyl($C_{1-12}$, or diaryl (or diheteroaryl)carbamoyloxy, alkyl($C_{1-12}$), or aryl or (heteroaryl)carbamoylthio, and alkyl($C_{1-12}$), or aryl (or heteroaryl)carbamoylalkyl, or diacylaminoalkyl, including cyclic imidoalkyl, such as acetamidomethyl, octanamidomethyl, or succinimidomethyl.

The group A shown by the above Formula IIa, IIb, and IIc is attached at two bond sites to the dihydroquinazoline moiety to form a monocyclic or bicyclic ring of members defined by n and m. The monocyclic or bicyclic ring may contain substituents defined by Y. These substituents are attached only at carbon atoms of the monocyclic or bicyclic ring. Furthermore, the monocyclic or bicyclic ring may include a heteroatom such as nitrogen, oxygen, or sulfur replacing a methylene group which is not adjacent to the quinazoline moiety. For example, the following A groups are illustrative:

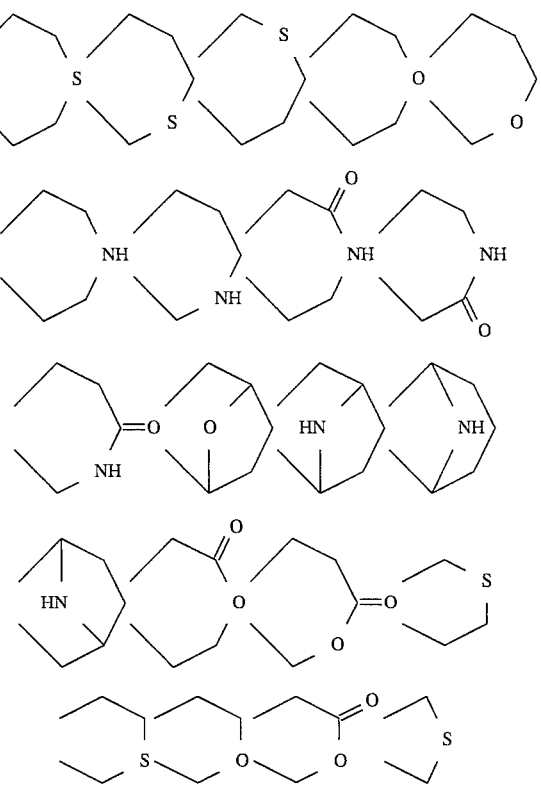

The following is a detailed definition of the terms used to describe the compounds of the present invention shown in the above Formula I.

The term "lower" when preceding "alkyl" or "alk . . ." designates a range of 1 to 8 carbon atoms in a straight or branched hydrocarbon chain and, preferably, 1 to 4 carbon atoms when "lower" follows "aryl" or "heteroaryl". Thus, for example, lower alkyl includes methyl, ethyl, propyl, isopropyl, butyl, isobutyl, tert.-butyl, and the like. In the case of alkenyl, alkynyl, and alkanoyl, the range of carbon atoms is 2 to 8 when preceded by "lower" and includes, for example, vinyl, allyl, ethenyl, propargyl, acetyl, propionyl, and the like.

Aryl means an aromatic ring such as phenyl or phenyl substituted by lower alkyl, hydroxy, lower alkoxy, halogen, trifluoromethyl, nitro or amino, lower alkylamino, or di-loweralkyl amino.

Heteroaryl means an aromatic ring of 5 or 6 members having one or more heteroatoms such as nitrogen, oxygen, and/or sulfur and further includes a bicyclic system where another aromatic ring is condensed to the heteroaromatic ring, for example, indole, benzofuran, or benzothiophene. By way of illustration, the following are examples of heteroaromatic rings:

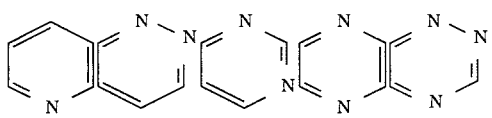

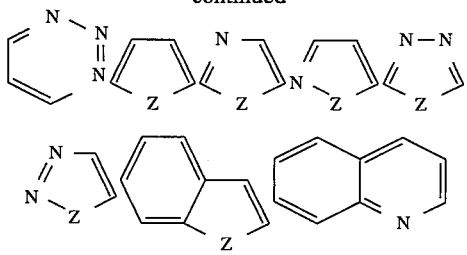

where Z is NH, O or S. The heteroaromatic rings may also be substituted as aryl defined above.

A perfluorinated lower alkyl or aryl group is any of the lower alkyl or aryl groups defined above where all of the hydrogen atoms attached to the carbon atoms on the hydrocarbon skeleton have been replaced by a fluorine atom, e.g., trifluoromethyl.

Halogen means fluorine, chlorine, bromine, and iodine.

Included as part of the present invention are novel compounds of the Formula I.

Preferred are compounds of the formula

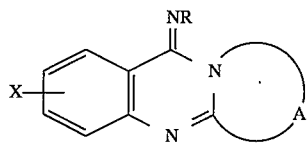

wherein A represents

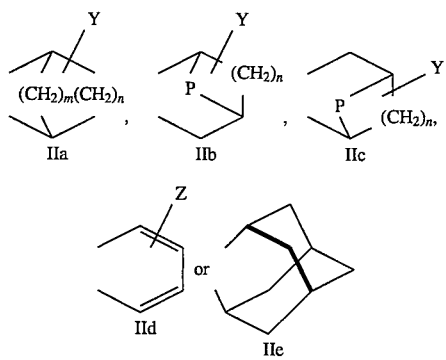

in which n is 1–10, P is a bond or $(CH_2)_m$ in which m is 0–4, wherein a nitrogen, oxygen or sulfur atom may replace a methylene group in ring A and attached to a carbon atom in ring A is Y, in which Y is hydrogen, hydroxy, lower alkoxy, lower alkyl, aryl, heteroaryl, keto, lower alkoxy carbonyl or lower alkanoyl;

R is hydrogen, hydroxy, lower alkyl, lower alkoxy, lower alkenyl, lower alkynyl, aryl, aryloxy, arylower alkyl, heteroaryl, or heteroaryllower alkyl; and X is absent or one to four substituents selected from halogen, lower alkyl, perfluorinated lower alkyl, hydroxy, carboxy, mercapto, lower alkoxy, lower thioalkoxy, perfluorinated lower alkoxy, perfluorinated lower thioalkoxy, nitro, amino, lower alkanoylamino, aryl, aryllower alkyl, heteroaryl, and heteroaryllower alkyl, Z is defined above; or a pharmaceutically acceptable acid addition salt thereof; with the provision that when A is of the Formula IId, X is 1,3-dihalogeno.

More preferred are compounds of Formula IV, wherein

Y is hydrogen, hydroxy, carboxy, lower alkoxy, lower alkyl, keto, lower alkoxycarbonyl, and lower alkanoyl;

R is hydrogen, hydroxy, lower alkyl, lower alkoxy, lower alkenyl, or lower alkynyl; and X is absent or one to four substituents selected from halogen, lower alkyl, perfluorinated lower alkyl, hydroxy, carboxy, lower alkoxy, perfluorinated lower alkoxy, nitro, amino, or lower alkanoyl amino and lower alkylcarbamoyloxy.

Most preferred are compounds of Formula IV, wherein Y and R are hydrogen; n is 1 to 3, and m is 0 to 3, and X is absent or one to four substituents selected from hydrogen, halogen, lower alkyl, and perfluorinated lower alkyl. Especially preferred of these are those compounds wherein X is absent or one to four substituents selected from fluoro, chloro, bromo, iodo, methyl, methylcarbamoyloxy, heptylcarbamoyloxy, and trifluoromethyl.

Particularly valuable are:
1-methyl-7,8,9,10-tetrahydroazepino[2,1-b]quinazoline-12(6H)-imine,
2-methyl-7,8,9,10-tetrahydroazepino[2,1-b]quinazoline-12(6H)-imine,
3-methyl-7,8,9,10-tetrahydroazepino[2,1-b] quinazoline-12(6H)-imine,
4-methyl-7,8,9,10-tetrahydroazepino[2,1-b] quinazoline-12(6H)-imine,
1-chloro-7,8,9,10-tetrahydroazepino[2,1-b]quinazoline-12(6H)-imine,
2-chloro-7,8,9,10-tetrahydroazepino[2,1-b] quinazoline-12(6H)-imine,
3-chloro-7,8,9,10-tetrahydroazepino[2,1-b] quinazoline-12(6H)-imine,
4-chloro-7,8,9,10-tetrahydroazepino[2,1-b] quinazoline-12(6H)-imine,
1-bromo-7,8,9,10-tetrahydroazepino[2,1-b] quinazoline-12(6H)-imine,
2-bromo-7,8,9,10-tetrahydroazepino[2,1-b] quinazoline-12(6H)-imine,
3-bromo-7,8,9,10-tetrahydroazepino[2,1-b] quinazoline-12(6H)-imine,
4-bromo-7,8,9,10-tetrahydroazepino[2,1-b] quinazoline-12(6H)-imine,
1-fluoro-7,8,9,10-tetrahydroazepino[2,1-b] quinazoline-12(6H)-imine,
2-fluoro-7,8,9,10-tetrahydroazepino[2,1-b] quinazoline-12(6H)-imine,
3-fluoro-7,8,9,10-tetrahydroazepino[2,1-b] quinazoline-12(6H)-imine,
4-fluoro-7,8,9,10-tetrahydroazepino[2,1-b] quinazoline-12(6H)-imine,
1-(trifluoromethyl)-7,8,9,10-tetrahydroazepino[2,1-b] quinazoline-12(6H)-imine,
2-(trifluoromethyl)-7,8,9,10-tetrahydroazepino[2,1-b] quinazoline-12(6H)-imine,
3-(trifluoromethyl)-7,8,9,10-tetrahydroazepino[2,1-b] quinazoline-12(6H)-imine,
4-(trifluoromethyl)-7,8,9,10-tetrahydroazepino[2,1-b] quinazoline-12(6H)-imine,
1,2-dichloro-7,8,9,10-tetrahydroazepino[2,1-b] quinazoline-12(6H)-imine,
1,3-dichloro-7,8,9,10-tetrahydroazepino[2,1-b] quinazoline-12(6H)-imine,
1,4-dichloro-7,8,9,10-tetrahydroazepino[2,1-b] quinazoline-12(6H)-imine,
2,3-dichloro-7,8,9,10-tetrahydroazepino[2,1-b] quinazoline-12(6H)-imine,
2,4-dichloro-7,8,9,10-tetrahydroazepino[2,1-b] quinazoline-12(6H)-imine,
3,4-dichloro-7,8,9,10-tetrahydroazepino[2,1-b] quinazoline-12(6H)-imine, 1,2-dibromo-7,8,9,10-tetrahydroazepino[2,1-b]quinazoline-12(6H)-imine,
1,3-dibromo-7,8,9,10-tetrahydroazepino[2,1-b]quinazoline-12(6H)-imine,
1,4-dibromo-7,8,9,10-tetrahydroazepino[2,1-b]quinazoline-12(6H)-imine,
2,3-dibromo-7,8,9,10-tetrahydroazepino[2,1-b]quinazoline-12(6H)-imine,
2,4-dibromo-7,8,9,10-tetrahydroazepino[2,1-b]quinazoline-12(6H)-imine,
3,4-dibromo-7,8,9,10-tetrahydroazepino[2,1-b]quinazoline-12(6H)-imine,
2,3-dimethoxy-7,8,9,10-tetrahydroazepino[2,1-b]quinazoline-12(6H)-imine,
2,4-dimethoxy-7,8,9,10-tetrahydroazepino[2,1-b]quinazoline-12(6H)-imine,
3,4-dimethoxy-7,8,9,10-tetrahydroazepino[2,1-b]quinazoline-12(6H)-imine,
1,2-dimethyl-7,8,9,10-tetrahydroazepino[2,1-b]quinazoline-12(6H)-imine,
1,3-dimethyl-7,8,9,10-tetrahydroazepino[2,1-b]quinazoline-12(6H)-imine,
1,4-dimethyl-7,8,9,10-tetrahydroazepino[2,1-b]quinazoline-12(6H)-imine,
2,3-dimethyl-7,8,9,10-tetrahydroazepino[2,1-b]quinazoline-12(6H)-imine,
2,4-dimethyl-7,8,9,10-tetrahydroazepino[2,1-b]quinazoline-12(6H)-imine,
3,4-dimethyl-7,8,9,10-tetrahydroazepino[2,1-b]quinazoline-12(6H)-imine,
3-chloro-1-methyl-7,8,9,10-tetrahydroazepino[2,1-b]quinazoline-12(6H)-imine,
1-methyl-6,7,8,9-tetrahydro-11H-pyrido[2,1-b]quinazolin-11-imine,
2-methyl-6,7,8,9-tetrahydro-11H-pyrido[2,1-b]quinazolin-11-imine,
3-methyl-6,7,8,9-tetrahydro-11H-pyrido[2,1-b]quinazolin-11-imine,
4-methyl-6,7,8,9-tetrahydro-11H-pyrido[2,1-b]quinazolin-11-imine,
1-chloro-6,7,8,9-tetrahydro-11H-pyrido[2,1-b]quinazoline-11-imine,
2-chloro-6,7,8,9-tetrahydro-11H-pyrido[2,1-b]quinazolin-11-imine,
3-chloro-6,7,8,9-tetrahydro-11H-pyrido[2,1-b]quinazolin-11-imine,
4-chloro-6,7,8,9-tetrahydro-11H-pyrido[2,1-b]quinazolin-11-imine,
1-bromo-6,7,8,9-tetrahydro-11H-pyrido[2,1-b]quinazolin-11-imine,
2-bromo-6,7,8,9-tetrahydro-11H-pyrido[2,1-b]quinazolin-11-imine,
3-bromo-6,7,8,9-tetrahydro-11H-pyrido[2,1-b]quinazolin-11-imine,
4-bromo-6,7,8,9-tetrahydro-11H-pyrido[2,1-b]quinazolin-11-imine,
1,2-dichloro-6,7,8,9-tetrahydro-11H-pyrido[2,1-b]quinazolin-11-imine,
1,3-dichloro-6,7,8,9-tetrahydro-11H-pyrido[2,1-b]quinazolin-11-imine,
1,4-dichloro-6,7,8,9-tetrahydro-11H-pyrido[2,1-b]quinazolin-11-imine,
2,3-dichloro-6,7,8,9-tetrahydro-11H-pyrido[2,1-b]quinazolin-11-imine, 2,4-dichloro-6,7,8,9-tetrahydro-11H-pyrido[2,1-b]quinazolin-11-imine,
3,4-dichloro-6,7,8,9-tetrahydro-11H-pyrido[2,1-b]quinazolin-11-imine,
1,2-dibromo-6,7,8,9-tetrahydro-11H-pyrido[2,1-b]quinazolin-11-imine,
1,3-dibromo-6,7,8,9-tetrahydro-11H-pyrido[2,1-b]quinazolin-11-imine,
1,4-dibromo-6,7,8,9-tetrahydro-11H-pyrido[2,1-b]quinazolin-11-imine,
2,3-dibromo-6,7,8,9-tetrahydro-11H-pyrido[2,1-b]quinazolin-11-imine,
2,4-dibromo-6,7,8,9-tetrahydro-11H-pyrido[2,1-b]quinazolin-11-imine,
3,4-dibromo-6,7,8,9-tetrahydro-11H-pyrido[2,1-b]quinazolin-11-imine,
1-methyl-2,3-dihydropyrrolo[2,1-b]quinazolin-9(1H)-imine,
2-methyl-2,3-dihydropyrrolo[2,1-b]quinazolin-9(1H)-imine,
3-methyl-2,3-dihydropyrrolo[2,1-b]quinazolin-9(1H)-imine,
4-methyl-2,3-dihydropyrrolo[2,1-b]quinazolin-9(1H)-imine,
1-chloro-2,3-dihydropyrrolo[2,1-b]quinazolin-9(1H)-imine,
2-chloro-2,3-dihydropyrrolo[2,1-b]quinazolin-9(1H)-imine,
3-chloro-2,3-dihydropyrrolo[2,1-b]quinazolin-9(1H)-imine,
4-chloro-2,3-dihydropyrrolo[2,1-b]quinazolin-9(1H)-imine,
1-bromo-2,3-dihydropyrrolo[2,1-b]quinazolin-9(1H)-imine,
2-bromo-2,3-dihydropyrrolo[2,1-b]quinazolin-9(1H)-imine,
3-bromo-2,3-dihydropyrrolo[2,1-b]quinazolin-9(1H)-imine,
4-bromo-2,3-dihydropyrrolo[2,1-b]quinazolin-9(1H)-imine,
1-methyl-11H-pyrido[2,1-b]quinazolin-11-imine,
2-methyl-11H-pyrido[2,1-b]quinazolin-11-imine,
3-methyl-11H-pyrido[2,1-b]quinazolin-11-imine,
4-methyl-11H-pyrido[2,1-b]quinazolin-11-imine,
1-chloro-11H-pyrido[2,1-b]quinazolin-11-imine,
2-chloro-11H-pyrido[2,1-b]quinazolin-11-imine,
3-chloro-11H-pyrido[2,1-b]quinazolin-11-imine,
4-chloro-11H-pyrido[2,1-b]quinazolin-11-imine,
1-fluoro-11H-pyrido[2,1-b]quinazolin-11-imine,
2-fluoro-11H-pyrido[2,1-b]quinazolin-11-imine,
3-fluoro-11H-pyrido[2,1-b]quinazolin-11-imine,
4-fluoro-11H-pyrido[2,1-b]quinazolin-11-imine,
1-bromo-11H-pyrido[2,1-b]quinazolin-11-imine,
2-bromo-11H-pyrido[2,1-b]quinazolin-11-imine,
3-bromo-11H-pyrido[2,1-b]quinazolin-11-imine,
4-bromo-11H-pyrido[2,1-b]quinazolin-11-imine,
1-(trifluoromethyl)-11H-pyrido[2,1-b]quinazolin-11-imine,
2-(trifluoromethyl)-11H-pyrido[2,1-b]quinazolin-11-imine,
3-(trifluoromethyl)-11H-pyrido[2,1-b]quinazolin-11-imine,
4-(trifluoromethyl)-11H-pyrido[2,1-b]quinazolin-11-imine,
1-(methylthio)-11H-pyrido[2,1-b]quinazolin-11-imine,
2-(methylthio)-11H-pyrido[2,1-b]quinazolin-11-imine,
3-(methylthio)-11H-pyrido[2,1-b]quinazolin-11-imine,
4-(methylthio)-11H-pyrido[2,1-b]quinazolin-11-imine,
1,2-dichloro-11H-pyrido[2,1-b]quinazolin-11-imine,
1,3-dichloro-11H-pyrido[2,1-b]quinazolin-11-imine,
1,4-dichloro-11H-pyrido[2,1-b]quinazolin-11-imine,
2,3-dichloro-11H-pyrido[2,1-b]quinazolin-11-imine,
2,4-dichloro-11H-pyrido[2,1-b]quinazolin-11-imine,
3,4-dichloro-11H-pyrido[2,1-b]quinazolin-11-imine,
1,3-dimethoxy-11H-pyrido[2,1-b]quinazolin-11-imine,
2,3-dimethoxy-11H-pyrido[2,1-b]quinazolin-11-imine,
2,4-dimethoxy-11H-pyrido[2,1-b]quinazolin-11-imine,
3,4-dimethoxy-11H-pyrido[2,1-b]quinazolin-11-imine,
1,2-dimethyl-11H-pyrido[2,1-b]quinazolin-11-imine,
1,3-dimethyl-11H-pyrido[2,1-b]quinazolin-11-imine,
1,4-dimethyl-11H-pyrido[2,1-b]quinazolin-11-imine, 2,3-dimethyl-11H-pyrido[2,1-b]quinazolin-11-imine,
2,4-dimethyl-11H-pyrido[2,1-b]quinazolin-11-imine,
3,4-dimethyl-11H-pyrido[2,1-b]quinazolin-11-imine,
2-(methylcarbamoyloxy)-11H-pyrido[2,1-b]quinazolin-11-imine,
1-chloro-2-(methylcarbamoyloxy)-11H-pyrido[2,1-b]quinaolin-11-imine,
3-chloro-2-(methylcarbamoyloxy)-11H-pyrido[2,1-b]quinaolin-11-imine,
1-chloro-3-(methylcarbamoyloxy)-11H-pyrido[2,1-b]quinaolin-11-imine,
2-(heptylcarbamoyloxy)-11H-pyrido[2,1-b]quinazolin-11-imine,
3-(heptylcarbamoyloxy)-11H-pyrido[2,1-b]quinazolin-11-imine,
1-chloro-3-(heptylcarbamoyloxy)-11H-pyrido[2,1-b]quinazolin-11-imine,
3-chloro-2-(heptylcarbamoyloxy)-11H-pyrido[2,1-b]quinazolin-11-imine,
1,3-dichloro-2-(heptylcarbamoyloxy)-11H-pyrido[2,1-b]quinazolin-11-imine,
1-chloro-3-methyl-11H-pyrido[2,1-b]quinazolin-11-imine,
1-methyl-3-chloro-11H-pyrido[2,1-b]quinazolin-11-imine,
1,3-dichloro-11H-pyrido[2,1-b]quinazolin-11-methylimine,
1,3-dichloro-11H-pyrido[2,1-b]quinazolin-11-(2-phenylethyl)-imine,
1,3-difluoro-11H-pyrido[2,1-b]quinazolin-11-imine,
1-fluoro-3-bromo-11H-pyrido[2,1-b]quinazolin-11-imine,
1-fluoro-3-iodo-11H-pyrido[2,1-b]quinazolin-11-imine,
1-chloro-3-fluoro-11H-pyrido[2,1-b]quinazolin-11-imine,
1-chloro-3-bromo-11H-pyrido[2,1-b]quinazolin-11-imine,
1-chloro-3-iodo-11H-pyrido[2,1-b]quinazolin-11-imine,
1-bromo-3-fluoro-11H-pyrido[2,1-b]quinazolin-11-imine,
1-bromo-3-chloro-11H-pyrido[2,1-b]quinazolin-11-imine,
1-bromo-3-iodo-11H-pyrido[2,1-b]quinazolin-11-imine,
1,3-dibromo-11H-pyrido[2,1-b]quinazolin-11-imine,
1-iodo-3-fluoro-11H-pyrido[2,1-b]quinazolin-11-imine,
1-iodo-3-chloro-11H-pyrido[2,1-b]quinazolin-11-imine,
1-iodo-3-bromo-11H-pyrido[2,1-b]quinazolin-11-imine,
1,3-diiodo-11H-pyrido[2,1-b]quinazolin-11-imine, or a pharmaceutically acceptable acid addition salt thereof.

A second preferred series of compounds of Formula I are those of Formula V

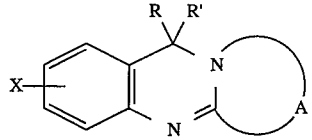

wherein A represents

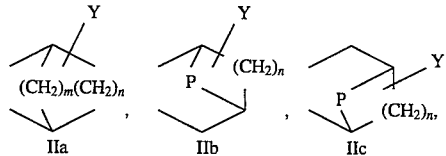

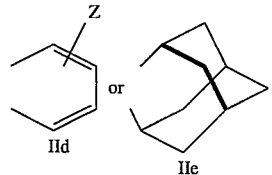

in which n is 1–10, P is a bond or $(CH_2)_m$ in which m is 0–3, wherein a nitrogen, oxygen, or sulfur atom may replace a methylene group ($CH_2$) in ring A, which methylene is not adjacent to the quinazoline moiety; attached to a carbon atom in ring A is Y, in which Y is hydrogen, hydroxy, carboxy, lower alkoxy, lower alkyl, aryl, heteroaryl, keto, lower alkoxycarbonyl, or lower alkanoyl including oxime derivatives of the alkanoyl compounds; R and R' are each independently hydrogen, hydroxy, lower alkyl, lower alkoxy, lower alkenyl, lower alkynyl, aryl, aryloxy, aryl lower alkyl, heteroaryl, or heteroaryl lower alkyl and, when taken together, may form a three- to six-membered ring optionally containing one to three heteroatoms selected from nitrogen, oxygen, and sulfur; and X is absent or one to four substituents selected from halogen, lower alkyl, perfluorinated lower alkyl, perfluorinated lower alkoxy, lower alkylthio, lower alkoxy, and alkyl($C_1$–$C_{12}$)carbamoyloxy; Z is as defined above; or a pharmaceutically acceptable salt thereof; with the provision that when A is of the Formula IId, X is 1,3-dihalogeno.

More preferred of the second series are compounds of Formula V wherein Y is hydrogen, hydroxy, carboxy, lower alkoxy, lower alkyl, aryl, heteroaryl, lower alkoxycarbonyl, or lower alkanoyl.

Most preferred of the second series are those of Formula V wherein Y is hydrogen, methyl or phenyl; n is 1 to 3, and m is 0 to 2, and X is one to four substituents selected from chloro, bromo, fluoro, iodo, methylthio, trifluoromethoxy, methyl, methoxy, methylcarbamoyloxy, heptylcarbamoyloxy, and trifluoromethyl.

Particularly valuable of the second series are:
1-methyl-6,7,8,9,10,12-hexahydroazepino[2,1-b]quinazoline,
2-methyl-6,7,8,9,10,12-hexahydroazepino[2,1-b]quinazoline,
3-methyl-6,7,8,9,10,12-hexahydroazepino[2,1-b]quinazoline,
4-methyl-6,7,8,9,10,12-hexahydroazepino[2,1-b]quinazoline,
1-chloro-6,7,8,9,10,12-hexahydroazepino[2,1-b]quinazoline,
2-chloro-6,7,8,9,10,12-hexahydroazepino[2,1-b]quinazoline,
3-chloro-6,7,8,9,10,12-hexahydroazepino[2,1-b]quinazoline,
4-chloro-6,7,8,9,10,12-hexahydroazepino[2,1-b]quinazoline,
1-fluoro-6,7,8,9,10,12-hexahydroazepino[2,1-b]quinazoline,
2-fluoro-6,7,8,9,10,12-hexahydroazepino[2,1-b]quinazoline,
3-fluoro-6,7,8,9,10,12-hexahydroazepino[2,1-b]quinazoline,
4-fluoro-6,7,8,9,10,12-hexahydroazepino[2,1-b]quinazoline,
1-bromo-6,7,8,9,10,12-hexahydroazepino[2,1-b]quinazoline,
2-bromo-6,7,8,9,10,12-hexahydroazepino[2,1-b]quinazoline,
3-bromo-6,7,8,9,10,12-hexahydroazepino[2,1-b]quinazoline,
4-bromo-6,7,8,9,10,12-hexahydroazepino[2,1-b]quinazoline,
1-(trifluoromethyl)-6,7,8,9,10,12-hexahydroazepino[2,1-b]quinazoline,
2-(trifluoromethyl)-6,7,8,9,10,12-hexahydroazepino[2,1-b]quinazoline, 3-(trifluoromethyl)-6,7,8,9,10,12-hexahydroazepino[2,1-b]quinazoline,
4-(trifluoromethyl)-6,7,8,9,10,12-hexahydroazepino[2,1-b]quinazoline,
1-(methylthio)-6,7,8,9,10,12-hexahydroazepino[2,1-b]quinazoline,
2-(methylthio)-6,7,8,9,10,12-hexahydroazepino[2,1-b]quinazoline,
3-(methylthio)-6,7,8,9,10,12-hexahydroazepino[2,1-b]quinazoline,
4-(methylthio)-6,7,8,9,10,12-hexahydroazepino[2,1-b]quinazoline,
1,2-dichloro-6,7,8,9,10,12-hexahydroazepino[2,1-b]quinazoline,
1,3-dichloro-6,7,8,9,10,12-hexahydroazepino[2,1-b]quinazoline,
1,4-dichloro-6,7,8,9,10,12-hexahydroazepino[2,1-b]quinazoline,
2,3-dichloro-6,7,8,9,10,12-hexahydroazepino[2,1-b]quinazoline,
2,4-dichloro-6,7,8,9,10,12-hexahydroazepino[2,1-b]quinazoline,
3,4-dichloro-6,7,8,9,10,12-hexahydroazepino[2,1-b]quinazoline,
3,4-dibromo-6,7,8,9,10,12-hexahydroazepino[2,1-b]quinazoline,
2,3-dimethoxy-6,7,8,9,10,12-hexahydroazepino[2,1-b]quinazoline,
2,4-dimethoxy-6,7,8,9,10,12-hexahydroazepino[2,1-b]quinazoline,
3,4-dimethoxy-6,7,8,9,10,12-hexahydroazepino[2,1-b]quinazoline,
1,2-dimethyl-6,7,8,9,10,12-hexahydroazepino[2,1-b]quinazoline,
1,3-dimethyl-6,7,8,9,10,12-hexahydroazepino[2,1-b]quinazoline,
1,4-dimethyl-6,7,8,9,10,12-hexahydroazepino[2,1-b]quinazoline,
2,3-dimethyl-6,7,8,9,10,12-hexahydroazepino[2,1-b]quinazoline,
2,4-dimethyl-6,7,8,9,10,12-hexahydroazepino[2,1-b]quinazoline,
3,4-dimethyl-6,7,8,9,10,12-hexahydroazepino2,1-b]quinazoline,
2-ethyl-6,7,8,9,10,12-hexahydroazepino[2,1-b]quinazoline,
2-(methylcarbamoyloxy)-6,7,8,9,10,12-hexahydroazepino[2,1-b]quinazoline,
1-chloro-2-(methylcarbamoyloxy)-6,7,8,9,10,12-hexahydroazepino[2,1-b]quinazoline,
3-chloro-2-(methylcarbamoyloxy)-6,7,8,9,10,12-hexahydroazepino[2,1-b]quinazoline,
1,3-dichloro-2-(methylcarbamoyloxy)-6,7,8,9,10,12-hexahydroazepino[2,1-b]quinazoline,
2-(heptylcarbamoyloxy)-6,7,8,9,10,12-hexahydroazepino[2,1-b]quinazoline,
1-chloro-2-(heptylcarbamoyloxy)-6,7,8,9,10,12-hexahydroazepino[2,1-b]quinazoline,
3-chloro-2-(heptylcarbamoyloxy)-6,7,8,9,10,12-hexahydroazepino[2,1-b]quinazoline,
1,3-dichloro-2-(heptylcarbamoyloxy)-6,7,8,9,10,12-hexahydroazepino[2,1-b]quinazoline,
1-chloro-2-methyl-6,7,8,9,10,12-hexahydroazepino[2,1-b]quinazoline,
1-chloro-3-methyl-6,7,8,9,10,12-hexahydroazepino[2,1-b]quinazoline,
1-chloro-4-methyl-6,7,8,9,10,12-hexahydroazepino[2,1-b]quinazoline,
2-chloro-1-methyl-6,7,8,9,10,12-hexahydroazepino[2,1-b]quinazoline,
3-chloro-1-methyl-6,7,8,9,10,12-hexahydroazepino[2,1-b]quinazoline,
4-chloro-1-methyl-6,7,8,9,10,12-hexahydroazepino[2,1-b]quinazoline,
3-chloro-1-methyl-6,7,8,9,10,12-hexahydroazepino[2,1-b]quinazoline,
3-chloro-2-methyl-6,7,8,9,10,12-hexahydroazepino[2,1-b]quinazoline,
3-chloro-4-methyl-6,7,8,9,10,12-hexahydroazepino[2,1-b]quinazoline,
4-chloro-1-methyl-6,7,8,9,10,12-hexahydroazepino[2,1-b]quinazoline,
4-chloro-2-methyl-6,7,8,9,10,12-hexahydroazepino[2,1-b]quinazoline,
4-chloro-3-methyl-6,7,8,9,10,12-hexahydroazepino[2,1-b]quinazoline,
3-chloro-2,4-dimethyl-6,7,8,9,10,12-hexahydroazepino[2,1-b]quinazoline,
1,3-dichloro-2-methyl-6,7,8,9,10,12-hexahydroazepino[2,1-b]quinazoline,
1,3-dichloro-4-methyl-6,7,8,9,10,12-hexahydroazepino[2,1-b]quinazoline,
1,3-dichloro-2,4-dimethyl-6,7,8,9,10,12-hexahydroazepino[2,1-b]quinazoline,
1-chloro-7,7-dimethyl-6,7,8,9,10,12-hexahydroazepino[2,1-b]quinazoline,
3-chloro-7,7-dimethyl-6,7,8,9,10,12-hexahydroazepino[2,1-b]quinazoline,
1-chloro-9,9-dimethyl-6,7,8,9,10,12-hexahydroazepino[2,1-b]quinazoline,
3-chloro-9,9-dimethyl-6,7,8,9,10,12-hexahydroazepino[2,1-b]quinazoline,
1-chloro-12,12-dimethyl-6,7,8,9,10,12-hexahydroazepino[2,1-b]quinazoline,
3-chloro-12,12-dimethyl-6,7,8,9,10,12-hexahydroazepino[2,1-b]quinazoline,
1,3-dichloro-7,7-dimethyl-6,7,8,9,10,12-hexahydroazepino[2,1-b]quinazoline,
1,3-dichloro-9,9-dimethyl-6,7,8,9,10,12-hexahydroazepino[2,1-b]quinazoline,
1,3-dichloro-12,12-dimethyl-6,7,8,9,10,12-hexahydroazepino[2,1-b]quinazoline,
1,3-dichloro-7,7,9,9-tetramethyl-6,7,8,9,10,12-hexahydroazepino[2,1-b]quinazoline,
1-chloro-7,7,9,9-tetramethyl-6,7,8,9,10,12-hexahydroazepino[2,1-b]quinazoline,
3-chloro-7,7,9,9-tetramethyl-6,7,8,9,10,12-hexahydroazepino[2,1-b]quinazoline,
1,3-dichloro-7,7,9,9,12,12-hexamethyl-6,7,8,9,10,12-hexahydroazepino[2,1-b]quinazoline,
3-chloro-12-methylene-6,7,8,9,10,12-hexahydroazepino[2,1-b]quinazoline,
3-chloro-12-isopropylidene-6,7,8,9,10,12-hexahydroazepino[2,1-b]quinazoline,
1,3-dichloro-12-methylene-6,7,8,9,10,12-hexahydroazepino[2,1-b]quinazoline,
8,10-dichloro-1,2,5,11-tetrahydro-4H-[1,4]thiazepino[5,4-b]quinazoline,
8-chloro-1,2,5,11-tetrahydro-4H-[1,4]thiazepino[5,4-b]quinazoline,
8,10-dichloro-1,2,5,11-tetrahydro-4H-[1,4]thiazepino[5,4-b]quinazoline-3,3-dioxide,
1,3-dichloro-8,9,10,12-tetrahydroazepino[2,1-b]quinazolin-7(6H)-one,
1,3-dichloro-8,9,10,12-tetrahydroazepino[2,1-b]quinazolin-8(6H)-one, 1,3-dichloro-8,9,10,12-tetrahydroazepino[2,1-b]quinazolin-9(6H)-one,
1-methyl-6,7,8,9-tetrahydro-11H-pyrido[2,1-b]quinazoline,
2-methyl-6,7,8,9-tetrahydro-11H-pyrido[2,1-b]quinazoline,
3-methyl-6,7,8,9-tetrahydro-11H-pyrido[2,1-b]quinazoline,
4-methyl-6,7,8,9-tetrahydro-11H-pyrido[2,1-b]quinazoline,
1-chloro-6,7,8,9-tetrahydro-11H-pyrido[2,1-b]quinazoline,
2-chloro-6,7,8,9-tetrahydro-11H-pyrido[2,1-b]quinazoline,
3-chloro-6,7,8,9-tetrahydro-11H-pyrido[2,1-b]quinazoline,
4-chloro-6,7,8,9-tetrahydro-11H-pyrido[2,1-b]quinazoline,
1-methoxy-6,7,8,9-tetrahydro-11H-pyrido[2,1-b]quinazoline,
2-methoxy-6,7,8,9-tetrahydro-11H-pyrido[2,1-b]quinazoline,
3-methoxy-6,7,8,9-tetrahydro-11H-pyrido[2,1-b]quinazoline,
4-methoxy-6,7,8,9-tetrahydro-11H-pyrido[2,1-b]quinazoline,
1-fluoro-6,7,8,9-tetrahydro-11H-pyrido[2,1-b]quinazoline,
2-fluoro-6,7,8,9-tetrahydro-11H-pyrido[2,1-b]quinazoline,
3-fluoro-6,7,8,9-tetrahydro-11H-pyrido[2,1-b]quinazoline,
4-fluoro-6,7,8,9-tetrahydro-11H-pyrido[2,1-b]quinazoline,
1-bromo-6,7,8,9-tetrahydro-11H-pyrido[2,1-b]quinazoline,
2-bromo-6,7,8,9-tetrahydro-11H-pyrido[2,1-b]quinazoline,
3-bromo-6,7,8,9-tetrahydro-11H-pyrido[2,1-b]quinazoline,
4-bromo-6,7,8,9-tetrahydro-11H-pyrido[2,1-b]quinazoline,
1-(trifluoromethyl)-6,7,8,9-tetrahydro-11H-pyrido[2,1-b]quinazoline,
2-(trifluoromethyl)-6,7,8,9-tetrahydro-11H-pyrido[2,1-b]quinazoline,
3-(trifluoromethyl)-6,7,8,9-tetrahydro-11H-pyrido[2,1-b]quinazoline,
4-(trifluoromethyl)-6,7,8,9-tetrahydro-11H-pyrido[2,1-b]quinazoline,
1-(methylthio)-6,7,8,9-tetrahydro-11H-pyrido[2,1-b]quinazoline,
2-(methylthio)-6,7,8,9-tetrahydro-11H-pyrido[2,1-b]quinazoline,
3-(methylthio)-6,7,8,9-tetrahydro-11H-pyrido[2,1-b]quinazoline,
4-(methylthio)-6,7,8,9-tetrahydro-11H-pyrido[2,1-b]quinazoline,
1,2-dichloro-6,7,8,9-tetrahydro-11H-pyrido[2,1-b]quinazoline,
1,3-dichloro-6,7,8,9-tetrahydro-11H-pyrido[2,1-b]quinazoline,
1,4-dichloro-6,7,8,9-tetrahydro-11H-pyrido[2,1-b]quinazoline,
2,3-dichloro-6,7,8,9-tetrahydro-11H-pyrido[2,1-b]quinazoline,
2,4-dichloro-6,7,8,9-tetrahydro-11H-pyrido[2,1-b]quinazoline,
3,4-dichloro-6,7,8,9-tetrahydro-11H-pyrido[2,1-b]quinazoline,
3,4-dibromo-6,7,8,9-tetrahydro-11H-pyrido[2,1-b]quinazoline,
2,3-dimethoxy-6,7,8,9-tetrahydro-11H-pyrido[2,1-b]quinazoline,
2,4-dimethoxy-6,7,8,9-tetrahydro-11H-pyrido[2,1-b]quinazoline,
3,4-dimethoxy-6,7,8,9-tetrahydro-11H-pyrido[2,1-b]quinazoline,
1,2-dimethyl-6,7,8,9-tetrahydro-11H-pyrido[2,1-b]quinazoline,
1,3-dimethyl-6,7,8,9-tetrahydro-11H-pyrido[2,1-b]quinazoline,
1,4-dimethyl-6,7,8,9-tetrahydro-11H-pyrido[2,1-b]quinazoline,
2,3-dimethyl-6,7,8,9-tetrahydro-11H-pyrido[2,1-b]quinazoline,
2,4-dimethyl-6,7,8,9-tetrahydro-11H-pyrido[2,1-b]quinazoline,
3,4-dimethyl-6,7,8,9-tetrahydro-11H-pyrido[2,1-b]quinazoline,
2-ethyl-6,7,8,9-tetrahydro-11H-pyrido[2,1-b]quinazoline,
2-(methylcarbamoyloxy)-6,7,8,9-tetrahydro-11H-pyrido[2,1-b]quinazoline,
1-chloro-2-(methylcarbamoyloxy)-6,7,8,9-tetrahydro-11H-pyrido[2,1-b]quinazoline,
3-chloro-2-(methylcarbamoyloxy)-6,7,8,9-tetrahydro-11H-pyrido[2,1-b]quinazoline,
1,3-dichloro-2-(methylcarbamoyloxy)-6,7,8,9-tetrahydro-11H-pyrido[2,1-b]quinazoline,
2-(heptylcarbamoyloxy)-6,7,8,9-tetrahydro-11H-pyrido[2,1-b]quinazoline,
1-chloro-2-(heptylcarbamoyloxy)-6,7,8,9-tetrahydro-11H-pyrido[2,1-b]quinazoline,
3-chloro-2-(heptylcarbamoyloxy)-6,7,8,9-tetrahydro-11H-pyrido[2,1-b]quinazoline,
1,3-dichloro-2-(heptylcarbamoyloxy)-6,7,8,9-tetrahydro-11H-pyrido[2,1-b]quinazoline,
1-chloro-2-methyl-6,7,8,9-tetrahydro-11H-pyrido[2,1-b]quinazoline,
1-chloro-3-methyl-6,7,8,9-tetrahydro-11H-pyrido[2,1-b]quinazoline,
1-chloro-4-methyl-6,7,8,9-tetrahydro-11H-pyrido[2,1-b]quinazoline,
2-chloro-1-methyl-6,7,8,9-tetrahydro-11H-pyrido[2,1-b]quinazoline,
3-chloro-1-methyl-6,7,8,9-tetrahydro-11H-pyrido[2,1-b]quinazoline,
4-chloro-1-methyl-6,7,8,9-tetrahydro-11H-pyrido[2,1-b]quinazoline,
3-chloro-1-methyl-6,7,8,9-tetrahydro-11H-pyrido[2,1-b]quinazoline,
3-chloro-2-methyl-6,7,8,9-tetrahydro-11H-pyrido[2,1-b]quinazoline,
3-chloro-2-methyl-6,7,8,9-tetrahydro-11H-pyrido[2,1-b]quinazoline,
3-chloro-4-methyl-6,7,8,9-tetrahydro-11H-pyrido[2,1-b]quinazoline,
4-chloro-1-methyl-6,7,8,9-tetrahydro-11H-pyrido[2,1-b]quinazoline,
4-chloro-2-methyl-6,7,8,9-tetrahydro-11H-pyrido[2,1-b]quinazoline,
3-chloro-2,4-dimethyl-6,7,8,9-tetrahydro-11H-pyrido[2,1-b]quinazoline,
1,3-dichloro-2-methyl-6,7,8,9-tetrahydro-11H-pyrido[2,1-b]quinazoline,
1,3-dichloro-4-methyl-6,7,8,9-tetrahydro-11H-pyrido[2,1-b]quinazoline,
1,3-dichloro-2,4-dimethyl-6,7,8,9-tetrahydro-11H-pyrido[2,1-b]quinazoline,
1,3-dichloro-7-thia-6,7,8,9-tetrahydro-11H-pyrido[2,1-b]quinazoline,
1,3-dichloro-7-oxa-6,7,8,9-tetrahydro-11H-pyrido[2,1-b]quinazoline,
1,3-dichloro-7-thia-6,7,8,9-tetrahydro-11H-pyrido[2,1-b]quinazoline-7,7-dioxide,
5-chloro-1,2,3,9-tetrahydropyrrolo[2,1-b]quinazoline,
6-chloro-1,2,3,9-tetrahydropyrrolo[2,1-b]quinazoline,
7-chloro-1,2,3,9-tetrahydropyrrolo[2,1-b]quinazoline,
8-chloro-1,2,3,9-tetrahydropyrrolo[2,1-b]quinazoline,
5-methyl-1,2,3,9-tetrahydropyrrolo[2,1-b]quinazoline,
6-methyl-1,2,3,9-tetrahydropyrrolo[2,1-b]quinazoline, 7-methyl-1,2,3,9-tetrahydropyrrolo[2,1-b]quinazoline,
8-methyl-1,2,3,9-tetrahydropyrrolo[2,1-b]quinazoline,
5,6-dichloro-1,2,3,9-tetrahydropyrrolo[2,1-b]quinazoline,
5,7-dichloro-1,2,3,9-tetrahydropyrrolo[2,1-b]quinazoline,
5,8-dichloro-1,2,3,9-tetrahydropyrrolo[2,1-b]quinazoline,
6,7-dichloro-1,2,3,9-tetrahydropyrrolo[2,1-b]quinazoline,
6,8-dichloro-1,2,3,9-tetrahydropyrrolo[2,1-b]quinazoline,
6,8-dichloro-1,2,3,9-tetrahydropyrrolo[2,1-b]quinazoline,
7,8-dichloro-1,2,3,9-tetrahydropyrrolo[2,1-b]quinazoline,
6-chloro-8-methyl-1,2,3,9-tetrahydropyrrolo[2,1-b]quinazoline,
8-chloro-6-methyl-1,2,3,9-tetrahydropyrrolo[2,1-b]quinazoline,
6,8-dichloro-9-methyl-1,2,3,9-tetrahydropyrrolo[2,1-b]quinazoline,
6,8-dichloro-9,9-dimethyl-1,2,3,9-tetrahydropyrrolo[2,1-b]quinazoline,
6-chloro-8,9-dimethyl-1,2,3,9-tetrahydropyrrolo[2,1-b]quinazoline,
8-chloro-6,9-dimethyl-1,2,3,9-tetrahydropyrrolo[2,1-b]quinazoline,
6-chloro-8,9,9-trimethyl-1,2,3,9-tetrahydropyrrolo[2,1-b]quinazoline,
8-chloro-6,9,9-trimethyl-1,2,3,9-tetrahydropyrrolo[2,1-b]quinazoline,
6-chloro-9-methylene-9(1H)-2,3-dihydropyrrolo[2,1-b]quinazoline,
6-chloro-9-isopropylidene-9(1H)-2,3-dihydropyrrolo[2,1-b]quinazoline,
5,6-dibromo-1,2,3,9-tetrahydropyrrolo[2,1-b]quinazoline,
5,7-dibromo-1,2,3,9-tetrahydropyrrolo[2,1-b]quinazoline,
5,8-dibromo-1,2,3,9-tetrahydropyrrolo[2,1-b]quinazoline,
6,7-dibromo-1,2,3,9-tetrahydropyrrolo[2,1-b]quinazoline,
6,8-dibromo-1,2,3,9-tetrahydropyrrolo[2,1-b]quinazoline,
7,8-dibromo-1,2,3,9-tetrahydropyrrolo[2,1-b]quinazoline,
2-phenyl-1,2,3,9-tetrahydropyrrolo[2,1-b]quinazoline,
2,2-diphenyl-1,2,3,9-tetrahydropyrrolo[2,1-b]quinazoline,
6-chloro-2-phenyl-1,2,3,9-tetrahydropyrrolo[2,1-b]quinazoline,
6,8-dichloro-2-phenyl-1,2,3,9-tetrahydropyrrolo[2,1-b]quinazoline,
8,8-diphenyl-6,7,8,9-tetrahydro-11H-pyrido[2,1-b]quinazoline,
1-chloro-8,8-diphenyl-6,7,8,9-tetrahydro-11H-pyrido[2,1-b]quinazoline,
3-chloro-8,8-diphenyl-6,7,8,9-tetrahydro-11H-pyrido[2,1-b]quinazoline,
1-chloro-8,8-diphenyl-7-oxa-6,7,8,9-tetrahydro-11H-pyrido[2,1-b]quinazoline,
3-chloro-8,8-diphenyl-7-oxa-6,7,8,9-tetrahydro-11H-pyrido[2,1-b]quinazoline,
8,8-diphenyl-7-oxa-6,7,8,9-tetrahydro-11H-pyrido[2,1-b]quinazoline,
1,3-dichloro-8,8-diphenyl-6,7,8,9-tetrahydro-11H-pyrido[2,1-b]quinazoline,
1,3-dichloro-8,8-diphenyl-7-oxa-6,7,8,9-tetrahydro-11H-pyrido[2,1-b]quinazoline,
8,8-diphenyl-6,7,8,9,10,12-hexahydroazepino[2,1-b]quinazoline,
1-chloro-8,8-diphenyl-6,7,8,9,10,12-hexahydroazepino[2,1-b]quinazoline,
3-chloro-8,8-diphenyl-6,7,8,9,10,12-hexahydroazepino[2,1-b]quinazoline,
1,3-dichloro-8,8-diphenyl-6,7,8,9,10,12-hexahydroazepino[2,1-b]quinazoline,
1,3-dichloro-6,7,8,9-tetrahydro-11H-6,9-methanopyrido[2,1-b]quinazoline,
1,3-dichloro-6,7,8,9,10,12-hexahydro-6,10-methanoazepino[2,1-b]quinazoline,
1,3-dichloro-6,7,8,9,10,12-hexahydro-6,9-methanoazepino[2,1-b]quinazoline,
1,3-dichloro-6,7,8,9,10,12-hexahydro-7,10-methanoazepino[2,1-b]quinazoline,
3-chloro-6,7,8,9,10,12-hexahydro-7,10-methanoazepino[2,1-b]quinazoline,
2-chloro-1,4-dimethyl-6,7,8,9,10,12-hexahydroazepino[2,1-b]quinazoline,
3-chloro-1,4-dimethyl-6,7,8,9,10,12-hexahydroazepino[2,1-b]quinazoline,
1-chloro-2,3-dimethyl-6,7,8,9,10,12-hexahydroazepino[2,1-b]quinazoline,
1-chloro-3,4-dimethyl-6,7,8,9,10,12-hexahydroazepino[2,1-b]quinazoline,
1-chloro-2,4-dimethyl-6,7,8,9,10,12-hexahydroazepino[2,1-b]quinazoline,
2-chloro-3,4-dimethyl-6,7,8,9,10,12-hexahydroazepino[2,1-b]quinazoline,
2-chloro-1,3-dimethyl-6,7,8,9,10,12-hexahydroazepino[2,1-b]quinazoline,
3-chloro-1,2-dimethyl-6,7,8,9,10,12-hexahydroazepino[2,1-b]quinazoline,
3-chloro-2,4-dimethyl-6,7,8,9,10,12-hexahydroazepino[2,1-b]quinazoline,
4-chloro-1,2-dimethyl-6,7,8,9,10,12-hexahydroazepino[2,1-b]quinazoline,
4-chloro-1,3-dimethyl-6,7,8,9,10,12-hexahydroazepino[2,1-b]quinazoline,
4-chloro-2,3-dimethyl-6,7,8,9,10,12-hexahydroazepino[2,1-b]quinazoline,
1,3-dichloro-2,4-dimethyl-6,7,8,9,10,12-hexahydroazepino[2,1-b]quinazoline,
1,2-dichloro-3,4-dimethyl-6,7,8,9,10,12-hexahydroazepino[2,1-b]quinazoline,
2,3-dichloro-1,4-dimethyl-6,7,8,9,10,12-hexahydroazepino[2,1-b]quinazoline,
2,4-dichloro-1,3-dimethyl-6,7,8,9,10,12-hexahydroazepino[2,1-b]quinazoline,
1,4-dichloro-2,3-dimethyl-6,7,8,9,10,12-hexahydroazepino[2,1-b]quinazoline,
3,4-dichloro-1,2-dimethyl-6,7,8,9,10,12-hexahydroazepino[2,1-b]quinazoline,
2-chloro-1,4-dimethoxy-6,7,8,9,10,12-hexahydroazepino[2,1-b]quinazoline,
3-chloro-1,4-dimethoxy-6,7,8,9,10,12-hexahydroazepino[2,1-b]quinazoline,
1-chloro-2,3-dimethoxy-6,7,8,9,10,12-hexahydroazepino[2,1-b]quinazoline,
1-chloro-3,4-dimethoxy-6,7,8,9,10,12-hexahydroazepino[2,1-b]quinazoline,
1-chloro-2,4-dimethoxy-6,7,8,9,10,12-hexahydroazepino[2,1-b]quinazoline,
2-chloro-3,4-dimethoxy-6,7,8,9,10,12-hexahydroazepino[2,1-b]quinazoline,
2-chloro-1,3-dimethoxy-6,7,8,9,10,12-hexahydroazepino[2,1-b]quinazoline,
3-chloro-1,2-dimethoxy-6,7,8,9,10,12-hexahydroazepino[2,1-b]quinazoline,
3-chloro-2,4-dimethoxy-6,7,8,9,10,12-hexahydroazepino[2,1-b]quinazoline,
4-chloro-1,2-dimethoxy-6,7,8,9,10,12-hexahydroazepino[2,1-b]quinazoline,
4-chloro-1,3-dimethoxy-6,7,8,9,10,12-hexahydroazepino[2,1-b]quinazoline,
4-chloro-2,3-dimethoxy-6,7,8,9,10,12-hexahydroazepino[2,1-b]quinazoline, 1,3-dichloro-2,4-dimethoxy-6,7,8,9,10,12-hexahydroazepino[2,1-b]quinazoline,
1,2-dichloro-3,4-dimethoxy-6,7,8,9,10,12-hexahydroazepino[2,1-b]quinazoline,
2,3-dichloro-1,4-dimethoxy-6,7,8,9,10,12-hexahydroazepino[2,1-b]quinazoline,
2,4-dichloro-1,3-dimethoxy-6,7,8,9,10,12-hexahydroazepino[2,1-b]quinazoline,
1,4-dichloro-2,3-dimethoxy-6,7,8,9,10,12-hexahydroazepino[2,1-b]quinazoline,
3,4-dichloro-1,2-dimethoxy-6,7,8,9,10,12-hexahydroazepino[2,1-b]quinazoline,
1,3-dichloro-2-methylthio-4-methyl-6,7,8,9,10,12-hexahydroazepino[2,1-b]quinazoline,
2,4-dichloro-3-methylthio-4-methyl-6,7,8,9,10,12-hexahydroazepino[2,1-b]quinazoline,
1-chloro-3-trifluoromethoxy-6,7,8,9,10,12-hexahydroazepino[2,1-b]quinazoline,
1-chloro-3-trifluoromethoxy-4-methyl-6,7,8,9,10,12-hexahydroazepino[2,1-b]quinazoline,
2-chloro-4-trifluoromethoxy-6,7,8,9,10,12-hexahydroazepino[2,1-b]quinazoline,
3-chloro-1-trifluoromethoxy-6,7,8,9,10,12-hexahydroazepino[2,1-b]quinazoline,
1,3-bis(trifluoromethoxy-6,7,8,9,10,12-hexahydroazepino[2,1-b]quinazoline,
2,4-bis(trifluoromethoxy-6,7,8,9,10,12-hexahydroazepino[2,1-b]quinazoline,
1-chloro-2,3-dimethoxy-4-methyl-6,7,8,9,10,12-hexahydroazepino[2,1-b]quinazoline,
1,2-dimethyl-3-chloro-4-methoxy-6,7,8,9,10,12-hexahydroazepino[2,1-b]quinazoline,
1,3-dichloro-2-fluoro-6,7,8,9,10,12-hexahydroazepino[2,1-b]quinazoline,
1-bromo-3-chloro-6,7,8,9,10,12-hexahydroazepino[2,1-b]quinazoline,
1-bromo-3-trifluoromethoxy-6,7,8,9,10,12-hexahydroazepino[2,1-b]quinazoline,
3-bromo-1-chloro-6,7,8,9,10,12-hexahydroazepino[2,1-b]quinazoline,
3-bromo-1-trifluoromethoxy-6,7,8,9,10,12-hexahydroazepino[2,1-b]quinazoline,
1,3-dibromo-6,7,8,9,10,12-hexahydroazepino[2,1-b]quinazoline, and
2,4-dibromo-6,7,8,9,10,12-hexahydroazepino[2,1-b]quinazoline,
1-fluoro-3-chloro-6,7,8,9,10,12-hexahydroazepino[2,1-b]quinazoline,
1-fluoro-3-bromo-6,7,8,9,10,12-hexahydroazepino[2,1-b]quinazoline,
1-fluoro-3-iodo-6,7,8,9,10,12-hexahydroazepino[2,1-b]quinazoline,
1-chloro-3-fluoro-6,7,8,9,10,12-hexahydroazepino[2,1-b]quinazoline,
1-chloro-3-bromo-6,7,8,9,10,12-hexahydroazepino[2,1-b]quinazoline,
1-chloro-3-iodo-6,7,8,9,10,12-hexahydroazepino[2,1-b]quinazoline,
1-bromo-3-fluoro-6,7,8,9,10,12-hexahydroazepino[2,1-b]quinazoline,
1-bromo-3-chloro-6,7,8,9,10,12-hexahydroazepino[2,1-b]quinazoline,
1-bromo-3-iodo-6,7,8,9,10,12-hexahydroazepino[2,1-b]quinazoline,
1-iodo-3-fluoro-6,7,8,9,10,12-hexahydroazepine[2,1-b]quinazoline,
1-iodo-3-chloro-6,7,8,9,10,12-hexahydroazepine[2,1-b]quinazoline,
1-iodo-3-bromo-6,7,8,9,10,12-hexahydroazepine[2,1-b]quinazoline,
1,3-diiodo-6,7,8,9,10,12-hexahydroazepine[2,1-b]quinazoline,
1,3-dichloro-6,7,8,9,10,12-hexahydroazepino[2,1-b]quinazolin-12-ol,
1-fluoro-3-chloro-6,7,8,9-tetrahydro-11H-pyrido[2,1-b]quinazoline,
1-fluoro-3-bromo-6,7,8,9-tetrahydro-11H-pyrido[2,1-b]quinazoline,
1-fluoro-3-iodo-6,7,8,9-tetrahydro-11H-pyrido[2,1-b]quinazoline,
1-chloro-3-fluoro-6,7,8,9-tetrahydro-11H-pyrido[2,1-b]quinazoline,
1-chloro-3-bromo-6,7,8,9-tetrahydro-11H-pyrido[2,1-b]quinazoline,
1-chloro-3-iodo-6,7,8,9-tetrahydro-11H-pyrido[2,1-b]quinazoline,
1-bromo-3-fluoro-6,7,8,9-tetrahydro-11H-pyrido[2,1-b]quinazoline,
1-bromo-3-chloro-6,7,8,9-tetrahydro-11H-pyrido[2,1-b]quinazoline,
1-bromo-3-iodo-6,7,8,9-tetrahydro-11H-pyrido[2,1-b]quinazoline,
1-iodo-3-fluoro-6,7,8,9-tetrahydro-11H-pyrido[2,1-b]quinazoline,
1-iodo-3-chloro-6,7,8,9-tetrahydro-11H-pyrido[2,1-b]quinazoline,
1-iodo-3-bromo-6,7,8,9-tetrahydro-11H-pyrido[2,1-b]quinazoline,
1,3-diiodo-6,7,8,9-tetrahydro-11H-pyrido[2,1-b]quinazoline,
6,8-difluoro-1,2,3-tetrahydropyrrolo[2,1-b]quinazoline,
6-fluoro-8-chloro-1,2,3,9-tetrahydropyrrolo[2,1-b]quinazoline,
6-fluoro-8-bromo-1,2,3,9-tetrahydropyrrolo[2,1-b]quinazoline,
6-fluoro-8-iodo-1,2,3,9-tetrahydropyrrolo[2,1-b]quinazoline,
6-chloro-8-fluoro-1,2,3,9-tetrahydropyrrolo[2,1-b]quinazoline,
6-chloro-8-bromo-1,2,3,9-tetrahydropyrrolo[2,1-b]quinazoline,
6-chloro-8-iodo-1,2,3,9-tetrahydropyrrolo[2,1-b]quinazoline,
6-bromo-8-fluoro-1,2,3,9-tetrahydropyrrolo[2,1-b]quinazoline,
6-bromo-8-chloro-1,2,3,9-tetrahydropyrrolo[2,1-b]quinazoline,
6-bromo-8-iodo-1,2,3,9-tetrahydropyrrolo[2,1-b]quinazoline,
6,8-dibromo-1,2,3,9-tetrahydropyrrolo[2,1-b]quinazoline,
6-iodo-8-fluoro-1,2,3,9-tetrahydropyrrolo[2,1-b]quinazoline,
6-iodo-8-chloro-1,2,3,9-tetrahydropyrrolo[2,1-b]quinazoline,
6-iodo-8-bromo-1,2,3,9-tetrahydropyrrolo[2,1-b]quinazoline,
6,8-diiodo-1,2,3,9-tetrahydropyrrolo[2,1-b]quinazoline,
1-methyl-6,7,8,9-tetrahydro-11H-6,9-methanopyrido[2,1-b]quinazoline,
2-methyl-6,7,8,9-tetrahydro-11H-6,9-methanopyrido[2,1-b]quinazoline,
3-methyl-6,7,8,9-tetrahydro-11H-6,9-methanopyrido[2,1-b]quinazoline,
4-methyl-6,7,8,9-tetrahydro-11H-6,9-methanopyrido[2,1-b]quinazoline, 1-chloro-6,7,8,9-tetrahydro-11H-6,9-methanopyrido[2,1-b]quinazoline,
2-chloro-6,7,8,9-tetrahydro-11H-6,9-methanopyrido[2,1-b]quinazoline,
3-chloro-6,7,8,9-tetrahydro-11H-6,9-methanopyrido[2,1-b]quinazoline,
4-chloro-6,7,8,9-tetrahydro-11H-6,9-methanopyrido[2,1-b]quinazoline,
1-fluoro-6,7,8,9-tetrahydro-11H-6,8-methanopyrido[2,1-b]quinazoline,
2-fluoro-6,7,8,9-tetrahydro-11H-6,8-methanopyrido[2,1-b]quinazoline,
3-fluoro-6,7,8,9-tetrahydro-11H-6,8-methanopyrido[2,1-b]quinazoline,
4-fluoro-6,7,8,9-tetrahydro-11H-6,8-methanopyrido[2,1-b]quinazoline,
1-bromo-6,7,8,9-tetrahydro-11H-6,8-methanopyrido[2,1-b]quinazoline,
2-bromo-6,7,8,9-tetrahydro-11H-6,8-methanopyrido[2,1-b]quinazoline,
3-bromo-6,7,8,9-tetrahydro-11H-6,8-methanopyrido[2,1-b]quinazoline,
4-bromo-6,7,8,9-tetrahydro-11H-6,8-methanopyrido[2,1-b]quinazoline,
1-(trifluoromethyl)-6,7,8,9-tetrahydro-11H-6,9-methanopyrido[2,1-b]quinazoline,
2-(trifluoromethyl)-6,7,8,9-tetrahydro-11H-6,9-methanopyrido[2,1-b]quinazoline,
3-(trifluoromethyl)-6,7,8,9-tetrahydro-11H-6,9-methanopyrido[2,1-b]quinazoline,
4-(trifluoromethyl)-6,7,8,9-tetrahydro-11H-6,9-methanopyrido[2,1-b]quinazoline,
1-(methylthio)-6,7,8,9-tetrahydro-11H-6,9-methanopyrido[2,1-b]quinazoline,
2-(methylthio)-6,7,8,9-tetrahydro-11H-6,9-methanopyrido[2,1-b]quinazoline,
3-(methylthio)-6,7,8,9-tetrahydro-11H-6,9-methanopyrido[2,1-b]quinazoline,
4-(methylthio)-6,7,8,9-tetrahydro-11H-6,9-methanopyrido[2,1-b]quinazoline,
1,2-dichloro-6,7,8,9-tetrahydro-11H-6,9-methanopyrido[2,1-b]quinazoline,
1,3-dichloro-6,7,8,9-tetrahydro-11H-6,9-methanopyrido[2,1-b]quinazoline,
1,4-dichloro-6,7,8,9-tetrahydro-11H-6,9-methanopyrido[2,1-b]quinazoline,
2,3-dichloro-6,7,8,9-tetrahydro-11H-6,9-methanopyrido[2,1-b]quinazoline,
2,4-dichloro-6,7,8,9-tetrahydro-11H-6,9-methanopyrido[2,1-b]quinazoline,
3,4-dichloro-6,7,8,9-tetrahydro-11H-6,9-methanopyrido[2,1-b]quinazoline,
1,3-dimethoxy-6,7,8,9-tetrahydro-11H-6,9-methanopyrido[2,1-b]quinazoline,
2,3-dimethoxy-6,7,8,9-tetrahydro-11H-6,9-methanopyrido[2,1-b]quinazoline,
2,4-dimethoxy-6,7,8,9-tetrahydro-11H-6,9-methanopyrido[2,1-b]quinazoline,
3,4-dimethoxy-6,7,8,9-tetrahydro-11H-6,9-methanopyrido[2,1-b]quinazoline,
1,2-dimethyl-6,7,8,9-tetrahydro-11H-6,9-methanopyrido[2,1-b]quinazoline,
1,3-dimethyl-6,7,8,9-tetrahydro-11H-6,9-methanopyrido[2,1-b]quinazoline,
1,4-dimethyl-6,7,8,9-tetrahydro-11H-6,9-methanopyrido[2,1-b]quinazoline,
2,3-dimethyl-6,7,8,9-tetrahydro-11H-6,9-methanopyrido[2,1-b]quinazoline,
2,4-dimethyl-6,7,8,9-tetrahydro-11H-6,9-methanopyrido[2,1-b]quinazoline,
3,4-dimethyl-6,7,8,9-tetrahydro-11H-6,9-methanopyrido[2,1-b]quinazoline,
2-(methylcarbamoyloxy)-6,7,8,9-tetrahydro-11H-6,9-methanopyrido[2,1-b]quinazoline,
1-chloro-2-(methylcarbamoyloxy)-6,7,8,9-tetrahydro-11H-6,9-methanopyrido[2,1-b]quinazoline,
3-chloro-2-(methylcarbamoyloxy)-6,7,8,9-tetrahydro-11H-6,9-methanopyrido[2,1-b]quinazoline,
1-chloro-3-(methylcarbamoyloxy)-6,7,8,9-tetrahydro-11H-6,9-methanopyrido[2,1-b]quinazoline,
2-(heptylcarbamoyloxy)-6,7,8,9-tetrahydro-11H-6,9-methanopyrido[2,1-b]quinazoline,
3-(heptylcarbamoyloxy)-6,7,8,9-tetrahydro-11H-6,9-methanopyrido[2,1-b]quinazoline,
1-chloro-3-(heptylcarbamoyloxy)-6,7,8,9-tetrahydro-11H-6,9-methanopyrido[2,1-b]quinazoline,
3-chloro-2-(heptylcarbamoyloxy)-6,7,8,9-tetrahydro-11H-6,9-methanopyrido[2,1-b]quinazoline,
1,3-dichloro-2-(heptylcarbamoyloxy)-6,7,8,9-tetrahydro-11H-6,9-methanopyrido[2,1-b] quinazoline,
1-chloro-2-methyl-6,7,8,9-tetrahydro-11H-6,9-methanopyrido[2,1-b]quinazoline,
1-chloro-3-methyl-6,7,8,9-tetrahydro-11H-6,9-methanopyrido[2,1-b]quinazoline,
1-chloro-4-methyl-6,7,8,9-tetrahydro-11H-6,9-methanopyrido[2,1-b]quinazoline,
2-chloro-1-methyl-6,7,8,9-tetrahydro-11H-6,9-methanopyrido[2,1-b]quinazoline,
3-chloro-1-methyl-6,7,8,9-tetrahydro-11H-6,9-methanopyrido[2,1-b]quinazoline,
4-chloro-1-methyl-6,7,8,9-tetrahydro-11H-6,9-methanopyrido[2,1-b]quinazoline,
3-chloro-1-methyl-6,7,8,9-tetrahydro-11H-6,9-methanopyrido[2,1-b]quinazoline,
3-chloro-2-methyl-6,7,8,9-tetrahydro-11H-6,9-methanopyrido[2,1-b]quinazoline,
3-chloro-4-methyl-6,7,8,9-tetrahydro-11H-6,9-methanopyrido[2,1-b]quinazoline,
4-chloro-1-methyl-6,7,8,9-tetrahydro-11H-6,9-methanopyrido[2,1-b]quinazoline,
4-chloro-2-methyl-6,7,8,9-tetrahydro-11H-6,9-methanopyrido[2,1-b]quinazoline,
1-methyl-3-chloro-6,7,8,9-tetrahydro-11H-6,9-methanopyrido[2,1-b]quinazoline,
3-chloro-1,4-dimethyl-6,7,8,9-tetrahydro-11H-6,9-methanopyrido[2,1-b]quinazoline,
1-chloro-3-methyl-6,7,8,9-tetrahydro-11H-6,9-methanopyrido[2,1-b]quinazoline,
1-methyl-3-chloro-6,7,8,9-tetrahydro-11H-6,9-methanopyrido[2,1-b]quinazoline,
1,3-dichloro-2-methyl-6,7,8,9-tetrahydro-11H-6,9-methanopyrido[2,1-b]quinazoline,
1,3-dichloro-4-methyl-6,7,8,9-tetrahydro-11H-6,9-methanopyrido[2,1-b]quinazoline,
1,3-dichloro-2,4-dimethyl-6,7,8,9-tetrahydro-11H-6,9-methanopyrido[2,1-b]quinazoline,
1-chloro-11,11-dimethyl-6,7,8,9-tetrahydro-11H-6,9-methanopyrido[2,1-b]quinazoline,
3-chloro-11,11-dimethyl-6,7,8,9-tetrahydro-11H-6,9-methanopyrido[2,1-b]quinazoline,
1,3-dichloro-11-methyl-6,7,8,9-tetrahydro-11H-6,9-methanopyrido[2,1-b]quinazoline,
1,3-dichloro-11,11-dimethyl-6,7,8,9-tetrahydro-11H-6,9-methanopyrido[2,1-b]quinazoline,
3-chloro-11,11-methylene-6,7,8,9-tetrahydro-11H-6,9-methanopyrido[2,1-b]quinazoline, 1,3-dichloro-11-isopropylidene-6,7,8,9-tetrahydro-11H-6,9-methanopyrido[2,1-b]quinazoline,
1,3-dichloro-11-methylene-6,7,8,9-tetrahydro-11H-6,9-methanopyrido[2,1-b]quinazoline,
1,3-difluoro-6,7,8,9-tetrahydro-11H-6,9-methanopyrido[2,1-b]quinazoline,
1-fluoro-3-bromo-6,7,8,9-tetrahydro-11H-6,9-methanopyrido[2,1-b]quinazoline,
1-fluoro-3-iodo-6,7,8,9-tetrahydro-11H-6,9-methanopyrido[2,1-b]quinazoline,
1-chloro-3-fluoro-6,7,8,9-tetrahydro-11H-6,9-methanopyrido[2,1-b]quinazoline,
1-chloro-3-bromo-6,7,8,9-tetrahydro-11H-6,9-methanopyrido[2,1-b]quinazoline,
1-chloro-3-iodo-6,7,8,9-tetrahydro-11H-6,9-methanopyrido[2,1-b]quinazoline,
1-bromo-3-fluoro-6,7,8,9-tetrahydro-11H-6,9-methanopyrido[2,1-b]quinazoline,
1-bromo-3-chloro-6,7,8,9-tetrahydro-11H-6,9-methanopyrido[2,1-b]quinazoline,
1-bromo-3-iodo-6,7,8,9-tetrahydro-11H-6,9-methanopyrido[2,1-b]quinazoline,
1,3-dibromo-6,7,8,9-tetrahydro-11H-6,9-methanopyrido[2,1-b]quinazoline,
1-iodo-3-fluoro-6,7,8,9-tetrahydro-11H-6,9-methanopyrido[2,1-b]quinazoline,
1-iodo-3-chloro-6,7,8,9-tetrahydro-11H-6,9-methanopyrido[2,1-b]quinazoline,
1-iodo-3-bromo-6,7,8,9-tetrahydro-11H-6,9-methanopyrido[2,1-b]quinazoline,
1,3-diiodo-6,7,8,9-tetrahydro-11H-6,9-methanopyrido[2,1-b]quinazoline,
1-methyl-6,9-dihydro-11H-6,9-methanopyrido[2,1-b]quinazoline,
2-methyl-6,9-dihydro-11H-6,9-methanopyrido[2,1-b]quinazoline,
3-methyl-6,9-dihydro-11H-6,9-methanopyrido[2,1-b]quinazoline,
4-methyl-6,9-dihydro-11H-6,9-methanopyrido[2,1-b]quinazoline,
1-chloro-6,9-dihydro-11H-6,9-methanopyrido[2,1-b]quinazoline,
2-chloro-6,9-dihydro-11H-6,9-methanopyrido[2,1-b]quinazoline,
3-chloro-6,9-dihydro-11H-6,9-methanopyrido[2,1-b]quinazoline,
4-chloro-6,9-dihydro-11H-6,9-methanopyrido[2,1-b]quinazoline,
1-fluoro-6,9-dihydro-11H-6,9-methanopyrido[2,1-b]quinazoline,
2-fluoro-6,9-dihydro-11H-6,9-methanopyrido[2,1-b]quinazoline,
3-fluoro-6,9-dihydro-11H-6,9-methanopyrido[2,1-b]quinazoline,
4-fluoro-6,9-dihydro-11H-6,9-methanopyrido[2,1-b]quinazoline,
1-bromo-6,9-dihydro-11H-6,9-methanopyrido[2,1-b]quinazoline,
2-bromo-6,9-dihydro-11H-6,9-methanopyrido[2,1-b]quinazoline,
3-bromo-6,9-dihydro-11H-6,9-methanopyrido[2,1-b]quinazoline,
4-bromo-6,9-dihydro-11H-6,9-methanopyrido[2,1-b]quinazoline,
1-(trifluoromethyl)-6,9-dihydro-11H-6,9-methanopyrido[2,1-b]quinazoline,
2-(trifluoromethyl)-6,9-dihydro-11H-6,9-methanopyrido[2,1-b]quinazoline,
3-(trifluoromethyl)-6,9-dihydro-11H-6,9-methanopyrido[2,1-b]quinazoline,
4-(trifluoromethyl)-6,9-dihydro-11H-6,9-methanopyrido[2,1-b]quinazoline,
1-(methylthio)-6,9-dihydro-11H-6,9-methanopyrido[2,1-b]quinazoline,
2-(methylthio)-6,9-dihydro-11H-6,9-methanopyrido[2,1-b]quinazoline,
3-(methylthio)-6,9-dihydro-11H-6,9-methanopyrido[2,1-b]quinazoline,
4-(methylthio)-6,9-dihydro-11H-6,9-methanopyrido[2,1-b]quinazoline,
1,2-dichloro-6,9-dihydro-11H-6,9-methanopyrido[2,1-b]quinazoline,
1,3-dichloro-6,9-dihydro-11H-6,9-methanopyrido[2,1-b]quinazoline,
1,4-dichloro-6,9-dihydro-11H-6,9-methanopyrido[2,1-b]quinazoline,
2,3-dichloro-6,9-dihydro-11H-6,9-methanopyrido[2,1-b]quinazoline,
2,4-dichloro-6,9-dihydro-11H-6,9-methanopyrido[2,1-b]quinazoline,
3,4-dichloro-6,9-dihydro-11H-6,9-methanopyrido[2,1-b]quinazoline,
1,3-dimethoxy-6,9-dihydro-11H-6,9-methanopyrido[2,1-b]quinazoline,
2,3-dimethoxy-6,9-dihydro-11H-6,9-methanopyrido[2,1-b]quinazoline,
2,4-dimethoxy-6,9-dihydro-11H-6,9-methanopyrido[2,1-b]quinazoline,
3,4-dimethoxy-6,9-dihydro-11H-6,9-methanopyrido[2,1-b]quinazoline,
1,2-dimethyl-6,9-dihydro-11H-6,9-methanopyrido[2,1-b]quinazoline,
1,3-dimethyl-6,9-dihydro-11H-6,9-methanopyrido[2,1-b]quinazoline,
1,4-dimethyl-6,9-dihydro-11H-6,9-methanopyrido[2,1-b]quinazoline,
2,3-dimethyl-6,9-dihydro-11H-6,9-methanopyrido[2,1-b]quinazoline,
2,4-dimethyl-6,9-dihydro-11H-6,9-methanopyrido[2,1-b]quinazoline,
3,4-dimethyl-6,9-dihydro-11H-6,9-methanopyrido[2,1-b]quinazoline,
2-(methylcarbamoyloxy)-6,9-dihydro-11H-6,9-methanopyrido[2,1-b]quinazoline,
1-chloro-2-(methylcarbamoyloxy)-6,9-dihydro-11H-6,9-methanopyrido[2,1-b]quinazoline,
3-chloro-2-(methylcarbamoyloxy)-6,9-dihydro-11H-6,9-methanopyrido[2,1-b]quinazoline,
1-chloro-3-(methylcarbamoyloxy)-6,9-dihydro-11H-6,9-methanopyrido[2,1-b]quinazoline,
2-(heptylcarbamoyloxy)-6,9-dihydro-11H-6,9-methanopyrido[2,1-b]quinazoline,
3-(heptylcarbamoyloxy)-6,9-dihydro-11H-6,9-methanopyrido[2,1-b]quinazoline,
1-chloro-3-(heptylcarbamoyloxy)-6,9-dihydro-11H-6,9-methanopyrido[2,1-b]quinazoline,
3-chloro-2-(heptylcarbamoyloxy)-6,9-dihydro-11H-6,9-methanopyrido[2,1-b]quinazoline,
1,3-dichloro-2-(heptylcarbamoyloxy)-6,9-dihydro-11H-6,9-methanopyrido[2,1-b]quinazoline,
1-chloro-2-methyl-6,9-dihydro-11H-6,9-methanopyrido[2,1-b]quinazoline,
1-chloro-3-methyl-6,9-dihydro-11H-6,9-methanopyrido[2,1-b]quinazoline,
1-chloro-4-methyl-6,9-dihydro-11H-6,9-methanopyrido[2,1-b]quinazoline, 2-chloro-1-methyl-6,9-dihydro-11H-6,9-methanopyrido[2,1-b]quinazoline,
3-chloro-1-methyl-6,9-dihydro-11H-6,9-methanopyrido[2,1-b]quinazoline,
4-chloro-1-methyl-6,9-dihydro-11H-6,9-methanopyrido[2,1-b]quinazoline,
3-chloro-1-methyl-6,9-dihydro-11H-6,9-methanopyrido[2,1-b]quinazoline,
3-chloro-2-methyl-6,9-dihydro-11H-6,9-methanopyrido[2,1-b]quinazoline,
3-chloro-4-methyl-6,9-dihydro-11H-6,9-methanopyrido[2,1-b]quinazoline,
4-chloro-1-methyl-6,9-dihydro-11H-6,9-methanopyrido[2,1-b]quinazoline,
4-chloro-2-methyl-6,9-dihydro-11H-6,9-methanopyrido[2,1-b]quinazoline,
1-methyl-3-chloro-6,9-dihydro-11H-6,9-methanopyrido[2,1-b]quinazoline,
3-chloro-1,4-dimethyl-6,9-dihydro-11H-6,9-methanopyrido[2,1-b]quinazoline,
1-chloro-3-methyl-6,9-dihydro-11H-6,9-methanopyrido[2,1-b]quinazoline,
1-methyl-3-chloro-6,9-dihydro-11H-6,9-methanopyrido[2,1-b]quinazoline,
1,3-dichloro-2-methyl-6,9-dihydro-11H-6,9-methanopyrido[2,1-b]quinazoline,
1,3-dichloro-4-methyl-6,9-dihydro-11H-6,9-methanopyrido[2,1-b]quinazoline,
1,3-dichloro-2,4-dimethyl-6,9-dihydro-11H-6,9-methanopyrido[2,1-b]quinazoline,
1-chloro-11,11-dimethyl-6,9-dihydro-11H-6,9-methanopyrido[2,1-b]quinazoline,
3-chloro-11,11-dimethyl-6,9-dihydro-11H-6,9-methanopyrido[2,1-b]quinazoline,
1,3-dichloro-11-methyl-6,9-dihydro-11H-6,9-methanopyrido[2,1-b]quinazoline,
1,3-dichloro-11,11-dimethyl-6,9-dihydro-11H-6,9-methanopyrido[2,1-b]quinazoline,
3-chloro-11-methylene-6,9-dihydro-11H-6,9-methanopyrido[2,1-b]quinazoline,
1,3-dichloro-11-isopropylidene-6,9-dihydro-11H-6,9-methanopyrido[2,1-b]quinazoline,
1,3-dichloro-11-methylene-6,9-dihydro-11H-6,9-methanopyrido[2,1-b]quinazoline,
1,3-dichloro-6,9-dihydro-11H-6,9-methanopyrido[2,1-b]quinazoline,
1-fluoro-3-bromo-6,9-dihydro-11H-6,9-methanopyrido[2,1-b]quinazoline,
1-chloro-3-fluoro-6,9-dihydro-11H-6,9-methanopyrido[2,1-b]quinazoline,
1-chloro-3-bromo-6,9-dihydro-11H-6,9-methanopyrido[2,1-b]quinazoline,
1-chloro-3-iodo-6,9-dihydro-11H-6,9-methanopyrido[2,1-b]quinazoline,
1-bromo-3-fluoro-6,9-dihydro-11H-6,9-methanopyrido[2,1-b]quinazoline,
1-bromo-3-chloro-6,9-dihydro-11H-6,9-methanopyrido[2,1-b]quinazoline,
1-bromo-3-iodo-6,9-dihydro-11H-6,9-methanopyrido[2,1-b]quinazoline,
1,3-dibromo-6,9-dihydro-11H-6,9-methanopyrido[2,1-b]quinazoline,
1-iodo-3-fluoro-6,9-dihydro-11H-6,9-methanopyrido[2,1-b]quinazoline,
1-iodo-3-chloro-6,9-dihydro-11H-6,9-methanopyrido[2,1-b]quinazoline,
1-iodo-3-bromo-6,9-dihydro-11H-6,9-methanopyrido[2,1-b]quinazoline,
1,3-diiodo-6,9-dihydro-11H-6,9-methanopyrido[2,1-b]quinazoline,
1-methyl-11H-pyrido[2,1-b]quinazoline,
2-methyl-11H-pyrido[2,1-b]quinazoline,
3-methyl-11H-pyrido[2,1-b]quinazoline,
4-methyl-11H-pyrido[2,1-b]quinazoline,
1-chloro-11H-pyrido[2,1-b]quinazoline,
2-chloro-11H-pyrido[2,1-b]quinazoline,
3-chloro-11H-pyrido[2,1-b]quinazoline,
4-chloro-11H-pyrido[2,1-b]quinazoline,
1-fluoro-11H-pyrido[2,1-b]quinazoline,
2-fluoro-11H-pyrido[2,1-b]quinazoline,
3-fluoro-11H-pyrido[2,1-b]quinazoline,
4-fluoro-11H-pyrido[2,1-b]quinazoline,
1-bromo-11H-pyrido[2,1-b]quinazoline,
2-bromo-11H-pyrido[2,1-b]quinazoline,
3-bromo-11H-pyrido[2,1-b]quinazoline,
4-bromo-11H-pyrido[2,1-b]quinazoline,
1-(trifluoromethyl)-11H-pyrido[2,1-b]quinazoline,
2-(trifluoromethyl)-11H-pyrido[2,1-b]quinazoline,
3-(trifluoromethyl)-11H-pyrido[2,1-b]quinazoline,
4-(trifluoromethyl)-11H-pyrido[2,1-b]quinazoline,
1-(methylthio)-11H-pyrido[2,1-b]quinazoline,
2-(methylthio)-11H-pyrido[2,1-b]quinazoline,
3-(methylthio)-11H-pyrido[2,1-b]quinazoline,
4-(methylthio)-11H-pyrido[2,1-b]quinazoline,
1,2-dichloro-11H-pyrido[2,1-b]quinazoline,
1,3-dichloro-11H-pyrido[2,1-b]quinazoline,
1,4-dichloro-11H-pyrido[2,1-b]quinazoline,
2,3-dichloro-11H-pyrido[2,1-b]quinazoline,
2,4-dichloro-11H-pyrido[2,1-b]quinazoline,
3,4-dichloro-11H-pyrido[2,1-b]quinazoline,
1,3-dimethoxy-11H-pyrido[2,1-b]quinazoline,
2,3-dimethoxy-11H-pyrido[2,1-b]quinazoline,
2,4-dimethoxy-11H-pyrido[2,1-b]quinazoline,
3,4-dimethoxy-11H-pyrido[2,1-b]quinazoline,
1,2-dimethyl-11H-pyrido[2,1-b]quinazoline,
1,3-dimethyl-11H-pyrido[2,1-b]quinazoline,
1,4-dimethyl-11H-pyrido[2,1-b]quinazoline,
2,3-dimethyl-11H-pyrido[2,1-b]quinazoline,
2,4-dimethyl-11H-pyrido[2,1-b]quinazoline,
3,4-dimethyl-11H-pyrido[2,1-b]quinazoline,
2-(methylcarbamoyloxy)-11H-pyrido[2,1-b]quinazoline,
1-chloro-2-(methylcarbamoyloxy)-11H-pyrido[2,1-b]quinazoline,
3-chloro-2-(methylcarbamoyloxy)-11H-pyrido[2,1-b]quinazoline,
1-chloro-3-(methylcarbamoyloxy)-11H-pyrido[2,1-b]quinazoline,
2-(heptylcarbamoyloxy)-11H-pyrido[2,1-b]quinazoline,
3-(heptylcarbamoyloxy)-11H-pyrido[2,1-b]quinazoline,
1-chloro-3-(heptylcarbamoyloxy)-11H-pyrido[2,1-b]quinazoline,
3-chloro-2-(heptylcarbamoyloxy)-11H-pyrido[2,1-b]quinazoline,
1,3-dichloro-2-(heptylcarbamoyloxy)-11H-pyrido[2,1-b]quinazoline,
1-chloro-2-methyl-11H-pyrido[2,1-b]quinazoline,
1-chloro-3-methyl-11H-pyrido[2,1-b]quinazoline,
1-chloro-4-methyl-11H-pyrido[2,1-b]quinazoline,
2-chloro-1-methyl-11H-pyrido[2,1-b]quinazoline,
3-chloro-1-methyl-11H-pyrido[2,1-b]quinazoline,
4-chloro-1-methyl-11H-pyrido[2,1-b]quinazoline,
3-chloro-1-methyl-11H-pyrido[2,1-b]quinazoline,
3-chloro-2-methyl-11H-pyrido[2,1-b]quinazoline,
3-chloro-4-methyl-11H-pyrido[2,1-b]quinazoline,
4-chloro-1-methyl-11H-pyrido[2,1-b]quinazoline, 4-chloro-2-methyl-11H-pyrido[2,1-b]quinazoline,
1-methyl-3-chloro-11H-pyrido[2,1-b]quinazoline,
3-chloro-1,4-dimethyl-11H-pyrido[2,1-b]quinazoline,
1-chloro-3-methyl-11H-pyrido[2,1-b]quinazoline,
1-methyl-3-chloro-11H-pyrido[2,1-b]quinazoline,
1,3-dichloro-2-methyl-11H-pyrido[2,1-b]quinazoline,
1,3-dichloro-4-methyl-11H-pyrido[2,1-b]quinazoline,
1,3-dichloro-2,4-dimethyl-11H-pyrido[2,1-b]quinazoline,
1-chloro-11,11-dimethyl-11H-pyrido[2,1-b]quinazoline,
3-chloro-11,11-dimethyl-11H-pyrido[2,1-b]quinazoline,
1,3-dichloro-11-methyl-11H-pyrido[2,1-b]quinazoline,
1,3-dichloro-11,11-dimethyl-11H-pyrido[2,1-b]quinazoline,
3-chloro-11-methylene-11H-pyrido[2,1-b]quinazoline,
1,3-dichloro-11-isopropylidene-11H-pyrido[2,1-b]quinazoline,
1,3-dichloro-11-methylene-11H-pyrido[2,1-b]quinazoline,
1,3-difluoro-11H-pyrido[2,1-b]quinazoline,
1-fluoro-3-bromo-11H-pyrido[2,1-b]quinazoline,
1-fluoro-3-iodo-11H-pyrido[2,1-b]quinazoline,
1-chloro-3-fluoro-11H-pyrido[2,1-b]quinazoline,
1-chloro-3-bromo-11H-pyrido[2,1-b]quinazoline,
1-chloro-3-iodo-11H-pyrido[2,1-b]quinazoline,
1-bromo-3-fluoro-11H-pyrido[2,1-b]quinazoline,
1-bromo-3-chloro-11H-pyrido[2,1-b]quinazoline,
1-bromo-3-iodo-11H-pyrido[2,1-b]quinazoline,
1,3-dibromo-11H-pyrido[2,1-b]quinazoline,
1-iodo-3-fluoro-11H-pyrido[2,1-b]quinazoline,
1-iodo-3-chloro-11H-pyrido[2,1-b]quinazoline,
1-iodo-3-bromo-11H pyrido[2,1-b]quinazoline,
1,3-diiodo-11H-pyrido[2,1-b]quinazoline,
1,3-dichloro-6,7,8,9,10,11,12,14-octahydro-6,10:8,12-dimethanoazonino[2,1-b]quinazoline,
1-methyl-6,7,8,9,10,11,12,14-octahydro-6,10:8,12-dimethanoazonino[2,1-b]quinazoline,
2-methyl-6,7,8,9,10,11,12,14-octahydro-6,10:8,12-dimethanoazonino[2,1-b]quinazoline,
3-methyl-6,7,8,9,10,11,12,14-octahydro-6,10:8,12-dimethanoazonino[2,1-b]quinazoline,
4-methyl-6,7,8,9,10,11,12,14-octahydro-6,10:8,12-dimethanoazonino[2,1-b]quinazoline,
1-chloro-6,7,8,9,10,11,12,14-octahydro-6,10:8,12-dimethanoazonino[2,1-b]quinazoline,
2-chloro-6,7,8,9,10,11,12,14-octahydro-6,10:8,12-dimethanoazonino[2,1-b]quinazoline,
3-chloro-6,7,8,9,10,11,12,14-octahydro-6,10:8,12-dimethanoazonino[2,1-b]quinazoline,
4-chloro-6,7,8,9,10,11,12,14-octahydro-6,10:8,12-dimethanoazonino[2,1-b]quinazoline,
1-fluoro-6,7,8,9,10,11,12,14-octahydro-6,10:8,12-dimethanoazonino[2,1-b]quinazoline,
3-fluoro-6,7,8,9,10,11,12,14-octahydro-6,10:8,12-dimethanoazonino[2,1-b]quinazoline,
1-bromo-6,7,8,9,10,11,12,14-octahydro-6,10:8,12-dimethanoazonino[2,1-b]quinazoline,
2-bromo-6,7,8,9,10,11,12,14-octahydro-6,10:8,12-dimethanoazonino[2,1-b]quinazoline,
3-bromo-6,7,8,9,10,11,12,14-octahydro-6,10:8,12-dimethanoazonino[2,1-b]quinazoline,
4-bromo-6,7,8,9,10,11,12,14-octahydro-6,10:8,12-dimethanoazonino[2,1-b]quinazoline,
1-(trifluoromethyl)-6,7,8,9,10,11,12,14-octahydro-6,10:8,12-dimethanoazonino[2,1-b]quinazoline,
2-(trifluoromethyl)-6,7,8,9,10,11,12,14-octahydro-6,10:8,12-dimethanoazonino[2,1-b]quinazoline,
3-(trifluoromethyl)-6,7,8,9,10,11,12,14-octahydro-6,10:8,12-dimethanoazonino[2,1-b]quinazoline,
4-(trifluoromethyl)-6,7,8,9,10,11,12,14-octahydro-6,10:8,12-dimethanoazonino[2,1-b]quinazoline,
1,2-dichloro-6,7,8,9,10,11,12,14-octahydro-6,10:8,12-dimethanoazonino[2,1-b]quinazoline,
1,3-dichloro-6,7,8,9,10,11,12,14-octahydro-6,10:8,12-dimethanoazonino[2,1-b]quinazoline,
1,4-dichloro-6,7,8,9,10,11,12,14-octahydro-6,10:8,12-dimethanoazonino[2,1-b]quinazoline,
2,3-dichloro-6,7,8,9,10,11,12,14-octahydro-6,10:8,12-dimethanoazonino[2,1-b]quinazoline,
2,4-dichloro-6,7,8,9,10,11,12,14-octahydro-6,10:8,12-dimethanoazonino[2,1-b]quinazoline,
3,4-dichloro-6,7,8,9,10,11,12,14-octahydro-6,10:8,12-dimethanoazonino[2,1-b]quinazoline,
2,3-dimethoxy-6,7,8,9,10,11,12,14-octahydro-6,10:8,12-dimethanoazonino[2,1-b]quinazoline,
2-(methylcarbamoyloxy)-6,7,8,9,10,11,12,14-octahydro-6,10:8,12-dimethanoazonino[2,1-b]quinazoline,
1-chloro-2-(methylcarbamoyloxy)-6,7,8,9,10,11,12,14-octahydro-6,10:8,12-dimethanoazonino[2,1-b] quinazoline,
3-chloro-2-(methylcarbamoyloxy)-6,7,8,9,10,11,12,14-octahydro-6,10:8,12-dimethanoazonino[2,1-b] quinazoline,
1-chloro-3-(methylcarbamoyloxy)-6,7,8,9,10,11,12,14-octahydro-6,10:8,12-dimethanoazonino[2,1-b] quinazoline,
2-(heptylcarbamoyloxy)-6,7,8,9,10,11,12,14-octahydro-6,10:8,12-dimethanoazonino[2,1-b]quinazoline,
3-(heptylcarbamoyloxy)-6,7,8,9,10,11,12,14-octahydro-6,10:8,12-dimethanoazonino[2,1-b]quinazoline,
1-chloro-3-(heptylcarbamoyloxy)-6,7,8,9,10,11,12,14-octahydro-6,10:8,12-dimethanoazonino[2,1-b]quinazoline,
3-chloro-2-(heptylcarbamoyloxy)-6,7,8,9,10,11,12,14-octahydro-6,10:8,12-dimethanoazonino[2,1-b]quinazoline,
1,3-dichloro-4-methyl-6,7,8,9,10,11,12,14-octahydro-6,10:8,12-dimethanoazonino[2,1-b]quinazoline,
1,3-difluoro-11H-6,7,8,9,10,11,12,14-octahydro-6,10:8,12-dimethanoazonino[2,1-b]quinazoline,
1-fluoro-3-chloro-6,7,8,9,10,11,12,14-octahydro-6,10:8,12-dimethanoazonino[2,1-b]quinazoline,
1-fluoro-3-bromo-6,7,8,9,10,11,12,14-octahydro-6,10:8,12-dimethanoazonino[2,1-b]quinazoline,
1-fluoro-3-iodo-6,7,8,9,10,11,12,14-octahydro-6,10:8,12-dimethanoazonino[2,1-b]quinazoline,
1-chloro-3-fluoro-6,7,8,9,10,11,12,14-octahydro-6,10:8,12-dimethanoazonino[2,1-b]quinazoline,
1-chloro-3-bromo-6,7,8,9,10,11,12,14-octahydro-6,10:8,12-dimethanoazonino[2,1-b]quinazoline,
1-chloro-3-iodo-11H-6,7,8,9,10,11,12,14-octahydro-6,10:8,12-dimethanoazonino[2,1-b]quinazoline,
1-bromo-3-fluoro-6,7,8,9,10,11,12,14-octahydro-6,10:8,12-dimethanoazonino[2,1-b]quinazoline,
1-bromo-3-chloro-6,7,8,9,10,11,12,14-octahydro-6,10:8,12-dimethanoazonino[2,1-b]quinazoline,
1-bromo-3-iodo-6,7,8,9,10,11,12,14-octahydro-6,10:8,12-dimethanoazonino[2,1-b]quinazoline,
1,3-dibromo-6,7,8,9,10,11,12,14-octahydro-6,10:8,12-dimethanoazonino[2,1-b]quinazoline,
1-iodo-3-fluoro-6,7,8,9,10,11,12,14-octahydro-6,10:8,12-dimethanoazonino[2,1-b]quinazoline,
1-iodo-3-chloro-6,7,8,9,10,11,12,14-octahydro-6,10:8,12-dimethanoazonino[2,1-b]quinazoline,
1-iodo-3-bromo-6,7,8,9,10,11,12,14-octahydro-6,10:8,12-dimethanoazonino[2,1-b]quinazoline,
1,3-diiodo-6,7,8,9,10,11,12,14-octahydro-6,10:8,12-dimethanoazonino[2,1-b]quinazoline, and a pharmaceutically acceptable acid addition salt thereof.

As pharmaceutically acceptable acid addition salts of the compounds of Formula I are those of inorganic and organic acids. Preferred inorganic acid salts are, for example, hydrochlorides, hydrobromides, hydroiodides, sulfates, phosphates, and the like. Preferred organic acid salts are acetates, oxalates, maleates, fumarates, lactates, malates, citrates, tartrates, succinates, benzoates, methanesulfonates, and the like. Also preferred are salts of amino acids such as glycinates, alaninates, carnitinates, cysteinates, and the like, including their corresponding N-acetyl derivatives and also salts of polyhydroxy acids as gluconates, acetylneuraminates, alginates, galacturates, galacturonates, and the like.

The compounds of the present invention or salts thereof may also form hydrates or solvates; the hydrates and solvates thereof are also included in the compounds of the present invention.

Depending on the substituents on A or substituents forming a part of M, when M represents

of Formula I, the compounds of the present invention may also contain one or more asymmetric carbon atoms, which optical isomers and/or diastereomers are included as part of the present invention.

The compounds of the present invention and of Formula I may be prepared according to the following procedures.

When M=O, the compounds of Formula I may be prepared by reacting an anthranilic acid of the formula

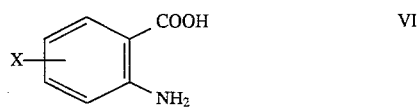

or a reactive derivative thereof, in which X is as defined above, with a lactam or cyclic iminoether or cyclic imidoyl chloride of the formulae

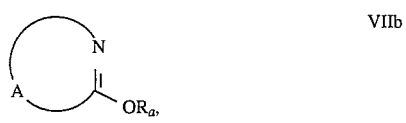

or

in which is as defined above and Ra is alkyl of 1 to 3 carbon atoms, preferably methyl or ethyl.

Anthranilic acids of Formula VI are either commercially available or may be prepared by known methods from commercially available starting materials, e.g., prepared from the corresponding isatines: T. Sandmeyer, *Helv. Chim. Acta*, 2:234 (1919), by oxidation with alkaline hydrogen peroxide, following the procedure described by Baker, et al., *J. Org. Chem.*, 17:141 (1952) for the synthesis of 3-chloroanthranilic acid.

The lactams of Formula VIIa are also either commercially available or may be prepared by known methods from commercially available materials.

Reactive derivatives of anthranilic acids are the anhydrides, also called isatoic anhydrides, 2-(sulfinylamino)benzoyl chlorides or esters, preferably methyl or ethyl, which may be used instead of the anthranilic acids per se.

When the anthranilic acids are used per se, the reaction with VIIb or VIIc takes place at temperatures at or above room temperature and, preferably, at the boiling point of the solvent. The solvent employed is a nonpolar solvent such as, for example, benzene, toluene, xylene, chloroform, methylene chloride, carbon tetrachloride, and the like. Water formed during the reaction may be removed by means of an azeotropic trap.

An isatoic anhydride or 2-(sulfinylamino)benzyl chloride may be used as a reactant with the appropriate lactam of Formula VIIa. The 2-(sulfinylamino)benzoyl chloride is prepared by known means by reacting the corresponding anthranilic acid with thionyl chloride. The reaction of the 2-(sulfinylamino)benzoyl chloride with the lactam may proceed at 0° C. to about 50° C. for about 1 to 24 hours also with the same nonpolar solvent.

An isatoic anhydride formed by action of phosgene on the corresponding anthranilic acid of Formula VI may be used as a starting material and reacted with the appropriate lactam at elevated temperatures, for example, 150° C.–200° C.

A cyclic imino ether of Formula VIIb may be used in the reactions of anthranilic acids or their esters under similar conditions of time, temperatures, and solvent. The cyclic imino ether may be available commercially or prepared from the lactam by reaction with alkylating agents such as dimethyl sulfate, triethyloxonium tetrafluoroborate, or methyl trifluoromethanesulfonate, followed by reaction with base, as described in the literature.

Anthranilic acids or esters of anthranilic acids of Formula VI, preferably methyl or ethyl, may also be used as starting materials and reacted with an imidoyl halide, e.g., chloride VIIc, prepared by treating the corresponding lactam with phosphorus oxychloride. The reaction takes place at room temperature or above (60° C.) in an organic solvent, such as chloroform.

When M=R,R', compounds of Formula I may be prepared by heating a corresponding imidoyl chloride, as prepared above, with a compound of the formula

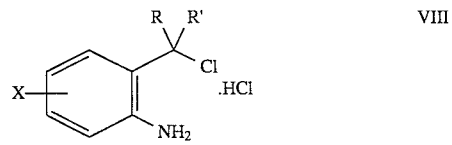

where X, R, and R' are as defined above. The reaction takes place at or above room temperature, preferably between 10° C. and 130° C. in an organic solvent, e.g., chloroform, toluene, chlorobenzene, or a mixture thereof for about 1 to 48 hours.

The starting compounds of Formula VII may be prepared by known methods from commercially available materials. For example, by the well-known Beckmann rearrangement from the corresponding ketoximes, either commercially available or prepared by literature methods, well known to those skilled in the art.

When both R and R' are hydrogen, the compounds of Formula I may be prepared directly from the corresponding compounds of Formula I when M=O by chemical reduction with zinc and hydrochloric acid in the presence of acetic acid. The reaction takes place at 40° C.–100° C., preferably 50° C.–60° C., and between 10 minutes to 5 hours. These compounds can also be prepared by reductive desulfurization with Raney nickel in tetrahydrofuran, or alcohol at 10° C.–100° C., preferably 60° C., of the compounds of Formula I, when M=S, readily prepared from the corresponding oxo-compounds of Formula I, M=O, as described below.

When M=NH, the compounds of Formula I may be prepared by reacting a compound of the formula

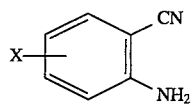

with the appropriate lactim derivative of the Formula VIIb (lactim ether). The reactions are performed at elevated temperatures, e.g., 100° C. to 200° C., preferably 140° C., for about 1 to 5 days in inert (nitrogen or argon) atmosphere.

These compounds can also be prepared by the treatment of the cyano intermediate IX with an imidoyl chloride VIIc at 0° C.–100° C. (preferably 25° C.), for 1 to 48 hours. The imidoyl chlorides are prepared from the corresponding lactams VIIa by the treatment with phosphorus oxychloride, or analogous reagents, as is well known to those skilled in the art. The resulting compound of the Formula X

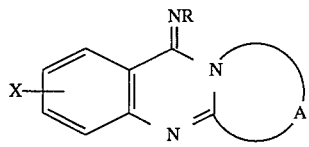

may, if desired to form a compound where R is other than hydrogen, be treated with a corresponding bromide R—Br or iodide R—I, in the presence of sodium hydride.

Alternatively, such compounds can be obtained by the treatment of the corresponding thiones (compounds of the Formula I, where M=S, obtained as described below), with ammonia or amines R—$NH_2$ at elevated temperatures (60° C.–180° C.).

When M=S, the compounds of the Formula I may be prepared by reacting a compound of Formula I when M=O with phosphorus pentasulfide or the Lawesson reagent, [2,4-bis(4-methoxyphenyl)-1,3-dithia-2,4 -diphosphetane-2, 4-disulfide] at 100°–150° C., preferably at 110° C. in boiling toluene for 24 hours.

The compounds of the present invention and of Formula I are inhibitors of acetylcholinesterase, centrally acting with favorable distribution into the central nervous system versus the periphery. They also may be inhibitors of cholinesterase other than acetylcholinesterase, and may stop or reverse Alzheimer's disease plaques and tangles (amyloid protein) formation by inhibition of the protease enzymes responsible for their formation.

Representative compounds of the present invention have been found to possess acetylcholinesterase inhibiting effects in vitro as shown in the following table. The in vitro data was obtained according to the radiometric assay of C. D. Johnson and R. L. Russell described in *Anal. Biochem.*, 64:229–238 (1975) and modified as described by M. R. Emmerling and H. M. Sobkowicz in *Hearings Research*, 32:137–146 (1988); the rat brain homogenate acetylcholinesterase inhibition data were obtained by the Ellman assay, described by G. L. Ellman, D. Courtney, V. Andres, and R. M. Feathersome, described in *Biochem. Pharmacol.* 7:88–95 (1961), and modified as described by M. J. Marks, D. M. Patinkin, L. D. Artman, J. B. Busch, and A. C. Collins in *Pharmacol. Biochem. and Behav.*15:271–279 (1981), which references are incorporated herein.

TABLE I

Inhibition of Acetylcholinesterase by Dihydroquinazolines

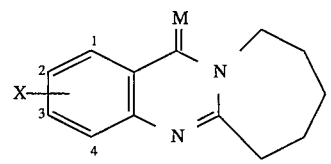

| X = | M = | Human Red Blood Cell AChE (nM) | Rat Brain Homogenate AChE (nM) | Electric Eel AChE (nM) |
|---|---|---|---|---|
| 1-Cl | $H_2$ | 1,700 | — | — |
| 2-Cl | $H_2$ | 500 | — | — |
| 3-Cl | $H_2$ | 158 | 1,900 | 200 |
| 4-Cl | $H_2$ | 1,500 | 16,400 | 631 |
| 2-$CH_3$ | $H_2$ | 1,800 | — | — |
| 3-$CH_3$ | $H_2$ | 610 | — | — |
| 4-$CH_3$ | $H_2$ | 6,000 | — | — |
| 1-F | $H_2$ | 1,900 | — | — |
| 2-F | $H_2$ | 2,000 | — | — |
| 3-F | $H_2$ | 2,870 | — | 600 |
| 4-F | $H_2$ | 1,600 | — | 1,500 |
| 3-$OCH_3$ | $H_2$ | 2,800 | — | — |
| 2-CN | $H_2$ | 6,700 | — | 1,500 |
| 2-$C_2H_5$ | $H_2$ | 2,500 | — | 1,000 |
| H | $H_2$ | 1,900 | 16,000 | 610 |
| 1,2-DiCl | $H_2$ | 3,162 | — | — |
| 1,3-DiCl | $H_2$ | 40 | 172 | 158 |
| 2,3-DiCl | $H_2$ | 2,500 | 17,850 | 398 |
| 1,4-DiCl | $H_2$ | 631 | 16,450 | 100 |
| 2,4-DiCl | $H_2$ | 63 | 3,810 | 250 |
| 3,4-DiCl | $H_2$ | 1,500 | 23,800 | 398 |
| 2,4-Di$CH_3$ | $H_2$ | 900 | — | — |
| 2,3-Di$OCH_3$ | $H_2$ | 9,000 | — | 398 |
| 1-$CH_3$, 2-Cl | $H_2$ | 3,981 | — | — |
| 2-$CH_3$, 4-Cl | $H_2$ | 631 | — | — |
| 1,3-DiCl, 2-Me | $H_2$ | 1,000 | — | — |
| 3-Cl | O | >100,000 | — | 21,000 |
| 3-Cl | S | >100,000 | — | 15,800 |
| 3-Cl | NH | 1,260 | — | 500 |

TABLE II

Inhibition of Human Red Blood Cell Acetylcholinesterase by Dihydroquinazolines

| Structure | $IC_{50}$ Human AChE (nM) |
|---|---|
| (structure with Cl, Cl substituents) | 60 |

TABLE II-continued
Inhibition of Human Red Blood Cell Acetylcholinesterase by Dihydroquinazolines

| Structure | IC$_{50}$ Human AChE (nM) |
|---|---|
| (3,5-dichlorobenzyl, bicyclic amine) | 50 |
| (3,5-dichlorobenzyl, diphenylpiperidine) | 63 |
| (3,5-dichloro, A-B-C gem-dimethyl azepine) | 2,000 |
| (3,5-dichlorobenzyl, bridged CH$_2$ bicyclic) | 1,000 |
| (monochloro, bridged CH$_2$ bicyclic) | 920 |
| (3,5-dichlorobenzyl, pyrrolidine) | 200 |
| (3,5-dichlorobenzyl, piperidine fused) | 60 |
| (3,5-dichloro, carbonyl, 7-ring) | 63,000 |

TABLE III
Inhibition of Electric Eel Acetylcholinesterase by Dihydroquinazolines

| Structure | IC$_{50}$ Eel AChE (nM) |
|---|---|
| Desoxypeganine | 1,600 |
| (pyridine fused) | 1,600 |
| (7-membered ring) | 610 |
| (NH imine, 6-ring) | 1,000 |
| (NH imine, 7-ring) | 2,000 |
| (CF$_3$, 7-ring) | 1,000 |
| (diphenyl piperidine) | 370 |
| (8-membered ring) | 4,300 |
| (9-membered ring) | 4,000 |
| (5-ring, Ph (±)) | 3,100 |

Thus, the compounds of the present invention may be used in treating Alzheimer's disease, senile dementias, multiple infarct dementias, and other conditions where memory and cognitive function improvement or stabilization is desired.

When the compound of the present invention is used as a therapeutic agent, it may be administered singly or as a composite by compounding with a carrier which is pharmaceutically acceptable. Compositions thereof may be determined by the solubility, chemical properties, route of administration, administration scheme, etc., of the compounds.

For example, it may be administered orally in the form of granules, fine grains, powders, tablets, hard capsules, soft capsules, syrups, emulsions, suspensions or liquids, or may be administered parenterally, i.e., intravenously or intramuscularly as an injection.

Also, by making a powder for injection, it may be used per se by preparing when using it. An organic or inorganic carrier which is in the form of solid or liquid, or a diluent, which are pharmaceutically acceptable for oral, rectal, parenteral, or local administration may be used in combination with the compound of the present invention. As excipients to be used for preparing solid preparations, for example, lactose, sucrose, starch, talc, cellulose, dextrin, kaolin, calcium carbonate, etc, are used. Liquid preparations for oral administration, that is, emulsions, syrups, suspensions, liquids, etc., contain inert diluents which are conventionally used such as water or a vegetable oil, etc. This preparation may be contained, in addition to the inert diluents, such as auxiliaries, e.g., wettables, suspension auxiliaries, sweeteners, aromatics, colorants or preservatives, etc. It may be made in the form of liquid preparations and contained in a capsule made of a substance which is absorbable such as gelatin, etc. As the preparations for parenteral administration, that is, solvents or suspending agents to be used for preparation of injections, etc., there may be mentioned, for example, water, propylene glycol, polyethylene glycol, benzyl alcohol, ethyl oleate, lecithin, etc. Preparative methods of the preparations may be based on the conventional method.

Regarding a clinical dosage, when it is used via oral administration, a dose per day is generally 1 to 1000 mg, preferably 1 to 100 mg of the compound of the present invention per an adult, but the dose may be optionally varied depending upon age, severity of disease, condition of the patient, presence or absence of simultaneous administration, etc. The above dose per day of the compound of the present invention may be administered once per day or may be administered twice or three times per day with suitable intervals by dividing it, or may be administered intermittently.

Also, when it is used as injections, it is used as the dose per day of 0.1 to 100 mg, preferably 0.1 to 50 mg as the compound of the present invention per an adult.

The following examples provide by way of illustration a detailed description of the synthesis of representative compounds of the present invention.

EXAMPLE 1

I. 3-Chloro-7,8,9,10-tetrahydroazpino[2,1-b]quinazolin-12(6H)-one

To a stirred slurry of 17.16 g of 4-chloroanthranilic acid (Aldrich) in 120 mL benzene was added 14 mL 1-aza-2-methoxy-1-cycloheptene (1) (Aldrich) and refluxed under nitrogen using an azeotropic Dean-Stark trap to remove the water/methanol formed by the reaction. After 2 hours of reflux, 5 mL of the methoxyimine (1) was added and 2 mL more after 18 hours. The mixture was then refluxed for 4 more hours. The solvent was distilled out and the excess of (1) was removed by distillation at 140° C. (bath) at 11 mm Hg. A dark brown oil formed which soon crystallized. There was a single mobile spot on TLC (4:1 chloroform-ethyl acetate, Rf=0.6, silica gel). The mixture was chromatographed using the above solvent system, the corresponding fractions concentrated in vacuo and the residue was recrystallized from hexane-ethyl acetate, giving 19.08 g of the 3-chloro-6,7,8,9-tetrahydroazepino[2,1-b]quinazolin-12(6H)-one (76.7% yield), m.p. 106°–108° C.

II. 3-Chloro-7,8,9,10-tetrahydroazepino[2,1-b]quinazolin-12(6H)-thione 10 g of 3-chloro-7,8,9,10-tetrahydroazepino[2,1-b]quinazolin-12(6H)-one was treated with 15 g of Lawesson's reagent in toluene at reflux under nitrogen, until the starting material was consumed, as checked by TLC, using chloroform as eluent (24 hours). The mixture was concentrated in vacuo and chromatographed on silica gel, using chloroform as eluent. The bright yellow material was recrystallized from hexane-ethyl acetate, giving lemon-yellow needles, m.p. 99° C.–101° C.

III. 3-Chloro-6,7,8,9,10,12-hexahydroazepino[2,1-b]quinazoline

To a solution of 2 g of 3-chloro-7,8,9,10 -tetrahydroazepino[2,1-b]quinazolin-12(6H)-one, dissolved in 50 mL of glacial acetic acid was stirred 25 g of zinc dust with vigorous mechanical stirring. The mixture was heated to 55° C.–60° C. and concentrated hydrochloric acid was added dropwise (approximately 20 mL). The reaction was checked by TLC. Usually between 20 minutes to 5 hours were required for completion. The excess zinc was filtered off, the solution concentrated in vacuo, and basified with 20% sodium hydroxide solution. The product was extracted with tetrahydrofuran. Then the free base was chromatographed using 300:25:1 $CHCl_3$:MeOH:28% aqueous ammonia. The corresponding fractions were combined, concentrated in vacuo, and dried in high vacuum providing the 3-chloro-6,7,8,9,10,12-hexahydroazepino[2,1-b]quinazoline as a white crystalline solid; m.p. 102° C.–104° C. To convert to its hydrochloride salt, the base was treated with one equivalent of 4N HCl in 50 mL absolute ethanol. The solution was concentrated in vacuo, redissolved in absolute ethanol, and concentrated in vacuo. Then the hydrochloride was recrystallized from absolute ethyl alcohol with little ethyl acetate, giving white crystals, m.p. 270° C.–271° C. (dec.).

EXAMPLE 2

I. 1,3-Dichloro-7,8,9,10-tetrahydroazepino[2,1-b]quinazolin-12(6H)-one

To a stirred suspension of 15 g of 4,6-dichloroanthranilic acid (prepared from the corresponding isatine: T. Sandmeyer Helv. Chim. Acta, 2:234 (1919), by oxidation with alkaline hydrogen peroxide, following the procedure described by Baker et al., J. Org. Chem., 17:141 (1952) for the synthesis of 3-chloroanthranilic acid) in 100 mL of toluene was added 20 g of 1-aza-2-methoxy-1-cycloheptene. The mixture was stirred for an hour at room temperature, followed by heating under reflux for 18 hours. Then the mixture was concentrated in vacuo and volatile material was removed at 130° C. at 1 torr. The dark brown residue was chromatographed using 8:1 chloroform-ethyl acetate to give 9 g of the desired material as a crystalline solid, m.p. 110° C.–112° C.

II. Method A: 1,3-Dichloro-6,7,8,9,10,12 -hexahydroazepino[2,1-b]quinazoline hydrochloride To a mechanically stirred solution of 1.5 g of the above quinazolinone derivative in 150 mL of glacial acetic acid at 60° C. was added 25 g of zinc dust. To the grey suspension was then added dropwise 25 mL of concentrated hydrochloric acid in 25 mL of glacial acetic acid in approximately 10 minutes and stirred for 10 minutes more at 60° C., when the reaction appeared essentially complete by TLC. Then the excess of zinc was filtered off with suction (Caution!, the zinc is pyrophoric!), washed with 4×30 mL of glacial acetic acid, and the filtrate was concentrated in vacuo. To the residue was added 50 mL of 10% aqueous sodium hydroxide and the product was extracted with tetrahydrofuran (3×150 mL). The organic extract was concentrated in vacuo and the residue was distributed between 100 mL of chloroform and 25 mL of water. The combined extract was dried with anhydrous potassium carbonate, filtered, concentrated in vacuo, and flash chromatographed on silica gel, using 95:5 (1 L) and 90:10 (1 L) of chloroform-methanol. The desired compound was obtained as a white solid after concentration in vacuo of the corresponding fractions. The base was treated with 1 equivalent of 4N HCl in 50 mL of absolute ethanol, concentrated in vacuo, redissolved in 50 mL of absolute EtOH, concentrated, repeated again. Then the solid was recrystallized from absolute EtOH-EtOAc, giving white crystals of the hydrochloride salt, m.p. 318° C.–319° C. (dec.).

II. Method B: 1,3-Dichloro-6,7,8,9,10,12-hexahydroazepino[2,1-b]quinazoline hydrochloride To a solution of 1 g of 1,3-dichloro-7,8,9,10 -tetrahydroazepino[2,1-b]quinazolin-12(6H)-one in 15 mL of triethylsilane was added 8 g of anhydrous zinc chloride and the mixture was refluxed under nitrogen with vigorous stirring. The triethylsilane was replenished in about 8-hour intervals. When the reaction was judged complete by TLC (300:25:1 chloroform:methanol: 28% aqueous ammonia, basified aliquot) the excess of triethylsilane and other volatiles were removed in vacuo and the residue was purified and worked-up as in Method A to give the desired 1,3-dichloro-6,7,8,9,10,12-hexahydroazepino[2,1-b]quinazoline hydrochloride as white crystalline solid.

EXAMPLE 3

I. 1,3-Dichloro-7,8,9,10-tetrahydro-6,10 -methanoazepino[2,1-b]quinazolin-12(6H)-one To a solution of 3.82 g of 6-azabicyclo[3,2,1 ]-octan-7-one (R. L. Augustine and L. A. Bag, *J. Org. Chem.*, 40:1074 (1975)) in 25 mL of chloroform was added 4 mL of phosphorus oxychloride. After the mildly exothermic reaction ceased, the mixture was stirred at room temperature for 4 hours. 6.3 g of 4,6-dichloroanthranilic acid (prepared from the corresponding isatine: T. Sandmeyer, *Helv. Chim. Acta*, 2:234 (1919), by oxidation with alkaline hydrogen peroxide, following the procedure described by Baker, et al., *J. Org. Chem.*, 17:141 (1952) for the synthesis of 3-chloroanthranilic acid) was dissolved in a mixture of 50 mL of chloroform and 10 mL of triethylamine. This solution was added to the stirred above solution of the imidoyl chloride at such a rate as to prevent boiling over (exothermic!), approximately 2 minutes. Then the mixture was stirred at room temperature for 4 hours and then refluxed for 3 days. Then the dark brown mixture was treated with 200 mL of 10% aqueous $K_2CO_3$. The chloroform layer was separated, aqueous layer was extracted two times with 50 mL of chloroform. The combined chloroform extract was dried with anhydrous potassium carbonate, filtered, and concentrated in vacuo. The residue was chromatographed on silica gel, using 8:1 chloroform-ethyl acetate as eluent. The corresponding fractions were concentrated in vacuo, giving a crystalline solid. This was recrystallized from ethyl acetate-hexane, giving colorless crystals.

II. 1,3-Dichloro-6,7,8,9,10,12-hexahydro-6,10-methanoazepino[2,1-b]quinazoline

To a mechanically stirred solution of 2.5 g of the above quinazolinone derivative in 150 mL of glacial acetic acid, at 60° C. was added 30 g of zinc dust. To the grey suspension was then added dropwise 30 mL of concentrated hydrochloric acid in approximately 15 minutes, followed by stirring at 60° C. for another 10 minutes, when the reaction appeared essentially complete by TLC. Then the excess of zinc was filtered with suction (Caution!, the zinc is pyrophoric!), washed with 4×30 mL of glacial acetic acid, and the filtrate was concentrated in vacuo. To the residue was added 80 mL of 20% aqueous sodium hydroxide and the product was extracted with tetrahydrofuran (100 mL and 2×50 mL). The organic extract was concentrated in vacuo and the residue was distributed between 100 mL of chloroform and 25 mL of water. The aqueous layer was extracted with 2×25 mL of chloroform. The combined extract was dried with anhydrous potassium carbonate, filtered, concentrated in vacuo, and flash chromatographed on silica gel, using 10:1 chloroform-methanol. The desired compound was obtained as a white solid. The base was treated with 1 equivalent of 4N HCl in 50 mL absolute ethanol, concentrated in vacuo, redissolved in 50 mL of absolute EtOH, concentrated, repeated again. Then the white solid was recrystallized from absolute EtOH-EtOAc, giving white crystals of the hydrochloride salt, m.p. 265° C.–268° C. (dec).

EXAMPLE 4

6,8-Dichloro-1,2,3,9-tetrahydropyrrolo[2,1-b]quinazoline

To a stirred solution of 2.5 g of 2-pyrrolidinone (Aldrich) in 100 mL of chloroform was added 4.5 g of phosphorus oxychloride at room temperature. The mixture was stirred for 2.5 hours at room temperature. To the above mixture was then added dropwise a solution of 5 g of 4,6-dichloroanthranilic acid (prepared from the corresponding isatine: T. Sandmeyer, *Helv. Chim. Acta*, 2:234 (1919), by oxidation with alkaline hydrogen peroxide, following the procedure described by Baker, et al, *J. Org. Chem.*, 18:141 (1952) for the synthesis of 3-chloroanthranilic acid) in 50 mL of chloroform, containing 10 mL of triethylamine. Then the mixture was heated to reflux for 6 hours. Then the reaction mixture was carefully treated with 10 mL of water (exothermic!), followed by 10 g of solid anhydrous potassium carbonate. The mixture was filtered and the filtrate was concentrated in vacuo. The residue was chromatographed on silica gel using 10:1 chloroform:ethyl acetate as eluent. After concentration in vacuo of the appropriate fractions, there was obtained 1.5 g of crystalline 6,8-dichloro-2,3-dihydropyrrolo[2,1-b]quinazolin-9(1H)-one), which was used as such in the next step.

To a mechanically stirred solution of 1.5 g of the above 6,8-dichloro-2,3-dihydropyrrolo[2,1-b] quinazolin-9(1H)-one in 150 mL of glacial acetic acid at 60° C. was added 25 g of zinc dust. To this suspension was then added dropwise a solution of 35 mL of concentrated hydrochloric acid in 50 mL of glacial acetic acid in 20 minutes. After the addition was complete, the mixture was stirred for an additional 10 minutes. Then the unreacted zinc was filtered off (Caution!, Pyrophoric!), washed with 4×30 mL of glacial acetic acid and the filtrate was concentrated in vacuo. To the residue was added 80 mL of 20% aqueous sodium hydroxide and the product was extracted with tetrahydrofuran (3 times 150 mL). The organic extract was concentrated in vacuo and the residue was distributed between 100 mL of chloroform and 25 mL of water. The aqueous layer was extracted with 2×25 mL of chloroform. The combined extract was dried with anhydrous potassium carbonate, filtered, concentrated in vacuo, and flash chromatographed on silica gel, using 10:1 chloroform-methanol as eluent. The base was treated with 1 equivalent of 4N HCl in 50 mL absolute ethanol, concentrated in vacuo, redissolved in 50 mL absolute EtOH, concentrated, repeated again. Then the white solid was recrystallized from absolute EtOH-EtOAc, giving after drying in vacuo 0.8 g of 6,8-dichloro-1,2,3,9-tetrahydropyrrolo[2,1-b]-quinazoline hydrochloride in the form of white crystals, m.p. 305° C.–310° C. (dec.).

EXAMPLE 5

I. 1-Chlor-7,8,9,10-tetrahydroazepino[2,1-b]-quinazolin-12(6H)-one 18.01 g 6-chloroanthranilic acid suspended in 100 mL toluene was treated with 14 mL 1-aza-2-methoxy-1-cycloheptene (1) and refluxed with stirring under a Dean-Stark trap to remove the forming water and methanol for 1 hour. An exothermic reaction ensued, forming a two-layer mixture and foaming considerably. This gradually dissolved, giving a brown solution. Then 9 mL of (1) was added and the mixture was refluxed for 18 more hours. The toluene was removed in vacuo and excess of (1) was distilled out at 11 mmHg at 140° C. bath. The residue was chromatographed (6:1 chloroform-ethyl acetate) and recrystallized from hexane-ethyl acetate. The product, 1-chloro-tetrahydroazepino[2,1-b]quinazolin-12(6H)-one, was obtained as a white, crystalline solid, m.p. 128° C.–129° C.; yield 16.5 g.

II. 1-Chloro-6,7,8,9,10,12-hexahydroazepino[2,1-b]quinazoline

The reduction of 1-chloro-7,8,9,10-tetrahydroazepino[2,1-b]quinazolin-12(6H)-one to the 1-chloro-6,7,8,9,10,12-hexahydroazepino[2,1-b]quinazoline was performed in the same manner as described in Example 1 to 4.

EXAMPLE 6

I. 2-Chloro-7,8,9,10-tetrahydroazepino[2,1-b]quinazolin-12(6H)-one

Method A

5-Chloro-2-aminobenzoic acid was converted to 2-chloro-6,7,8,9,10,12-hexahydroazepino[2,1-b]quinazolin-12-one by the same procedure as described in Example 1.

Method B 2.5 g of 5-chloroisatoic anhydride (Aldrich) was mixed intimately with 1.1 g of epsilon-caprolactam (Aldrich). The mixture was then heated in an oil bath at 185° C.–190° C. The mixture melted with effervescence. The molten mass was stirred with heating until the gas evolution ceased. The cooled light greenish mass was then dissolved in 6:1 chloroform:ethyl acetate (10 mL) and chromatographed on silica gel, using the above solvent system as eluent, followed by recrystallization from hexaneethyl acetate.

II. 2-Chloro-6,7,8,9,10,12-hexahydroazepino[2,1-b]quinazoline

The reduction of 2-chloro-7,8,9,10-tetrahydroazepino[2,1-b]quinazolin-12(6H)-one to the 2-chloro-6,7,8,9,10,12-hexahydroazepino[2,1-b]quinazoline was performed in the same manner as described in Examples 1 to 9.

EXAMPLE 7

I. 4-Chloro-7,8,9,10-tetrahydroazepino[2,1,b]quinazolin-12(6H)-one

3-Chloro-2-aminobenzoic acid, obtained by catalytic hydrogenation of 3-chloro-2-nitrobenzoic acid over Ra-Ni in tetrahydrofuran was treated with 1-aza-2-methoxy-1-cycloheptene as outlined in Example 1. The crude mixture was composed mainly of the methylester of 3-chloro-2-aminobenzoic acid and a small amount of the desired compound. This crude mixture was added to a solution formed from one equivalent of ε-caprolactam and one equivalent of phosphorus oxychloride in 50 mL benzene, refluxed for 2 hours and then 50 mL 10% sodium hydroxide solution was added and the organic layer was separated, dried, and concentrated in vacuo. The residue was chromatographed by column chromatography on silica gel using 20:1 chloroform-ethyl acetate to give 9 g (53%) of the desired product as an off-white crystalline solid.

II. 4-Chloro-6,7,8,9,10,12-hexahydro[2,1-b]quinazoline

The reduction of 4-chloro-7,8,9,10-tetrahydroazepino[2,1-b]quinazolin-12(6H)-one to the 4-chloro-6,7,8,9,10,12-hexahydroazepino[2,1-b]quinazoline was performed in the same manner as described in Example 1 to 4, the m.p. of the hydrochloride salt is 272° C.–273° C. (dec).

EXAMPLE 8

I. 3-Methyl-7,8,9,10-tetrahydroazepino[2,1-b]quinazolin-12(6H)-one 25 g 2-bromo-4-methylbenzoic acid was treated with 150 mL of 28% aqueous ammonia, 50 g gaseous ammonia, 1 g CuSO$_4$ at 140° C. for 12 hours in an autoclave, then concentrated in vacuo, dissolved in a minimal amount of water, pH adjusted to 6 with 4N HCl. The precipitate was filtered, washed with ice cold water, and dried at 60° C. The residue was extracted with THF and concentrated in vacuo, giving a light brown crystalline solid. Yield of combined material: 14 g 4-methylanthranilic acid.

6.4 g of this acid was suspended with stirring in 100 mL toluene. 11 mL 1-Aza-2-methoxy-1-cycloheptene (1) (Aldrich) were added and the mixture was refluxed under a Dean-Stark trap for 12 hours. Then the toluene was removed by distillation in vacuo, followed by removal of excess (1) in vacuo (11 mm Hg) at 140° C. The dark brown residue crystallized. It was purified by column chromatography (6:1 chloroformethyl acetate) followed by recrystallization from hexane-ethyl acetate to give 7.1 g of pure 3-methyl-7,8,9,10-tetrahydroazepino[2,1-b]quinazolin-12(6H)-one as white, shiny crystals.

II. 3-Methyl-7,8,9,10-tetrahydroazepino[2,1-b]quinazoline-12(6H)-thione 9 g of 3-methyl-6,7,8,9,10,12-hexahydroazepino[2,1-b]quinazolin-12-one was treated with 15 g of Lawesson's reagent in toluene at reflux under nitrogen until the starting material was consumed, checked by TLC, using chloroform as eluent (24 hours). The mixture was concentrated in vacuo and chromatographed on silica gel, using chloroform as eluent. The bright yellow material was recrystallized from hexane-ethyl acetate.

III. 3-Methyl-6,7,8,9,10,12-hexahydroazepino[2,1-b]quinazoline

Method A

The reduction of 3-methyl-6,7,8,9,10,12-hexahydroazepino[2,1-b]quinazoline-12-one to the 3-methyl-6,7,8,9,10,12-hexahydroazepino[2,1-b]quinazoline was performed in the same manner as described in Examples 1 to 4, hydrochloride salt, m.p. 260° C.–261° C. (dec).

Method B

3-Methyl-6,7,8,9,10,12-hexahydroazepino[2,1-b]quinazoline

To a mechanically stirred solution of 5 g of 3-methyl-7,8,9,10-tetrahydroazepino[2,1-b]quinazoline-12(6H)-thione in 150 mL of boiling tetrahydrofuran was added in small portions wet Raney nickel (W-2, Davison Chemical, Chattanooga, Tenn.). The progress of the reaction was followed by TLC. When the reaction was complete, the mixture was filtered, solids on the filter were washed thoroughly with tetrahydrofuran and the filtrate was concentrated down. The rest of the workup was identical to that described in method A.

EXAMPLE 9

The following compounds are prepared by application of any of the procedures described in Examples 1 to 8:
1) 1-methyl-6,7,8,9,10,12-hexahydroazepino[2,1-b]quinazoline,
2) 2-methyl-6,7,8,9,10,12-hexahydroazepino[2,1-b]quinazoline, HCl salt, m.p. 244° C.–245° C.
3) 3-methyl-6,7,8,9,10,12-hexahydroazepino[2,1-b]quinazoline, HCl salt, m.p. 260° C.–261° C. (dec).
4) 4-methyl-6,7,8,9,10,12-hexahydroazepino[2,1-b]quinazoline, HCl salt, m.p. <280° C. (dec).
5) 1-chloro-6,7,8,9,10,12-hexahydroazepino[2,1-b]quinazoline, HCl salt, m.p. <280° C. (dec).
6) 2-chloro-6,7,8,9,10,12-hexahydroazepino[2,1-b]quinazoline, HCl salt, m.p. 277° C. (dec).
7) 3-chloro-6,7,8,9,10,12-hexahydroazepino[2,1-b]quinazoline, HCl salt, m.p. 270° C.–271° C. (dec).
8) 4-chloro-6,7,8,9,10,12-hexahydroazepino[2,1-b]quinazoline, HCl salt, m.p. 272° C.–273° C. (dec).
9) 1-fluoro-6,7,8,9,10,12-hexahydroazepino[2,1-b]quinazoline, HCl salt, m.p. 271° C.–272° C. (dec).
10) 2-fluoro-6,7,8,9,10,12-hexahydroazepino[2,1-b]quinazoline, HCl salt, m.p. 280° C.–282° C. (dec).
11) 3-fluoro-6,7,8,9,10,12-hexahydroazepino[2,1-b]quinazoline, HCl salt, m.p. 295° C.–298° C. (dec).
12) 4-fluoro-6,7,8,9,10,12-hexahydroazepino[2,1-b]quinazoline, HCl salt, m.p. 254° C.–256° C. (dec).
13) 1-(trifluoromethyl)-6,7,8,9,10,12-hexahydroazepino[2,1-b]quinazoline,
14) 2-(trifluoromethyl)-6,7,8,9,10,12-hexahydroazepino[2,1-b]quinazoline,
15) 3-(trifluoromethyl)-6,7,8,9,10,12-hexahydroazepino[2,1-b]quinazoline,
16) 4-(trifluoromethyl)-6,7,8,9,10,12-hexahydroazepino[2,1-b]quinazoline,
17) 1,2-dichloro-6,7,8,9,10,12-hexahydroazepino[2,1-b]quinazoline, HCl salt, m.p. 300° C.–303° C. (dec).
18) 1,3-dichloro-6,7,8,9,10,12-hexahydroazepino[2,1-b]quinazoline, HCl salt, m.p. 318° C.–319° C. (dec).
19) 1,4-dichloro-6,7,8,9,10,12-hexahydroazepino[2,1-b]quinazoline, HCl salt, m.p. 275° C.–276° C. (dec).
20) 2,3-dichloro-6,7,8,9,10,12-hexahydroazepino[2,1-b]quinazoline, HCl salt, m.p. 323° C.–325° C. (dec). 21) 2,4-dichloro-6,7,8,9,10,12-hexahydroazepino[2,1-b]quinazoline, HCl salt, m.p. 294° C.–295° C. (dec).
22) 3,4-dichloro-6,7,8,9,10,12-hexahydroazepino[2,1-b]quinazoline, HCl salt, m.p. 298° C.–300° C. (dec).
23) 2,3-dimethoxy-6,7,8,9,10,12-hexahydroazepino[2,1-b]quinazoline, HCl salt, m.p. 233° C.–235° C. (dec).
24) 2,4-dimethoxy-6,7,8,9,10,12-hexahydroazepino[2,1-b]quinazoline,
25) 3,4-dimethoxy-6,7,8,9,10,12-hexahydroazepino[2,1-b]quinazoline,
26) 1,2-dimethyl-6,7,8,9,10,12-hexahydroazepino[2,1-b]quinazoline,
27) 1,3-dimethyl-6,7,8,9,10,12-hexahydroazepino[2,1-b]quinazoline,
28) 1,4-dimethyl-6,7,8,9,10,12-hexahydroazepino[2,1-b]quinazoline,
29) 2,3-dimethyl-6,7,8,9,10,12-hexahydroazepino[2,1-b]quinazoline,
30) 2,4-dimethyl-6,7,8,9,10,12-hexahydroazepino[2,1-b]quinazoline, HCl salt, m.p. >266° C. (dec).
31) 3,4-dimethyl-6,7,8,9,10,12-hexahydroazepino[2,1-b]quinazoline,
32) 2-ethyl-6,7,8,9,10,12-hexahydroazepino[2,1-b]quinazoline, HCl salt, m.p. 260° C.–261° C. (dec).
33) 2-(methylcarbamoyloxy)-6,7,8,9,10,12-hexahydroazepino[2,1-b]quinazoline,
34) 2-(heptylcarbamoyloxy)-6,7,8,9,10,12-hexahydroazepino[2,1-b]quinazoline,
35) 1-chloro-2-methyl-6,7,8,9,10,12-hexahydroazepino[2,1-b]quinazoline,
36) 1-chloro-3-methyl-6,7,8,9,10,12-hexahydroazepino[2,1-b]quinazoline,
37) 1-chloro-4-methyl-6,7,8,9,10,12-hexahydroazepino[2,1-b]quinazoline,
38) 2-chloro-1-methyl-6,7,8,9,10,12-hexahydroazepino[2,1-b]quinazoline, HCl salt, m.p. 288° C.–291° C. (dec).
39) 3-chloro-1-methyl-6,7,8,9,10,12-hexahydroazepino[2,1-b]quinazoline,
40) 4-chloro-1-methyl-6,7,8,9,10,12-hexahydroazepino[2,1-b]quinazoline,
41) 3-chloro-1-methyl-6,7,8,9,10,12-hexahydroazepino[2,1-b]quinazoline,
42) 3-chloro-2-methyl-6,7,8,9,10,12-hexahydroazepino[2,1-b]quinazoline,
43) 3-chloro-4-methyl-6,7,8,9,10,12-hexahydroazepino[2,1-b]quinazoline,
44) 4-chloro-1-methyl-6,7,8,9,10,12-hexahydroazepino[2,1-b]quinazoline,
45) 4-chloro-2-methyl-6,7,8,9,10,12-hexahydroazepino[2,1-b]quinazoline, HCl salt, m.p. 271° C.–273° C. (dec).
46) 4-chloro-3-methyl-6,7,8,9,10,12-hexahydroazepino[2,1-b]quinazoline,
47) 3-chloro-2,4-dimethyl-6,7,8,9,10,12-hexahydroazepino[2,1-b]quinazoline,
48) 1,3-dichloro-2-methyl-6,7,8,9,10,12-hexahydroazepino[2,1-b]quinazoline,
49) 1,3-dichloro-4-methyl-6,7,8,9,10,12-hexahydroazepino[2,1-b]quinazoline,
50) 1,3-dichloro-2,4-dimethyl-6,7,8,9,10,12-hexahydroazepino[2,1-b]quinazoline,
51) 1-chloro-7,7-dimethyl-6,7,8,9,10,12-hexahydroazepino[2,1-b]quinazoline,
52) 3-chloro-7,7-dimethyl-6,7,8,9,10,12-hexahydroazepino[2,1-b]quinazoline,
53) 1-chloro-9,9-dimethyl-6,7,8,9,10,12-hexahydroazepino[2,1-b]quinazoline,
54) 3-chloro-9,9-dimethyl-6,7,8,9,10,12-hexahydroazepino[2,1-b]quinazoline,
55) 1,3-dichloro-7,7-dimethyl-6,7,8,9,10,12-hexahydroazepino[2,1-b]quinazoline,
56) 1,3-dichloro-9,9-dimethyl-6,7,8,9,10,12-hexahydroazepino[2,1-b]quinazoline,
57) 1,3-dichloro-7,7,9,9-tetramethyl-6,7,8,9,10,12-hexahydroazepino[2,1-b]quinazoline, HCl salt, m.p. 320° C.–330° C. (dec).
58) 5-chloro-1,2,3,9-tetrahydropyrrolo[2,1-b]quinazoline,
59) 6-chloro-1,2,3,9-tetrahydropyrrolo[2,1-b]quinazoline,
60) 7-chloro-1,2,3,9-tetrahydropyrrolo[2,1-b]quinazoline,
61) 8-chloro-1,2,3,9-tetrahydropyrrolo[2,1-b]quinazoline, 62) 6,8-dichloro-1,2,3,9-tetrahydropyrrolo[2,1-b]quinazoline, HCl salt, m.p. >305° C. (dec).
63) 5,7-dichloro-1,2,3,9-tetrahydropyrrolo[2,1-b]quinazoline,
64) 5,8-dichloro-1,2,3,9-tetrahydropyrrolo[2,1-b]quinazoline,
65) 2-phenyl-1,2,3,9-tetrahydropyrrolo[2,1-b]quinazoline,
66) 6-chloro-2-phenyl-1,2,3,9-tetrahydropyrrolo[2,1-b]quinazoline,
67) 6,8-dichloro-2-phenyl-1,2,3,9-tetrahydropyrrolo[2,1-b]quinazoline,
68) 1-chloro-6,7,8,9-tetrahydro-11H-pyrido[2,1-b]quinazoline,
69) 3-chloro-6,7,8,9-tetrahydro-11H-pyrido[2,1-b]quinazoline,
70) 1,3-dichloro-6,7,8,9-tetrahydro-11H-pyrido[2,1-b]quinazoline, HCl salt, m.p. >300° C. (dec
71) 8,8-diphenyl-6,7,8,9-tetrahydro-11H-pyrido[2,1-b]quinazoline, 72) 1-chloro-8,8-diphenyl-6,7,8,9-tetrahydro-11H-pyrido[2,1-b]quinazoline,
73) 3-chloro-8,8-diphenyl-6,7,8,9-tetrahydro-11H-pyrido[2,1-b]quinazoline, HCl salt, m.p. 302° C.–305° C. (dec).
74) 1-chloro-8,8-diphenyl-7-oxa-6,7,8,9-tetrahydro-11H-pyrido[2,1-b]quinazoline,
75) 3-chloro-8,8-diphenyl-7-oxa-6,7,8,9-tetrahydro-11H-pyrido[2,1-b]quinazoline,
76) 8,8-diphenyl-7-oxa-6,7,8,9-tetrahydro-11H-pyrido[2,1-b]quinazoline,
77) 1,3-dichloro-8,8-diphenyl-6,7,8,9-tetrahydro-11H-pyrido[2,1-b]quinazoline, HCl salt, m.p. >307° C. (dec).
78) 1,3-dichloro-8,8-diphenyl-7-oxa-6,7,8,9-tetrahydro-11H-pyrido[2,1-b]quinazoline,
79) 8,8-diphenyl-6,7,8,9,10,12-hexahydroazepino[2,1-b]quinazoline,
80) 1-chloro-8,8-diphenyl-6,7,8,9,10,12-hexahydroazepino[2,1-b]quinazoline,
81) 3-chloro-8,8-diphenyl-6,7,8,9,10,12-hexahydroazepino[2,1-b]quinazoline,
82) 1,3-dichloro-8,8-diphenyl-6,7,8,9,10,12-hexahydroazepino[2,1-b]quinazoline,
83) 3-chloro-6,7,8,9,10,12-hexahydro-6,9-methanoazepino[2,1-b]quinazoline,
84) 1,3-dichloro-6,7,8,9,10,12-hexahydro-6,9-methanoazepino[2,1-b]quinazoline;
85) 2,4-dichloro-6,7,8,9,10,12-hexahydro-6,9-methanoazepino[2,1-b]quinazoline;
86) 1,4-dichloro-6,7,8,9,10,12-hexahydro-6,9-methanoazepino[2,1-b]quinazoline;
87) 3-chloro-6,7,8,9,10,12-hexahydro-7,10-methanoazepino[2,1-b]quinazoline; (±) HCl salt, m.p. 264° C.–265° C. (dec).
88) 1,3-dichloro-6,7,8,9,10,12-hexahydro-7,10-methanoazepino[2,1-b]quinazoline;
89) 2,4-dichloro-6,7,8,9,10,12-hexahydro-7,10-methanoazepino[2,1-b]quinazoline;
90) 1,4-dichloro-6,7,8,9,10,12-hexahydro-7,10-methanoazepino[2,1-b]quinazoline;
91) 3-chloro-6,7,8,9,10,12-hexahydro-6,10-methanoazepino[2,1-b]quinazoline;
92) 1,3-dichloro-6,7,8,9,10,12-hexahydro-6,10-methanoazepino[2,1-b]quinazoline; (±) HCl salt, m.p. 265° C.–268° C. (dec).
93) 2,4-dichloro-6,7,8,9,10,12-hexahydro-6,10-methanoazepino[2,1-b]quinazoline;
94) 1,4-dichloro-6,7,8,9,10,12-hexahydro-6,10-methanoazepino[2,1-b]quinazoline;
95) 1,3-dichloro-6,7,8,9-tetrahydro-11H-6,9-methanopyrido[2,1-b]quinazoline, (±) HCl salt, m.p. 261° C. (dec).
96) 1,3-dibromo-6,7,8,9,10,12-hexahydroazepino[2,1-b]quinazoline,
97) 3-bromo-6,7,8,9,10,12-hexahydroazepino[2,1-b]quinazoline,
98) 8,10-dichloro-1,2,5,11-tetrahydro-4H-[1,4]thiazepino[5,4-b]quinazoline,
99) 8,10-dichloro-1,2,5,11-tetrahydro-4H-[1,4]oxazepino[5,4-b]quinazoline,
100) 1,3-dichloro-6,9-dihydro-11H-6,9 -methanopyrido[2,1-b]quinazoline, and
101) 1,3-dichloro-2-methyl-6,7,8,9,10,12-hexahydroazepino[2,1-b]quinazoline, HCl salt, m.p. 269° C.–272° C.

EXAMPLE 10

A mixture of 10 mmol of anthranilonitrile and 20 mmol of 1-aza-2-methoxy-1-cycloheptene (1) was heated under argon to 150° C. for 48 hours. Then the excess (1) was distilled out in vacuo (11 mm Hg) and the residue was chromatographed on silica gel. 4N HCl was added to a solution of the base in absolute ethanol to give the corresponding hydrochloride in over 90% yield. This procedure was used to synthesize the following derivatives using the appropriate substituted anthranilonitrile and iminoether.
a) 1-chloro-7,8,9,10-tetrahydroazepino[2,1-b]quinazolin-12(6H)-imine,
b) 2-chloro-7,8,9,10-tetrahydroazepino[2,1-b]quinazolin-12(6H)-imine,
c) 3-chloro-7,8,9,10 -tetrahydroazepino[2,1-b] quinazolin-12(6H)-imine, m.p. 128° C.–130° C.
d) 4-chloro-7,8,9,10-tetrahydroazepino[2,1-b]quinazolin-12(6H)-imine,
e) 1-methyl-7,8,9,10-tetrahydroazepino[2,1-b]quinazolin-12(6H)-imine,
f) 2-methyl-7,8,9,10-tetrahydroazepino[2,1-b]quinazolin-12(6H)-imine,
g) 3-methyl-7,8,9,10-tetrahydroazepino[2,1-b]quinazolin-12(6H)-imine,
h) 4-methyl-7,8,9,10-tetrahydroazepino[2,1-b]quinazolin-12(6H)-imine,
i) 1-fluoro-7,8,9,10-tetrahydroazepino[2,1-b]quinazolin-12(6H)-imine,
j) 2-fluoro-7,8,9,10-tetrahydroazepino[2,1-b]quinazolin-12(6H)-amine,
k) 3-fluoro-7,8,9,10-tetrahydroazepino[2,1-b]quinazolin-12(6H)-amine,
l) 4-fluoro-7,8,9,10-tetrahydroazepino[2,1-b]quinazolin-12(6H)-amine,
m) 1,3-dichloro-7,8,9,10-tetrahydroazepino[2,1-b]quinazolin-12(6H)-imine,
n) 1,2-dichloro-7,8,9,10-tetrahydroazepino[2,1-b]quinazolin-12(6H)-imine,
o) 2,3-dichloro-7,8,9,10-tetrahydroazepino[2,1-b]quinazolin-12(6H)-imine,
p) 1,4-dichloro-7,8,9,10-tetrahydroazepino[2,1-b]quinazolin-12(6H)-imine,
q) 2,4-dichloro-7,8,9,10-tetrahydroazepino[2,1-b]quinazolin-12(6H)-imine,
r) 3-chloro-1-methyl-7,8,9,10-tetrahydroazepino[2,1-b]quinazolin-12(6H)-imine,
s) 1,3-dichloro-6,7,8,9-tetrahydro-11H-pyrido[2,1-b]quinazolin-11-imine,
t) 3-chloro-6,7,8,9-tetrahydro-11H-pyrido[2,1-b]quinazolin-11-imine,
u) 1-chloro-6,7,8,9-tetrahydro-11H-pyrido[2,1-b]quinazolin-11-imine, v) 6,8-dichloro-2,3-dihydropyrrolo[2,1-b]quinazolin-9(1H)-imine,
w) 6-chloro-2,3-dihydropyrrolo[2,1-b]quinazolin-9(1H)-imine,
x) 8-chloro-2,3-dihydropyrrolo[2,1-b]quinazolin-9(1H)-imine, and
y) 3-(trifluoromethyl)-7,8,9,10-tetrahydroazepino[2,1-b]quinazolin-12(6H)]imine, m.p. 101° C.–102° C.

EXAMPLE 11

1,3-dichloro-11H-pyrido[2,1-b]quinazolin-11-imine

Ten grams of 4,6-dichloro-2-nitroaniline (Aldrich Chemical Co.) was dissolved in 100 mL of anhydrous diethyl ether and cooled in an ice bath so that the internal temperature was between 5° C.–10° C. throughout the reaction. To this yellow solution was added 15 mL of 60% aqueous tetrafluoroboric acid (Aldrich Chemical Co.) and to this vigorously stirred solution was added in small portions 18 g of solid nitrosylsulfuric acid over a period of 4 hours. Then 10 mL of absolute ethanol was added and the white crystalline solid diazonium salt was filtered off with suction and washed twice with 60 mL diethyl ether and all of the solvent was removed by suction on the Buchner funnel. The filter cake was wetted immediately with 10 mL of saturated aqueous solution of sodium tetrafluoroborate. This paste was then added in small portions to a vigorously stirred mixture of 35 g of cuprous cyanide and 22 g of potassium cyanide in 300 mL of water. After the exothermic reaction subsided, the mixture was stirred 1 hour at room temperature and then briefly warmed to 60° C. Then it was filtered and the solids as well as the filtrate were extracted with chloroform 4×100 mL. The extract was dried with anhydrous magnesium sulfate and concentrated in vacuo to give 6.8 g of light brown solid 2-nitro-4,6-dichlorobenzonitrile, reasonably pure for the further transformation. Chromatography 4:1 chloroform/hexane followed by recrystallization from diethyl ether gave pure 4,6-dichloro-2-nitrobenzonitrile, with m.p. 102°–103° C. (Diazotization of 4,6-dichloro-2-nitroaniline in large excess of sulfuric acid, followed by reaction with CuCN/KCN in aqueous media by the methodology described by Atkinson, C. M. and Simpson, J. C. E., *J. Chem. Soc.*, 1947:232, produced only very erratic results). The 4,6-dichloro-2-aminobenzonitrile was prepared by reduction of the above 2-nitro-4,6-dichlorobenzonitrile with stannous chloride using analogous conditions to those described by R. L. Mckee, M. K. Mckee, and R. W. Bost in *J. Am. Chem. Soc.* 69:940 (1947), and found to have m.p. 140°–141° C. Five grams of 4,6-dichloro-2-aminobenzonitrile and 6 mL of 2-chloropyridine in 20 mL of chlorobenzene were heated to boil until the reaction was judged complete by TLC (300:20:1 chloroform/methanol/28% aqueous ammonia). The excess solvent was removed in vacuo and the residue was distributed between 100 mL 10% aqueous sodium carbonate and chloroform. The chloroform layer was dried with anhydrous potassium carbonate, filtered, and the residue was column chromatographed on silica gel, using the above solvent as eluent. Concentration of the appropriate fractions yielded the 1,3-dichloro-11H-pyrido[2,1-b]quinazolin-11-imine as yellowish solid.

The above methodology is used to prepare the following compounds by heating the appropriately substituted 2-aminobenzonitrile derivative with the appropriately substituted 2-chloro-(or 2-fluoro- or 2-bromopyridine derivative) in the absence of a solvent or in the presence of solvent such as toluene, chlorobenzene, o-dichlorobenzene, anisole, 1,3-dimethoxybenzene, phenol and the like:

1-methyl-11H-pyrido[2,1-b]quinazolin-11-imine,
2-methyl-11H-pyrido[2,1-b]quinazolin-11-imine,
3-methyl-11H-pyrido[2,1-b]quinazolin-11-imine,
4-methyl-11H-pyrido[2,1-b]quinazolin-11-imine,
1-chloro-11H-pyrido[2,1-b]quinazolin-11-imine,
2-chloro-11H-pyrido[2,1-b]quinazolin-11-imine,
3-chloro-11H-pyrido[2,1-b]quinazolin-11-imine,
4-chloro-11H-pyrido[2,1-b]quinazolin-11-imine,
1-fluoro-11H-pyrido[2,1-b]quinazolin-11-imine,
2-fluoro-11H-pyrido[2,1-b]quinazolin-11-imine,
3-fluoro-11H-pyrido[2,1-b]quinazolin-11-imine,
4-fluoro-11H-pyrido[2,1-b]quinazolin-11-imine,
1-bromo-11H-pyrido[2,1-b]quinazolin-11 -imine,
2-bromo-11H-pyrido[2,1-b]quinazolin-11-imine,
3-bromo-11H-pyrido[2,1-b]quinazolin-11-imine,
4-bromo-11H-pyrido[2,1-b]quinazolin-11-imine,
1-(trifluoromethyl)-11H-pyrido[2,1-b]quinazolin-11-imine,
2-(trifluoromethyl)-11H-pyrido[2,1-b]quinazolin-11-imine,
3-(trifluoromethyl)-11H-pyrido[2,1-b]quinazolin-11-imine,
4-(trifluoromethyl)-11H-pyrido[2,1-b]quinazolin-11-imine,
1-(methylthio)-11H-pyrido[2,1-b]quinazolin-11-imine,
2-(methylthio)-11H-pyrido[2,1-b]quinazolin-11-imine,
3-(methylthio)-11H-pyrido[2,1-b]quinazolin-11-imine,
4-(methylthio)-11H-pyrido[2,1-b]quinazolin-11-imine,
1,2-dichloro-11H-pyrido[2,1-b]quinazolin-11-imine,
1,3-dichloro-11H-pyrido[2,1-b]quinazolin-11-imine,
1,4-dichloro-11H-pyrido[2,1-b]quinazolin-11-imine
2,3-dichloro-11H-pyrido[2,1-b]quinazolin-11-imine,
2,4-dichloro-11H-pyrido[2,1-b]quinazolin-11-imine,
3,4-dichloro-11H-pyrido[2,1-b]quinazolin-11-imine,
1,3-dimethoxy-11H-pyrido[2,1-b]quinazolin-11-imine,
2,3-dimethoxy-11H-pyrido[2,1-b]quinazolin-11-imine,
2,4-dimethoxy-11H-pyrido[2,1-b]quinazolin-11-imine,
3,4-dimethoxy-11H-pyrido[2,1-b]quinazolin-11-imine,
1,2-dimethyl-11H-pyrido[2,1-b]quinazolin-11-imine,
1,3-dimethyl-11H-pyrido[2,1-b]quinazolin-11-imine,
1,4-dimethyl-11H-pyrido[2,1-b]quinazolin-11-imine,
2,3-dimethyl-11H-pyrido[2,1-b]quinazolin-11-imine,
2,4-dimethyl-11H-pyrido[2,1-b]quinazolin-11-imine,
3,4-dimethyl-11H-pyrido[2,1-b]quinazolin-11-imine,
2-(methylcarbamoyloxy)-11H-pyrido[2,1-b]quinazolin-11-imine,
1-chloro-2-(methylcarbamoyloxy)-11H-pyrido[2,1-b]quinazolin-11-imine,
3-chloro-2-(methylcarbamoyloxy)-11H-pyrido[2,1-b]quinazolin-11-imine,
1-chloro-3-(methylcarbamoyloxy)-11H-pyrido[2,1-b]quinazolin-11-imine,
2-(heptylcarbamoyloxy)-11H-pyrido[2,1-b]quinazolin-11-imine,
3-(heptylcarbamoyloxy)-11H-pyrido[2,1-b]quinazolin-11-imine,
1-chloro-3-(heptylcarbamoyloxy)-11H-pyrido[2,1-b]quinazolin-11-imine,
3-chloro-2-(heptylcarbamoyloxy)-11H-pyrido[2,1-b]quinazolin-11-imine,
1,3-dichloro-2-(heptylcarbamoyloxy)-11H-pyrido[2,1-b]quinazolin-11-imine,
1-chloro-3-methyl-11H-pyrido[2,1-b]quinazolin-11-imine,
1-methyl-3-chloro-11H-pyrido[2,1-b]quinazolin-11-imine,
1,3-dichloro-11H-pyrido[2,1-b]quinazolin-11-methylamine,
1,3-dichloro-11H-pyrido[2,1-b]quinazolin-11-(2-phenylethyl)-imine,
1,3-difluoro-11H-pyrido[2,1-b]quinazolin-11-imine,
1-fluoro-3-bromo-11H-pyrido[2,1-b]quinazolin-11-imine,
1-fluoro-3-iodo-11H-pyrido[2,1-b]quinazolin-11-imine,
1-chloro-3-fluoro-11H-pyrido[2,1-b]quinazolin-11-imine, 1-chloro-3-bromo-11H-pyrido[2,1-b]quinazolin-11-imine,
1-chloro-3-iodo-11H-pyrido[2,1-b]quinazolin-11-imine,
1-bromo-3-fluoro-11H-pyrido[2,1-b]quinazolin-11-imine,
1-bromo-3-chloro-11H-pyrido[2,1-b]quinazolin-11-imine,
1-bromo-3-iodo-11H-pyrido[2,1-b]quinazolin-11-imine,
1,3-dibromo-11H-pyrido[2,1-b]quinazolin-11-imine,
1-iodo-3-fluoro-11H-pyrido[2,1-b]quinazolin-11-imine,
1-iodo-3-chloro-11H-pyrido[2,1-b]quinazolin-11-imine,
1-iodo-3-bromo-11H-pyrido[2,1-b]quinazolin-11-imine,
1,3-diiodo-11H-pyrido[2,1-b]quinazolin-11-imine,
1,3-dichloro-6-methyl-11H-pyrido[2,1-b]quinazolin-11-imine,
1,3-dichloro-7-methyl-11H-pyrido[2,1-b]quinazolin-11-imine,
1,3-dichloro-8-methyl-11H-pyrido[2,1-b]quinazolin-11-imine,
1,3-dichloro-9-methyl-11H-pyrido[2,1-b]quinazolin-11-imine,
1,3-dichloro-6-fluoro-11H-pyrido[2,1-b]quinazolin-11-imine,
1,3-dichloro-7-fluoro-11H-pyrido[2,1-b]quinazolin-11-imine,
1,3-dichloro-8-fluoro-11H-pyrido[2,1-b]quinazolin-11-imine,
1,3-dichloro-9-fluoro-11H-pyrido[2,1-b]quinazolin-11-imine,
1,3,6-trichloro-11H-pyrido[2,1-b]quinazolin-11-imine,
1,3,7-trichloro-11H-pyrido[2,1-b]quinazolin-11-imine,
1,3,8-trichloro-11H-pyrido[2,1-b]quinazolin-11-imine, or
1,3,9-trichloro-11H-pyrido[2,1-b]quinazolin-11-imine.

EXAMPLE 12

1,3-dichloro-6,7,8,9,10,11,12,14-octahydro-6,10:8,12-dimethanoazonino[2,1-b]quinazoline To 30 g of 2-adamantanone (Aldrich Chem. Co.) in 100 mL of methanol was added 50 g of hydroxylamine hydrochloride and 92 g of sodium acetate trihydrate and the mixture was refluxed for 2 hours. The mixture was concentrated in vacuo, the residue was distributed between 250 of dichloromethane and 50 mL of water. The organic layer was separated, dried with magnesium sulfate and concentrated in vacuo to give 30 g of crude 2-adamantanone oxime. This was dissolved in 100 mL of chloroform and 135 g of PPE (polyphosphate ester, prepared by refluxing phosphorus pentoxide with diethyl ether in chloroform, as described by G. Schramm, H. Groetsch, and W. Pollmann, Angew. Chem., Internat. Ed., 1,1 (1962)) was added carefully. When the exothermic reaction ceased, the mixture was refluxed for 5 minutes. Then it was cool in ice, diluted with 500 mL of water and stirred overnight. The organic layer was separated, dried with magnesium sulfate and concentrated in vacuo to give 16.6 g of the crude lactam product. This was dissolved in 250 of chloroform and 11 mL of phosphorus oxychloride was added dropwise in 30 minutes. To this was then added a solution of 15 g of 4,6-dichloroanthranilic acid and 4 of triethylamine in 150 mL of chloroform in 25 minute at room temperature. Then the mixture was refluxed for 16 hours. Column chromatography using 50:1 to 25:1 chloroform-:methanol on silica gel provided 16 g of 1,3-dichloro-7,8,9,10,11,12-hexahydro-6,10:8,12-dimethanoazonino[2,1-b]quinazolin-14(6H)-one as white coarse crystals. This was then reduced with zinc and hydrochloric acid to the 1,3-dichloro-6,7,8,9,10,11,12,14-octahydro-6,10:8,12-dimethanoazonino[2,1-b]quinazoline by the same procedure as described in Example 2 to give after treatment with 1 equivalent of HCl and recrystallization from absolute alcohol/ethyl acetate 1,3-dichloro-6,7,8,9,10,11,12,14-octahydro-6,10:8,12-dimethanoazonino[2,1-b]quinazoline monohydrochloride as white crystalline solid, with m.p. 310° C. (dec.).

By the above procedure are prepared the following compounds:

1-methyl-6,7,8,9,10,11,12,14-octahydro-6,10:8,12-dimethanoazonino[2,1-b]quinazoline,
2-methyl-6,7,8,9,10,11,12,14-octahydro-6,10:8,12-dimethanoazonino[2,1-b]quinazoline,
3-methyl-6,7,8,9,10,11,12,14-octahydro-6,10:8,12-dimethanoazonino[2,1-b]quinazoline,
4-methyl-6,7,8,9,10,11,12,14-octahydro-6,10:8,12 dimethanoazonino[2,1-b]quinazoline,
1-chloro-6,7,8,9,10,11,12,14-octahydro-6,10:8,12-dimethanoazonino[2,1-b]quinazoline,
2-chloro-6,7,8,9,10,11,12,14-octahydro-6,10:8,12-dimethanoazonino[2,1-b]quinazoline,
3-chloro-6,7,8,9,10,11,12,14-octahydro-6,10:8,12-dimethanoazonino[2,1-b]quinazoline,
4-chloro-6,7,8,9,10,11,12,14-octahydro-6,10:8,12-dimethanoazonino[2,1-b]quinazoline,
1-fluoro-6,7,8,9,10,11,12,14-octahydro-6,10:8,12-dimethanoazonino[2,1-b]quinazoline,
3-fluoro-6,7,8,9,10,11,12,14-octahydro-6,10:8,12-dimethanoazonino[2,1-b]quinazoline,
1-bromo-6,7,8,9,10,11,12,14-octahydro-6,10:8,12-dimethanoazonino[2,1-b]quinazoline,
2-bromo-6,7,8,9,10,11,12,14-octahydro-6,10:8,12-dimethanoazonino[2,1-b]quinazoline,
3-bromo-6,7,8,9,10,11,12,14-octahydro-6,10:8,12-dimethanoazonino[2,1-b]quinazoline,
4-bromo-6,7,8,9,10,11,12,14-octahydro-6,10:8,12-dimethanoazonino[2,1-b]quinazoline-1-(trifluoromethyl)-6,7,8,9,10,11,12,14-octahydro-6,10:8,12-dimethanoazonino[2,1-b]quinazoline, 2-(trifluoromethyl)-6,7,8,9,10,11,12,14-octahydro-6,10:8,12-dimethanoazonino[2,1-b]quinazoline,
3-(trifluoromethyl)-6,7,8,9,10,11,12,14-octahydro-6,10:8,12-dimethanoazonino[2,1-b]quinazoline,
4-(trifluoromethyl)-6,7,8,9,10,11,12,14-octahydro-6,10:8,12-dimethanoazonino[2,1-b]quinazoline,
1,2-dichloro-6,7,8,9,10,11,12,14-octahydro-6,10:8,12-dimethanoazonino[2,1-b]quinazoline,
1,3-dichloro-6,7,8,9,10,11,12,14-octahydro-6,10:8,12-dimethanoazonino[2,1-b]quinazoline,
1,4-dichloro-6,7,8,9,10,11,12,14-octahydro-6,10:8,12-dimethanoazonino[2,1-b]quinazoline,
2,3-dichloro-6,7,8,9,10,11,12,14-octahydro-6,10:8,12-dimethanoazonino[2,1-b]quinazoline,
2,4-dichloro-6,7,8,9,10,11,12,14-octahydro-6,10:8,12-dimethanoazonino[2,1-b]quinazoline,
3,4-dichloro-6,7,8,9,10,11,12,14-octahydro-6,10:8,12-dimethanoazonino[2,1-b]quinazoline,
2,3-dimethoxy-6,7,8,9,10,11,12,14-octahydro-6,10:8,12-dimethanoazonino[2,1-b]quinazoline,
2-(methylcarbamoyloxy)-6,7,8,9,10,11,12,14-octahydro-6,10:8,12-dimethanoazonino[2,1-b]quinazoline,
1-chloro-2-(methylcarbamoyloxy)-6,7,8,9,10,11,12,14-octahydro-6,10:8,12-dimethanoazonino[2,1-b]quinazoline,
3-chloro-2-(methylcarbamoyloxy)-6,7,8,9,10,11,12,14-octahydro-6,10:8,12-dimethanoazonino[2,1-b]quinazoline,
1-chloro-3-(methylcarbamoyloxy)-6,7,8,9,10,11,12,14-octahydro-6,10:8,12-dimethanoazonino[2,1-b]quinazoline,
2-(heptylcarbamoyloxy)-6,7,8,9,10,11,12,14-octahydro-6,10:8,12-dimethanoazonino[2,1-b]quinazoline,
3-(heptylcarbamoyloxy)-6,7,8,9,10,11,12,14-octahydro-6,10:8,12-dimethanoazonino[2,1-b]quinazoline, 1-chloro-3-(heptylcarbamoyloxy)-6,7,8,9,10,11,12,14-octahydro-6,10:8,12-dimethanoazonino[2,1-b]quinazoline,
3-chloro-2-(heptylcarbamoyloxy)-6,7,8,9,10,11,12,14-octahydro-6,10:8,12-dimethanoazonino[2,1-b]quinazoline,
1,3-dichloro-4-methyl-6,7,8,9,10,11,12,14-octahydro-6,10:8,12-dimethanoazonino[2,1-b]quinazoline,
1,3-dichloro-2,4-dimethyl-11H-pyrido[2,1-b]quinazoline,
1,3-difluoro-11H-6,7,8,9,10,11,12,14-octahydro-6,10:8,12-dimethanoazonino[2,1-b]quinazoline,
1-fluoro-3-chloro-6,7,8,9,10,11,12,14-octahydro-6,10:8,12-dimethanoazonino[2,1-b]quinazoline,
1-fluoro-3-bromo-6,7,8,9,10,11,12,14-octahydro-6,10:8,12-dimethanoazonino[2,1-b]quinazoline,
1-fluoro-3-iodo-6,7,8,9,10,11,12,14-octahydro-6,10:8,12-dimethanoazonino[2,1-b]quinazoline,
1-chloro-3-fluoro-6,7,8,9,10,11,12,14-octahydro-6,10:8,12-dimethanoazonino[2,1-b]quinazoline,
1-chloro-3-bromo-6,7,8,9,10,11,12,14-octahydro-6,10:8,12-dimethanoazonino[2,1-b]quinazoline,
1-chloro-3-iodo-11H-6,7,8,9,10,11,12,14-octahydro-6,10:8,12-dimethanoazonino[2,1-b]quinazoline,
1-bromo-3-fluoro-6,7,8,9,10,11,12,14-octahydro-6,10:8,12-dimethanoazonino[2,1-b]quinazoline,
1-bromo-3-chloro-6,7,8,9,10,11,12,14-octahydro-6,10:8,12-dimethanoazonino[2,1-b]quinazoline,
1-bromo-3-iodo-6,7,8,9,10,11,12,14-octahydro-6,10:8,12-dimethanoazonino[2,1-b]quinazoline,
1,3-dibromo-6,7,8,9,10,11,12,14-octahydro-6,10:8,12-dimethanoazonino[2,1-b]quinazoline,
1-iodo-3-fluoro-6,7,8,9,10,11,12,14-octahydro-6,10:8,12-dimethanoazonino[2,1-b]quinazoline,
1-iodo-3-chloro-6,7,8,9,10,11,12,14-octahydro-6,10:8,12-dimethanoazonino[2,1-b]quinazoline,
1-iodo-3-bromo-6,7,8,9,10,11,12,14-octahydro-6,10:8,12-dimethanoazonino[2,1-b]quinazoline, and
1,3-diiodo-6,7,8,9,10,11,12,14-octahydro-6,10:8,12-dimethanoazonino[2,1-b]quinazoline.

EXAMPLE 13

1,3-dichloro-7,8,9,10,11,12-hexahydro-6,10:8,12-dimethanoazonino[2,1-b]quinazolin-14(6H)-imine To 30 g of 2-adamantanone (Aldrich Chem. Co.) in 100 mL of methanol was added 50 g of hydroxylamine hydrochloride and 92 g of sodium acetate trihydrate and the mixture was refluxed for 2 hours. The mixture was concentrated in vacuo, the residue was distributed between 250 mL of dichloromethane and 50 mL of water. The organic layer was separated, dried with magnesium sulfate and concentrated in vacuo to give 30 g of crude 2-adamantanone oxime. This was dissolved in 100 mL of chloroform and 135 g of PPE (polyphosphate ester, prepared by refluxing phosphorus pentoxide with diethyl ether in chloroform, as described by G. Schramm, H. Groetsch, and W. Pollmann, Angew. Chem., Internat. Ed., 1,1 (1962)) was added carefully. When the exothermic reaction ceased, the mixture was refluxed for 5 minute. Then it was cooled in ice, diluted with 500 mL of water and stirred overnight. The organic layer was separated, dried with magnesium sulfate and concentrated in vacuo to give 16.6 g of the crude lactam product. This was dissolved in 250 mL of chloroform and 11 mL of phosphorus oxychloride was added dropwise in 30 minutes. After stirring for additional 1 hour at room temperature, to this stirred mixture was added 25 mL of triethylamine and a solution of 16 g of 4,6-dichloro-2-aminobenzonitrile (4,6-dichloroanthranilonitrile) which was prepared by the methodology shown in Example 11.

The reaction mixture was stirred at room temperature for 12 hours, followed by reflux for 24 hours. Then the reaction mixture was treated with 500 mL of 15% aqueous potassium carbonate, the organic layer was separated, dried with anhydrous potassium carbonate and concentrated in vacuo. The dark brown residue was column chromatographed using 300:25:1 chloroform:methanol: 28% aqueous ammonia on silica gel. The corresponding fractions yielded the 1,3-dichloro-7,8,9,10,11,12-hexahydro-6,10:8,12-dimethanoazonino[2,1-b]quinazolin-14(6H)-imine as a light tan solid.

By the above procedure are prepared the following compounds:
1-methyl-7,8,9,10,11,12-hexahydro-6,10:8,12-dimethanoazonino[2,1-b]quinazolin-14(6H)-imine,
2-methyl-7,8,9,10,11,12-hexahydro-6,10:8,12-dimethanoazonino[2,1-b]quinazolin-14(6H)-imine,
3-methyl-7,8,9,10,11,12-hexahydro-6,10:8,12-dimethanoazonino[2,1-b]quinazolin-14(6H)-imine,
4-methyl-7,8,9,10,11,12-hexahydro-6,10:8,12-dimethanoazonino[2,1-b]quinazolin-14(6H)-imine,
1-chloro-7,8,9,10,11,12-hexahydro-6,10:8,12-dimethanoazonino[2,1-b]quinazolin-14(6H)-imine,
2-chloro-7,8,9,10,11,12-hexahydro-6,10:8,12-dimethanoazonino[2,1-b]quinazolin-14(6H)-imine,
3-chloro-7,8,9,10,11,12-hexahydro-6,10:8,12-dimethanoazonino[2,1-b]quinazolin-14(6H)-imine,
4-chloro-7,8,9,10,11,12-hexahydro-6,10:8,12-dimethanoazonino[2,1-b]quinazolin-14(6H)-imine,
1-fluoro-7,8,9,10,11,12-hexahydro-6,10:8,12-dimethanoazonino[2,1-b]quinazolin-14(6H)-imine,
3-fluoro-7,8,9,10,11,12-hexahydro-6,10:8,12-dimethanoazonino[2,1-b]quinazolin-14(6H)-imine,
1-bromo-7,8,9,10,11,12-hexahydro-6,10:8,12-dimethanoazonino[2,1-b]quinazolin-14(6H)-imine,
2-bromo-7,8,9,10,11,12-hexahydro-6,10:8,12-dimethanoazonino[2,1-b]quinazolin-14(6H)-imine,
3-bromo-7,8,9,10,11,12-hexahydro-6,10:8,12-dimethanoazonino[2,1-b]quinazolin-14(6H)-imine,
4-bromo-7,8,9,10,11,12-hexahydro-6,10:8,12-dimethanoazonino[2,1-b]quinazolin-14(6H)-imine,
1-(trifluoromethyl)-7,8,9,10,11,12-hexahydro-6,10:8,12-dimethanoazonino[2,1-b]quinazolin-14(6H)-imine,
2-(trifluoromethyl)-7,8,9,10,11,12-hexahydro-6,10:8,12-dimethanoazonino[2,1-b]quinazolin-14(6H)-imine,
3-(trifluoromethyl)-7,8,9,10,11,12-hexahydro-6,10:8,12-dimethanoazonino[2,1-b]quinazolin-14(6H)-imine,
4-(trifluoromethyl)-7,8,9,10,11,12-hexahydro-6,10:8,12-dimethanoazonino[2,1-b]quinazolin-14(6H)-imine,
1,2-dichloro-7,8,9,10,11,12-hexahydro-6,10:8,12-dimethanoazonino[2,1-b]quinazolin-14(6H)-imine,
1,3-dichloro-7,8,9,10,11,12-hexahydro-6,10:8,12-dimethanoazonino[2,1-b]quinazolin-14(6H)-imine,
1,4-dichloro-7,8,9,10,11,12-hexahydro-6,10:8,12-dimethanoazonino[2,1-b]quinazolin-14(6H)-imine,
2,3-dichloro-7,8,9,10,11,12-hexahydro-6,10:8,12-dimethanoazonino[2,1-b]quinazolin-14(6H)-imine,
2,4-dichloro-6,7,8,9,10,11,12-hexahydro-6,10:8,12-dimethanoazonino[2,1-b]quinazolin-14(6H)-imine,
3,4-dichloro-7,8,9,10,11,12-hexahydro-6,10:8,12-dimethanoazonino[2,1-b]quinazolin-14(6H)-imine,
2,3-dimethoxy-7,8,9,10,11,12-hexahydro-6,10:8,12-dimethanoazonino[2,1-b]quinazolin-14(6H)-imine,
2-(methylcarbamoyloxy)-7,8,9,10,11,12-hexahydro-6,10:8,12-dimethanoazonino[2,1-b]quinazolin-14(6H)-imine,
1-chloro-2-(methylcarbamoyloxy)-7,8,9,10,11,12-hexahydro-6,10:8,12-dimethanoazonino[2,1-b]quinazolin-14(6H)-imine, 3-chloro-2-(methylcarbamoyloxy)-7,8,9,10,11,12-hexahydro-6,10:8,12-dimethanoazonino[2,1-b]quinazolin-14(6H)-imine, 1-chloro-3-(methylcarbamoyloxy)-7,8,9,10,11,12-hexahydro-6,10:8,12-dimethanoazonino[2,1-b]quinazolin-14(6H)-imine, 2-(heptylcarbamoyloxy)-7,8,9,10,11,12-hexahydro-6,10:8,12-dimethanoazonino[2,1-b]quinazolin-14(6H)-imine, 3-(heptylcarbamoyloxy)-7,8,9,10,11,12-hexahydro-6,10:8,12-dimethanoazonino[2,1-b]quinazolin-14(6H)-imine, 1-chloro-3-(heptylcarbamoyloxy)-7,8,9,10,11,12-hexahydro-6,10:8,12-dimethanoazonino[2,1-b]quinazolin-14(6H)-imine, 3-chloro-2-(heptylcarbamoyloxy)-7,8,9,10,11,12-hexahydro-6,10:8,12-dimethanoazonino[2,1-b]quinazolin-14(6H)-imine, 1,3-dichloro-4-methyl-7,8,9,10,11,12-hexahydro-6,10:8,12-dimethanoazonino[2,1-b]quinazolin-14(6H)-imine, 1,3-difluoro-11H-7,8,9,10,11,12-hexahydro-6,10:8,12-dimethanoazonino[2,1-b]quinazolin-14(6H)-imine, 1-fluoro-3-chloro-7,8,9,10,11,12-hexahydro-6,10:8,12-dimethanoazonino[2,1-b]quinazolin-14(6H)-imine, 1-fluoro-3-bromo-7,8,9,10,11,12-hexahydro-6,10:8,12-dimethanoazonino[2,1-b]quinazolin-14(6H)-imine, 1-fluoro-3-iodo-7,8,9,10,11,12-hexahydro-6,10:8,12-dimethanoazonino[2,1-b]quinazolin-14(6H)-imine, 1-chloro-3-fluoro-7,8,9,10,11,12-hexahydro-6,10:8,12-dimethanoazonino[2,1-b]quinazolin-14(6H)-imine, 1-chloro-3-bromo-7,8,9,10,11,12-hexahydro-6,10:8,12-dimethanoazonino[2,1-b]quinazolin-14(6H)-imine, 1-chloro-3-iodo-11H-7,8,9,10,11,12-hexahydro-6,10:8,12-dimethanoazonino[2,1-b]quinazolin-14(6H)-imine, 1-bromo-3-fluoro-7,8,9,10,11,12-hexahydro-6,10:8,12-dimethanoazonino[2,1-b]quinazolin-14(6H)-imine, 1-bromo-3-chloro-7,8,9,10,11,12-hexahydro-6,10:8,12-dimethanoazonino[2,1-b]quinazolin-14(6H)-imine, 1-bromo-3-iodo-7,8,9,10,11,12-hexahydro-6,10:8,12-dimethanoazonino[2,1-b]quinazolin-14(6H)-imine, 1,3-dibromo-7,8,9,10,11,12-hexahydro-6,10:8,12-dimethanoazonino[2,1-b]quinazolin-14(6H)-imine, 1-iodo-3-fluoro-7,8,9,10,11,12-hexahydro-6,10:8,12-dimethanoazonino[2,1-b]quinazolin-14(6H)-imine, 1-iodo-3-chloro-7,8,9,10,11,12-hexahydro-6,10:8,12-dimethanoazonino(2,1-b]quinazolin-14(6H)-imine, 1-iodo-3-bromo-7,8,9,10,11,12-hexahydro-6,10:8,12-dimethanoazonino[2,1-b]quinazolin-14(6H)-imine and, 1,3-diiodo-7,8,9,10,11,12-hexahydro-6,10:8,12-dimethanoazonino[2,1-b]quinazolin-14(6H)]imine.

EXAMPLE 14

1,3-dichloro-11H-pyrido[2,1-b]quinazoline

Twenty-five grams of 4,6-dichloroanthranilic acid was added portionwise to 250 mL of methanol, saturated with anhydrous HCl at 0° C. with vigorous stirring. The mixture was then stirred at room temperature for 24 hours. Then the mixture was stirred at 60° C. for 12 hours. Then the excess solvent was removed in vacuo into a cold trap and the residue was distributed between 100 mL of chloroform and 250 mL of 10% aqueous sodium carbonate. The organic layer was separated and dried with anhydrous magnesium sulfate. After concentration in vacuo the residue was dissolved in 150 mL of dry THF and added dropwise into a solution of 20 g of lithium aluminum hydride in 500 mL of anhydrous THF in 30 minutes at 10° C. Then the mixture was stirred at room temperature for I hour and then cooled in ice-salt bath and decomposed with saturated aqueous potassium carbonate. The precipitate was filtered off and the filtrate was dried with anhydrous magnesium sulfate, filtered and concentrated in vacuo. The residue was added portionwise into concentrated hydrochloric acid through which a gentle stream of hydrogen chloride was passed. The mixture was warmed to 60° C. At the end of the reaction the solid that formed was collected and dried in a stream of nitrogen.

Five grams of the above solid 4,6-dichloro-2-aminobenzyl chloride hydrochloride was heated with 10 mL of 2-chloropyridine in 25 mL of chlorobenzene. The reaction was followed by TLC (300:20:1 chloroform/methanol/28% aqueous ammonia). When the reaction was complete, the reaction mixture was concentrated in vacuo (cold trap). The residue was basified with saturated aqueous potassium carbonate and distributed between 50 mL of chloroform and 50 mL of water. The chloroform layer was separated, dried with anhydrous potassium carbonate and concentrated in vacuo. The brown residue was chromatographed using the above solvent system and the appropriate fractions were concentrated in vacuo to give a yellow solid. This was treated with one equivalent of 4N hydrochloric acid and coevaporated with 50 mL of absolute ethanol. The residue was recrystallized from absolute ethanol-ethyl acetate mixture to give the hydrochloride of 1,3-dichloro-11H-pyrido[2,1-b]quinazoline.

The above methodology is used to prepare the following compounds by heating the appropriately substituted 2-aminobenzyl chloride derivative hydrochloride with the appropriately substituted 2-chloro- (or 2-fluoro-or 2-bromopyridine derivative) in the absence of a solvent or in the presence of solvent such as toluene, chlorobenzene, dichlorobenzene, anisole, 1,3-dimethoxybenzene, phenol and the like.

1-methyl-11H-pyrido[2,1-b]quinazoline,
2-methyl-11H-pyrido[2,1-b]quinazoline,
3-methyl-11H-pyrido[2,1-b]quinazoline,
4-methyl-11H-pyrido[2,1-b]quinazoline,
1-chloro-11H-pyrido[2,1-b]quinazoline,
2-chloro-11H-pyrido[2,1-b]quinazoline,
3-chloro-11H-pyrido[2,1-b]quinazoline,
4-chloro-11H-pyrido[2,1-b]quinazoline,
1-fluoro-11H-pyrido[2,1-b]quinazoline,
2-fluoro-11H-pyrido(2,1-b]quinazoline,
3-fluoro-11H-pyrido[2,1-b]quinazoline,
4-fluoro-11H-pyrido[2,1-b]quinazoline,
1-bromo-11H-pyrido[2,1-b]quinazoline,
2-bromo-11H-pyrido[2,1-b]quinazoline,
3-bromo-11H-pyrido[2,1-b]quinazoline,
4-bromo-11H-pyrido[2,1-b]quinazoline,
1-(trifluoromethyl)-11H-pyrido[2,1-b]quinazoline,
2-(trifluoromethyl)-11H-pyrido[2,1-b]quinazoline,
3-(trifluoromethyl)-11H-pyrido[2,1-b]quinazoline,
4-(trifluoromethyl)-11H-pyrido[2,1-b]quinazoline,
1-(methylthio)-11H-pyrido[2,1-b]quinazoline,
2-(methylthio)-11H-pyrido[2,1-b]quinazoline,
3-(methylthio)-11H-pyrido[2,1-b]quinazoline,
4-(methylthio)-11H-pyrido[2,1-b]quinazoline,
1,2-dichloro-11H-pyrido[2,1-b]quinazoline,
1,3-dichloro-11H-pyrido[2,1-b]quinazoline,
1,4-dichloro-11H-pyrido[2,1-b]quinazoline,
2,3-dichloro-11H-pyrido[2,1-b]quinazoline,
2,4-dichloro-11H-pyrido[2,1-b]quinazoline,
3,4-dichloro-11H-pyrido[2,1-b]quinazoline,
1,3-dimethoxy-11H-pyrido[2,1-b]quinazoline,
2,3-dimethoxy-11H-pyrido[2,1-b]quinazoline,
2,4-dimethoxy-11H-pyrido[2,1-b]quinazoline,
3,4-dimethoxy-11H-pyrido[2,1-b]quinazoline,
1,2-dimethyl-11H-pyrido[2,1-b]quinazoline, 1,3-dimethyl-11H-pyrido[2,1-b]quinazoline,
1,4-dimethyl-11H-pyrido[2,1-b]quinazoline,
2,3-dimethyl-11H-pyrido[2,1-b]quinazoline,
2,4-dimethyl-11H-pyrido[2,1-b]quinazoline,
3,4-dimethyl-11H-pyrido[2,1-b]quinazoline,
2-(methylcarbamoyloxy)-11H-pyrido[2,1-b]quinazoline,
1-chloro-2-(methylcarbamoyloxy)-11H-pyrido(2,1-b]quinazoline,
3-chloro-2-(methylcarbamoyloxy)-11H-pyrido[2,1-b]quinazoline,
1-chloro-3-(methylcarbamoyloxy)-11H-pyrido[2,1-b]quinazoline,
2-(heptylcarbamoyloxy)-11H-pyrido[2,1-b]quinazoline,
3-(heptylcarbamoyloxy)-11H-pyrido[2,1-b]quinazoline,
1-chloro-3-(heptylcarbamoyloxy)-11H-pyrido[2,1-b]quinazoline,
3-chloro-2-(heptylcarbamoyloxy)-11H-pyrido[2,1-b]quinazoline,
1,3-dichloro-2-(heptylcarbamoyloxy)-11H-pyrido[2,1-b]quinazoline,
1-chloro-2-methyl-1H-pyrido[2,1-b]quinazoline,
1-chloro-3-methyl-11H-pyrido[2,1-b]quinazoline,
1-chloro-4-methyl-11H-pyrido[2,1-b]quinazoline,
2-chloro-1-methyl-11H-pyrido[2,1-b]quinazoline,
3-chloro-1-methyl-11H-pyrido[2,1-b]quinazoline,
4-chloro-1-methyl-11H-pyrido[2,1-b]quinazoline,
3-chloro-1-methyl-11H-pyrido[2,1-b]quinazoline,
3-chloro-2-methyl-11H-pyrido[2,1-b]quinazoline,
3-chloro-4-methyl-11H-pyrido(2,1-b]quinazoline,
4-chloro-1-methyl-11H-pyrido[2,1-b]quinazoline,
4-chloro-2-methyl-11H-pyrido[2,1-b]quinazoline,
1-methyl-3-chloro-11H-pyrido[2,1-b]quinazoline,
3-chloro-1,4-dimethyl-11H-pyrido[2,1-b]quinazoline,
1-chloro-3-methyl-11H-pyrido[2,1-b]quinazoline,
1-methyl-3-chloro-11H-pyrido[2,1-b]quinazoline,
1,3-dichloro-2-methyl-11H-pyrido[2,1-b]quinazoline,
1,3-dichloro-4-methyl-11H-pyrido[2,1-b]quinazoline,
1,3-dichloro-2,4-dimethyl-11H-pyrido[2,1-b]quinazoline,
1-chloro-11,11-dimethyl-11H-pyrido[2,1-b]quinazoline,
3-chloro-11,11-dimethyl-11H-pyrido[2,1-b]quinazoline,
1,3-dichloro-11-methyl-11H-pyrido[2,1-b]quinazoline,
1,3-dichloro-11,11-dimethyl-11H-pyrido[2,1-b]quinazoline,
3-chloro-11-methylene-11H-pyrido[2,1-b]quinazoline,
1,3-dichloro-11-isopropylidene-11H-pyrido[2,1-b]quinazoline,
1,3-dichloro-11-methylene-11H-pyrido[2,1-b]quinazoline,
1,3-difluoro-11H-pyrido[2,1-b]quinazoline,
1-fluoro-3-bromo-11H-pyrido[2,1-b]quinazoline,
1-fluoro-3-iodo-11H-pyrido[2,1-b]quinazoline,
1-chloro-3-fluoro-11H-pyrido[2,1-b]quinazoline,
1-chloro-3-bromo-11H-pyrido[2,1-b]quinazoline,
1-chloro-3-iodo-11H-pyrido[2,1-b]quinazoline,
1-bromo-3-fluoro-11H-pyrido[2,1-b]quinazoline,
1-bromo-3-chloro-11H-pyrido[2,1-b]quinazoline,
1-bromo-3-iodo-11H-pyrido[2,1-b]quinazoline,
1,3-dibromo-11H-pyrido[2,1-b]quinazoline,
1-iodo-3-fluoro-11H-pyrido[2,1-b]quinazoline,
1-iodo-3-chloro-11H-pyrido[2,1-b]quinazoline,
1-iodo-3-bromo-11H-pyrido[2,1-b]quinazoline,
1,3-diiodo-11H-pyrido[2,1-b]quinazoline,
1-bromo-3-fluoro-11H-pyrido[2,1-b]quinazoline,
1-bromo-3-chloro-11H-pyrido[2,1-b]quinazoline,
1-bromo-3-iodo-11H-pyrido[2,1-b]quinazoline,
1,3-dibromo-11H-pyrido[2,1-b]quinazoline,
1-iodo-3-fluoro-11H-pyrido[2,1-b]quinazoline,
1-iodo-3-chloro-11H-pyrido[2,1-b]quinazoline,
1-iodo-3-bromo-11H-pyrido[2,1-b]quinazoline,
1,3-diiodo-11H-pyrido[2,1-b]quinazoline,
1,3-dichloro-6-methyl-11H-pyrido[2,1-b]quinazoline,
1,3-dichloro-7-methyl-11H-pyrido[2,1-b]quinazoline,
1,3-dichloro-8-methyl-11H-pyrido[2,1-b]quinazoline,
1,3-dichloro-9-methyl-11H-pyrido[2,1-b]quinazoline,
1,3-dichloro-6-fluoro-11H-pyrido[2,1-b]quinazoline,
1,3-dichloro-7-fluoro-11H-pyrido[2,1-b]quinazoline,
1,3-dichloro-8-fluoro-11H-pyrido[2,1-b]quinazoline,
1,3-dichloro-9-fluoro-11H-pyrido[2,1-b]quinazoline,
1,3,6-trichloro-11H-pyrido[2,1-b]quinazoline,
1,3,7-trichloro-11H-pyrido[2,1-b]quinazoline,
1,3,8-trichloro-11H-pyrido[2,1-b]quinazoline, and
1,3,9-trichloro-11H-pyrido[2,1-b]quinazoline.

EXAMPLE 15

(±)-1,3-dichloro-6,9-dihydro-11H-6,9-methanopyrido[2,1-b]quinazoline hydrochloride Two grams of 4,6-dichloroanthranilic acid was treated with 6 mL $SOCl_2$ in 25 mL benzene and heated to boil for 30 minutes. Then all volatiles were distilled out in vacuo. The light brownish residue was dissolved in 25 mL $CCl_4$ and cooled in ice bath. A solution of 1 g of (±)-2-azabicyclo[2.2.1]hept-5-en-3-one (Aldrich Chem. Co.) in 20 mL ethanol-free chloroform was added dropwise over a 2-hour period, then the mixture was stirred at room temperature for hours. Then the reaction mixture was refluxed briefly and concentrated in vacuo. The brown residue was chromatographed on silica gel using chloroformethyl acetate 12:1 as eluent. The corresponding fractions were concentrated in vacuo to provide the (±)-1,3-dichloro-11H-6,9-methanopyrido[2,1-b]quinazolin-11-one. This was dissolved in 25 mL glacial acetic acid at 50° C. Ten grams of zinc dust was added and the mixture was mechanically stirred. Then concentrated HCl was added dropwise (approximately 10 mL) in 7 minutes and the progress of the reaction was monitored by TLC. After 10 minutes, the excess of clumped zinc (pyrophoric!) was filtered off and the filtrate was diluted with 200 mL $CHCl_3$ and basified carefully with 20% NaOH (ice cooling). After filtration, the organic layer was separated, dried with $K_2CO_3$, and concentrated in vacuo. The residue was chromatographed using 300:25:1 $CHCl_3$:MeOH: 28% aqueous ammonia. The corresponding fractions were concentrated in vacuo, dissolved in 50 mL absolute ethanol, and treated with equivalent amount of 4N HCl. This was concentrated in vacuo and dried by twice coevaporating with 50 mL absolute EtOH. The residue was recrystallized from absolute ethyl alcohol-ethyl acetate to give white crystalline hydrochloride salt.

The (+) and (−) enantiomers are prepared by the same methodology from the commercially available enantiomeric lactams.

EXAMPLE 16

1,3-Dichloro-6,7,8,9,10,12-hexahydroazepino[2,1-b]quinazolin-12-ol
Method A:

To a solution of 2 g of 1,3-dichloro- 7,8,9,10-tetrahydroazepino[2,1-b]quinazolin-12(6H)-one in 100 mL of glacial acetic acid at 50° C. was added an intimately mixed mixture of 15 g zinc dust and 15 g silica gel (column chromatography grade). To this mechanically stirred suspension was added dropwise concentrated hydrochloric acid, while the progress of the reaction was followed by TLC (20:1 $CHCl_3$:MeOH, basified aliquots, extracted into chloroform). When the reaction was essentially complete, excess zinc was filtered off (pyrophoric!) the filtrate was concentrated in vacuo, basified, extracted with chloroform, and the crude extract was chromatographed using 20:1 chloroform-:methanol as eluent on a silica gel column. The corresponding fractions after concentration in vacuo gave the 1,3-dichloro- 6,7,8,9,10,12-hexahydroazepino[2,1-b]quinazolin-12-ol as an off-white crystalline solid.

Method B:

To a solution of 1 g of 1,3-dichloro- 7,8,9,10-tetrahydroazepino[2,1-b]quinazolin-12(6H)-one in 30 mL of hot triethylsilane was added 5 m of trifluoroacetic acid and the mixture was stirred at 100° C.–110° C. under nitrogen. More triethylsilane and trifluoroacetic acid were added until the reaction was substantially complete as evidenced by TLC (basified aliquot extracted into CHCl₃). Then all volatiles were removed in vacuo and the residue was basified, extracted into chloroform, and chromatographed using 20:1 chloroform:methanol on a silica gel column. Concentration of the corresponding fractions provided the desired 1,3-dichloro-6,7,8,9,10,12-hexahydroazepino[2,1-b]quinazolin-12-ol as a greyish-white solid.

I claim:

1. A compound of formula

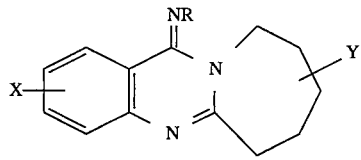

or a pharmaceutically acceptable salt thereof wherein

Y is hydrogen, hydroxy, carboxy, lower alkoxy, lower alkyl, keto, lower alkoxy carbonyl, or lower alkanoyl;

R is hydrogen, lower alkyl, lower alkenyl or lower alkynyl; and

X is absent or one to four substituents selected from halogen, lower alkyl, perfluorinated lower alkyl, hydroxy, carboxy, lower alkoxy, perfluorinated lower alkoxy, nitro, amino, lower alkanoyl amino and lower alkylcarbamoyloxy with the proviso that when Y is hydrogen and R is hydrogen, X is not absent.

2. A compound according to claim 1, wherein Y and R are hydrogen.

3. A compound according to claim 1, wherein X is absent or one to four substituents selected from halogen, lower alkyl, perfluorinated lower alkyl, and lower alkoxy.

4. A compound according to claim 3, wherein X is absent or one to two substituents selected from fluoro, chloro, bromo, iodo, methyl, methoxy, and trifluoromethyl.

5. A compound named 3-chloro-7,8,9,10-tetrahydroazepino[2,1-b]quinazolin-12(6H)imine.

6. A compound named 1,3-dichloro-6,7,8,9,10,12-hexahydroazepino[2,1-b]quinazolin-12-ol.

7. A compound of the formula

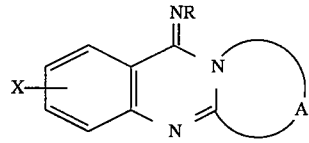

wherein A is

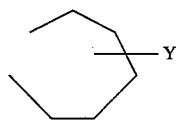

in which Y is hydrogen, hydroxy, carboxy, lower alkoxy, lower alkyl, aryl, heteroaryl, keto, lower alkoxy carbonyl or lower alkanoyl;

R is hydrogen, lower alkyl, lower alkenyl, lower alkynyl, hydroxy, lower alkoxy, aryl, aryloxy, aryllower alkyl, heteroaryl, or heteroaryllower alkyl; and X is absent or one to four substituents selected from halogen, lower alkyl, perfluorinated lower alkyl, hydroxy, carboxy, mercapto, lower alkoxy, lower thioalkoxy, perfluorinated lower alkoxy, perfluorinated lower thioalkoxy, nitro, amino, lower alkanoylamino, aryl, aryllower alkyl, heteroaryl, lower alkylcarbamoyloxy, and heteroaryllower alkyl; or a pharmaceutically acceptable acid addition salt thereof; with the provision that when Y is hydrogen and R is hydrogen, X is not absent.

8. A method of treating cognitive deficiencies through the inhibition of cholinesterase comprising administering to a mammal in need thereof a therapeutically effective amount in unit dosage form of a compound of the formula

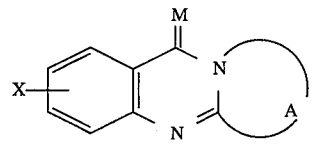

wherein A is

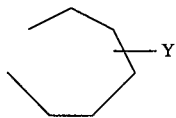

in which Y is hydrogen, hydroxy, carboxy, lower alkoxy, lower alkyl, aryl, heteroaryl, keto, lower alkoxycarbonyl, or lower alkanoyl, or its corresponding oxime;

M is =S, =NR, or

in which R and R' are each independently hydrogen, hydroxy, lower alkyl, lower alkenyl, lower alkynyl, lower alkoxy, aryl, aryloxy, aryllower alkyl, heteroaryl, or heteroaryllower alkyl and, when taken together, may form a three- to six-membered ring optionally containing one to three heteroatoms selected from nitrogen, oxygen, and sulfur; and X is absent or one to four substituents selected form halogen, lower alkyl, lower alkenyl or lower alkynyl, amino, lower alkylamino or di-lower alkylamino, nitro, lower alkylthio, aryl-, or heteroarylthio, mercapto, hydroxy, carboxy, lower alkoxy, aryl- or heteroaryloxy, lower alkyl-, aryl- or heteroarylsulfinyl, lower alkyl-, aryl- or heteroarylsulfonyl, perfluoro-lower-alkyl, perfluoro-lower-alkoxy, perfluoro-lower-alkylthio, perfluoro-lower-alkylsulfinyl, perfluoro-lower-alkylsulfonyl, lower alkyl-, aryl- or heteroarylcarbamoyl, di-lower-alkanoylamino, lower alkyl- aryl- or heteroarylsulfinyl-amido, lower alkyl-, aryl- or heteroarylsulfonylamido, perfluoro-lower-alkylsulfinylamido, perfluoro-lower-alkyl-sulfonylamido, trialkylsilyl, lower alkanoyl, perfluoro-lower-alkanoyl-, loweralkanoyl-lower alkyl, perfluoro-lower-alkanoyl-lower alkyl, lower alkyl-, aryl- or heteroarylcarbamoyloxy, di-lower-alkyl-, diaryl- or diheteroarylcarbamoyloxy, lower alkyl-,aryl- or heteroarylcarbamoylthio, lower alkyl-, aryl or hetero-arylcarbamoyl-lower-alkyl, imido-lower-alkyl, aryl, aryllower-alkyl, heteroaryl and heteroaryllower-alkyl; or a pharmaceutically acceptable acid addition salt thereof.

9. A method of treating cognitive deficiencies through the inhibition of cholinesterase comprising administering to a mammal in need thereof a therapeutically effective amount in unit dosage form of a compound of the formula

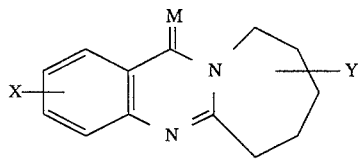

or a pharmaceutically acceptable salt thereof in which

Y is hydrogen, hydroxy, carboxy, lower alkoxy, lower alkyl, keto, lower alkoxy carbonyl, or lower alkanoyl;

M is

in which R and R' are each independently hydrogen, or lower alkyl and

X is absent or one to four substituents selected from halogen, lower alkyl, perfluorinated lower alkyl, hydroxy, carboxy, lower alkoxy, perfluorinated lower alkoxy, nitro, amino, lower alkanoyl amino and lower alkylcarbamoyloxy.

10. A method of treating cognitive deficiencies through the inhibition of cholinesterase comprising administering to a mammal in need thereof a therapeutically effective amount in unit dosage form of a compound 1,3-dichloro-6,7,8,9,10,12-hexahydroazepino[2,1-b]quinazoline.

11. A method of treating senile dementia comprising administering to mammal in need thereof a therapeutically effective amount in unit dosage form of a compound 1,3-dichloro-6,7,8,9,10,12-hexahydroazepino[2,1-b]quinazoline.

* * * * *